US012692433B2

(12) United States Patent
Jo et al.

(10) Patent No.: US 12,692,433 B2
(45) Date of Patent: Jul. 28, 2026

(54) ORGANIC ELECTROLUMINESCENCE DEVICE AND AMINE COMPOUND FOR ORGANIC ELECTROLUMINESCENCE DEVICE

(71) Applicant: Samsung Display Co., Ltd., Yongin-si (KR)

(72) Inventors: Sohee Jo, Cheonan-si (KR); Dongjun Kim, Suwon-si (KR); Minji Kim, Hwaseong-si (KR); Hankyu Pak, Suwon-si (KR); Eunjae Jeong, Hwaseong-si (KR); Sanghyun Han, Hwaseong-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 751 days.

(21) Appl. No.: 17/232,773

(22) Filed: Apr. 16, 2021

(65) Prior Publication Data

US 2022/0059771 A1 Feb. 24, 2022

(30) Foreign Application Priority Data

Aug. 21, 2020 (KR) ........................ 10-2020-0105637

(51) Int. Cl.
*C07D 209/82* (2006.01)
*C07D 209/86* (2006.01)
(Continued)

(52) U.S. Cl.
CPC ............ *C09K 11/06* (2013.01); *C07D 209/88* (2013.01); *C07D 409/12* (2013.01);
(Continued)

(58) Field of Classification Search
CPC .. H10K 85/631; H10K 85/633; H10K 85/636; C07C 13/72; C07C 211/60
See application file for complete search history.

(56) References Cited

U.S. PATENT DOCUMENTS 4,720,432 A 1/1988 VanSlyke et al.
5,061,569 A 10/1991 VanSlyke et al.
(Continued)

FOREIGN PATENT DOCUMENTS

CN 1787988 A 6/2006
CN 1852910 A 10/2006
(Continued)

OTHER PUBLICATIONS

Chinese Office Action dated Nov. 28, 2024, issued in corresponding Chinese Patent Application No. 202110884106.2, 14 pages.

*Primary Examiner* — Rachel Simbana
(74) *Attorney, Agent, or Firm* — Womble Bond Dickinson (US) LLP

(57) ABSTRACT

An organic electroluminescence device includes a first electrode and a second electrode which face each other, and a plurality of organic layers between the first electrode and the
(Continued)

second electrode, where at least one of the organic layers includes an amine compound represented by Formula 1, and the organic electroluminescence device may exhibit improved luminous efficiency:

Formula 1

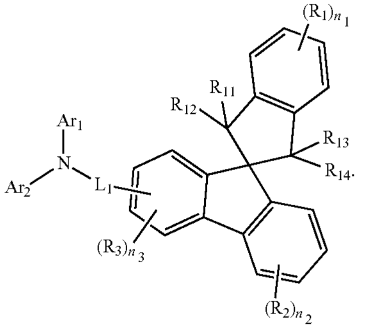

12 Claims, 6 Drawing Sheets

(51) Int. Cl.

| | |
|---|---|
| ***C07D 209/88*** | (2006.01) |
| ***C07D 307/91*** | (2006.01) |
| ***C07D 333/76*** | (2006.01) |
| ***C07D 405/12*** | (2006.01) |
| ***C07D 409/12*** | (2006.01) |
| ***C09K 11/06*** | (2006.01) |
| ***H10K 50/11*** | (2023.01) |
| ***H10K 50/15*** | (2023.01) |
| ***H10K 85/60*** | (2023.01) |
| ***H10K 101/10*** | (2023.01) |

(52) U.S. Cl.

CPC ......... *H10K 85/633* (2023.02); *H10K 85/636* (2023.02); *C09K 2211/1018* (2013.01); *H10K 50/11* (2023.02); *H10K 50/156* (2023.02); *H10K 85/623* (2023.02); *H10K 85/626* (2023.02); *H10K 85/6572* (2023.02); *H10K 85/6576* (2023.02); *H10K 2101/10* (2023.02)

(56) References Cited

U.S. PATENT DOCUMENTS

| | | | |
|---|---|---|---|
| 6,242,115 B1 | 6/2001 | Thomson et al. | |
| 7,431,997 B2 | 10/2008 | Hwang et al. | |
| 7,598,667 B2 | 10/2009 | Kawamura et al. | |
| 9,929,358 B2 | 3/2018 | Hwang et al. | |
| 9,991,450 B2 | 6/2018 | Nishiura et al. | |
| 2007/0018569 A1* | 1/2007 | Kawamura | C07C 211/61 564/426 |
| 2007/0231503 A1* | 10/2007 | Hwang | H10K 50/81 428/411.1 |
| 2008/0038587 A1* | 2/2008 | Wen | H10K 85/633 428/704 |
| 2017/0179204 A1 | 6/2017 | Lim et al. | |
| 2019/0185460 A1 | 6/2019 | Kim et al. | |

FOREIGN PATENT DOCUMENTS

| | | | |
|---|---|---|---|
| CN | 102203213 A | 9/2011 | |
| CN | 102449106 A | 5/2012 | |
| CN | 102958906 A | 3/2013 | |
| CN | 106848072 A | 6/2017 | |
| CN | 111056959 A | 4/2020 | |
| CN | 111056960 A | 4/2020 | |
| CN | 111057005 A | 4/2020 | |
| JP | H 11-144873 A | 5/1999 | |
| JP | 2003-133075 A | 5/2003 | |
| JP | 4103493 B2 | 6/2008 | |
| JP | 4464070 B2 | 5/2010 | |
| JP | 4573923 B2 | 11/2010 | |
| JP | 4589223 B2 | 12/2010 | |
| KR | 10-2006-0009349 A | 1/2006 | |
| KR | 10-2006-0080922 A | 7/2006 | |
| KR | 10-2011-0121147 A | 11/2011 | |
| KR | 10-2015-0087705 A | 7/2015 | |
| KR | 10-2017-0075115 A | 7/2017 | |
| KR | 10-2022391 B1 | 9/2019 | |
| KR | 10-2019-0131468 A | 11/2019 | |
| WO | WO-2010110553 A2 * | 9/2010 | H10K 85/631 |
| WO | WO 2011/136482 A1 | 11/2011 | |

* cited by examiner

ORGANIC ELECTROLUMINESCENCE DEVICE AND AMINE COMPOUND FOR ORGANIC ELECTROLUMINESCENCE DEVICE

CROSS-REFERENCE TO RELATED APPLICATION

This application claims priority to and the benefit of Korean Patent Application No. 10-2020-0105637, filed on Aug. 21, 2020, the entire content of which is hereby incorporated by reference.

BACKGROUND

1. Field

One or more aspects of embodiments of the present disclosure relate to an organic electroluminescence device and an amine compound utilized therein, and for example, to an amine compound utilized as a luminescent material and an organic electroluminescence device including the same.

2. Description of Related Art

Organic electroluminescence displays are being actively developed as image display apparatuses. Unlike liquid crystal display apparatuses and/or the like, an organic electroluminescence display is a so-called self-luminescent display apparatus, in which holes and electrons respectively injected from a first electrode and a second electrode recombine in an emission layer, and a luminescent material including an organic compound in the emission layer emits light to implement display.

In the application of an organic electroluminescence device to a display apparatus, an organic electroluminescence device having a low driving voltage, high luminous efficiency, and/or a long service life is desired, and development of materials capable of stably attaining such characteristics in an organic electroluminescence device is desired.

In addition, materials for hole transport (e.g., of a hole transport layer) are being developed in order to realize a high efficient organic electroluminescence device.

SUMMARY

One or more aspects of embodiments of the present disclosure are directed toward an organic electroluminescence device in which luminous efficiency and/or device service life are improved.

One or more aspects of embodiments of the present disclosure are directed toward an amine compound capable of improving the luminous efficiency and/or the device service life of an organic electroluminescence device.

One or more embodiments of the present disclosure provide an organic electroluminescence device including: a first electrode; a second electrode facing the first electrode; and a plurality of organic layers disposed between the first electrode and the second electrode, wherein at least one organic layer among the plurality of organic layers includes an amine compound, the amine compound includes an amine group and a spirofluorene-indene group substituted at the amine group, and the amine group is connected to one benzene ring of a fluorene group moiety included in the spirofluorene-indene group.

In an embodiment, the spirofluorene-indene group may be bonded to the amine group via a linker, may be or directly bonded to the amine group.

In an embodiment, the plurality of organic layers may include a hole transport region disposed on the first electrode, an emission layer disposed on the hole transport region, and an electron transport region disposed on the emission layer, and the emission layer may include the amine compound.

In an embodiment, the hole transport region may include a hole injection layer disposed on the first electrode, and a hole transport layer disposed on the hole injection layer, and the hole transport layer may include the amine compound.

In an embodiment, the hole transport region may include a plurality of organic hole transport layers, and an organic hole transport layer that is adjacent to the emission layer among the plurality of organic layers may include the amine compound.

One or more embodiments of the present disclosure provide an organic electroluminescence device includes a first electrode, a second electrode facing the first electrode, and a plurality of organic layers disposed between the first electrode and the second electrode, wherein at least one organic layer among the organic layers includes an amine compound represented by Formula 1:

Formula 1

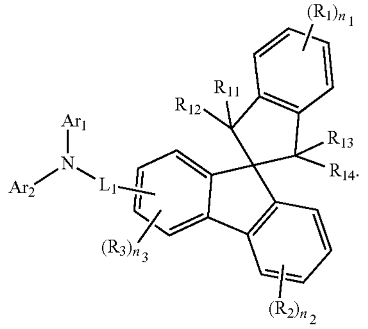

In Formula 1, $Ar_1$ and $Ar_2$ may each independently be a substituted or unsubstituted aryl group having 6 to 30 ring-forming carbon atoms or a substituted or unsubstituted heteroaryl group having 2 to 30 ring-forming carbon atoms, $L_1$ may be a direct linkage, a substituted or unsubstituted arylene group having 6 to 30 ring-forming carbon atoms, or a substituted or unsubstituted heteroarylene group having 2 to 30 ring-forming carbon atoms, $R_1$ to $R_3$ may each independently be a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms, $R_{11}$ to $R_{14}$ may each independently be a hydrogen atom, a deuterium atom, a halogen atom, a substituted or unsubstituted alkyl group having 1 to 20 carbon atoms, $n_1$ and $n_2$ may each independently be an integer of 0 to 4, and $n_3$ may be an integer of 0 to 3.

In an embodiment, the amine compound represented by Formula 1 may be a monoamine compound.

In an embodiment, the amine compound represented by Formula 1 may be represented by Formula 2-1 or Formula 2-2:

Formula 2-1

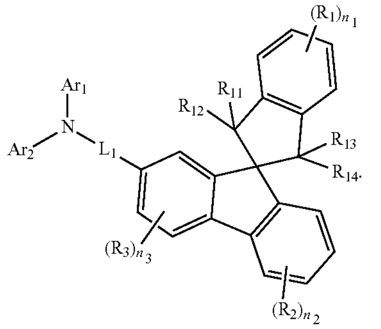

Formula 2-2

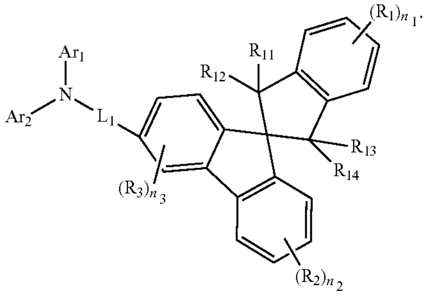

In Formula 2-1 and Formula 2-2, $Ar_1$, $Ar_2$, $L_1$, $R_1$, $R_2$, $R_3$, $R_{11}$, $R_{12}$, $R_{13}$, $R_{14}$, $n_1$, $n_2$, and $n_3$ may each independently be the same as defined in Formula 1.

In an embodiment, the amine compound represented by Formula 1 may be represented by Formula 3:

Formula 3

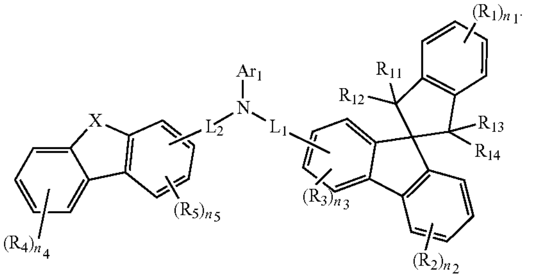

In Formula 3, X may be O, S, or $NAr_3$, $Ar_3$ may be a hydrogen atom, a substituted or unsubstituted aryl group having 6 to 30 ring-forming carbon atoms, or a substituted or unsubstituted heteroaryl group having 2 to 30 ring-forming carbon atoms, $L_2$ is a direct linkage, a substituted or unsubstituted arylene group having 6 to 30 ring-forming carbon atoms, or a substituted or unsubstituted heteroarylene group having 2 to 30 ring-forming carbon atoms, $R_4$ and $R_5$ may each independently be a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms, $n_4$ may be an integer of 0 to 4, $n_5$ may be an integer of 0 to 3, and $Ar_1$, $L_1$, $R_1$, $R_2$, $R_3$, $R_{11}$, $R_{12}$, $R_{13}$, $R_{14}$, $n_1$, $n_2$, and $n_3$ may each independently be the same as defined in Formula 1.

In an embodiment, the amine compound represented by Formula 1 may be represented by any one among Formula 4-1 to Formula 4-3:

Formula 4-1

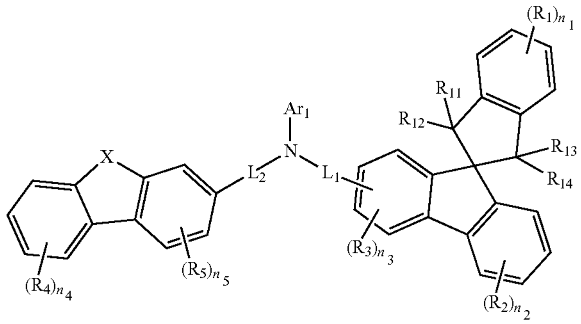

Formula 4-2

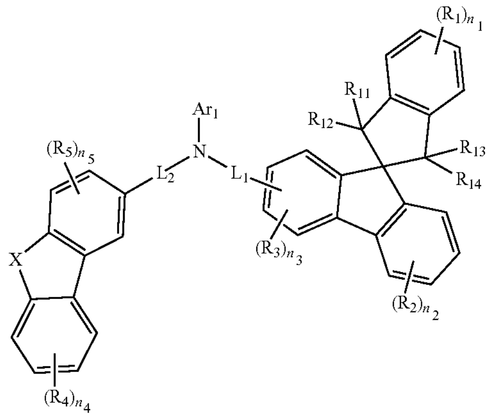

Formula 4-3

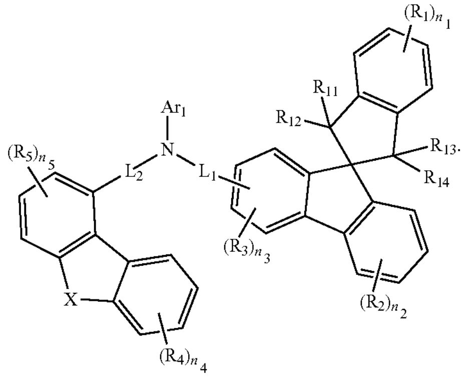

In Formula 4-1 to Formula 4-3, $Ar_1$, X, $L_1$, $L_2$, $R_1$, $R_2$, $R_3$, $R_4$, $R_5$, $R_{11}$, $R_{12}$, $R_{13}$, $R_{14}$, $n_1$, $n_2$, $n_3$, $n_4$, and $n_5$ may each independently be the same as defined in Formula 1 and Formula 3.

In an embodiment, the amine compound represented by Formula 1 may be represented by any one among Formula 5-1 to Formula 5-3:

Formula 5-1

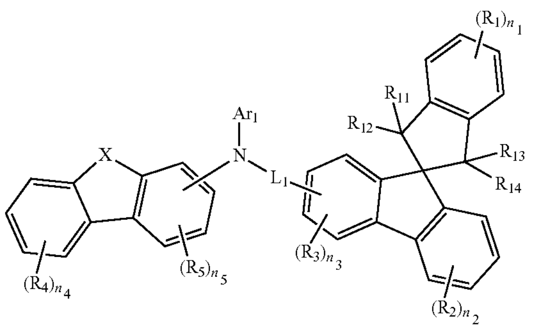

Formula 5-2

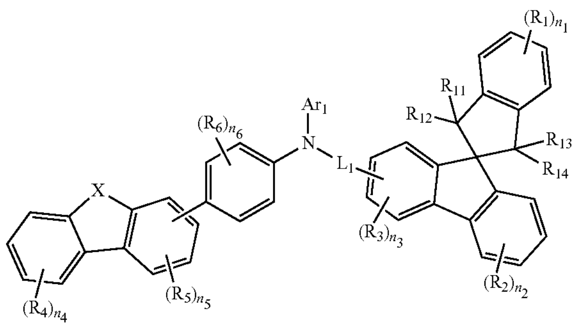

Formula 5-3

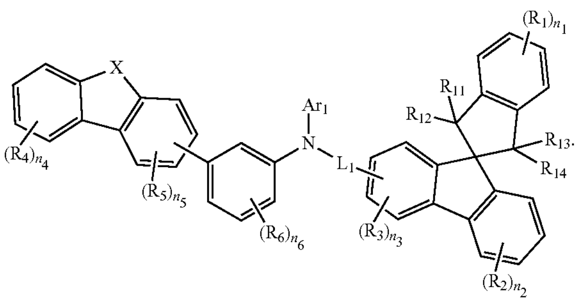

In Formula 5-1 to Formula 5-3, $R_6$ may be a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms, $n_6$ may be an integer of 0 to 4, and $Ar_1$, X, $L_1$, $R_1$, $R_2$, $R_3$, $R_4$, $R_5$, $R_{11}$, $R_{12}$, $R_{13}$, $R_{14}$, $n_1$, $n_2$, $n_3$, $n_4$, and $n_6$ may each independently be the same as defined in Formula 1 and Formula 3.

In an embodiment, $Ar_1$ and $Ar_2$ may each independently be a substituted or unsubstituted phenyl group, a substituted or unsubstituted biphenyl group, a substituted or unsubstituted naphthyl group, a substituted or unsubstituted fluorenyl group, a substituted or unsubstituted carbazole group, a substituted or unsubstituted dibenzofuran group, or a substituted or unsubstituted dibenzothiophene group.

In an embodiment, $Ar_1$ and $Ar_2$ may be different from each other.

One or more embodiments of the present disclosure provide the amine compound is represented by Formula 1.

BRIEF DESCRIPTION OF THE DRAWINGS

The accompanying drawings are included to provide a further understanding of the present disclosure, and are incorporated in and constitute a part of this specification. The drawings illustrate example embodiments of the present disclosure and, together with the description, serve to explain principles of the present disclosure. In the drawings.

DETAILED DESCRIPTION

Figure 1:
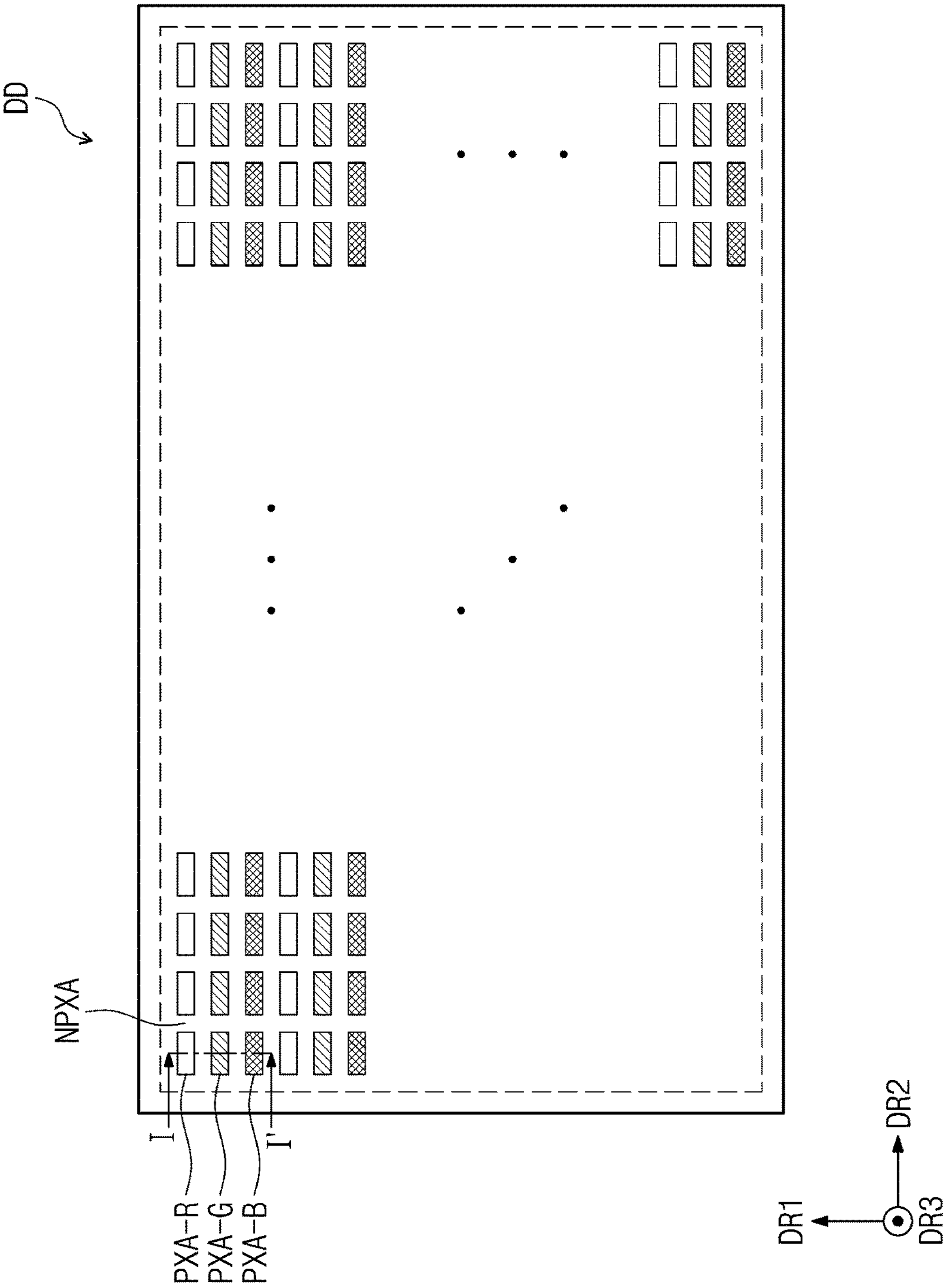
FIG. 1 is a plan view of a display apparatus according to an embodiment of the present disclosure.

The present disclosure may be modified in various suitable manners and have many forms, and selected example embodiments will be illustrated in the drawings and described in this text in more detail. It should be understood, however, that it is not intended to limit the present disclosure to the particular forms disclosed, but rather, is intended to cover all modifications, equivalents, and alternatives falling within the spirit and scope of the present disclosure.

In the present description, when an element (or a region, a layer, a portion, etc.) is referred to as being "on," "connected to," or "coupled to" another element, the element may be directly disposed on/connected to/coupled to the other element, or that a third element may be disposed therebetween. When an element is referred to as being "directly on," "directly connected to," or "directly coupled to" another element, there are no intervening elements present.

Like reference numerals refer to like elements, and duplicative descriptions thereof may not be provided. Also, in the drawings, thicknesses, ratios, and dimensions of elements may be exaggerated for an effective description of technical contents.

The term "and/or" includes any and all combinations of one or more of the associated listed items.

It will be understood that, although the terms "first," "second," etc. may be used herein to describe one or more suitable elements, these elements should not be limited by these terms. These terms are only utilized to distinguish one element from another. For example, a first element may be referred to as a second element, and, similarly, the second element may be referred to as the first element, without departing from the scope of the present disclosure. The terms of a singular form may include plural forms unless the context clearly indicates otherwise.

In some embodiments, terms such as "below," "lower," "above," "upper," and/or the like are used to describe the relationship of the configurations shown in the drawings.

The terms are used as relative concepts, and are described with reference to the directions indicated in the drawings.

Unless otherwise defined, all terms (including technical and scientific terms) used herein have the same meaning as commonly understood by one of ordinary skill in the art to which the present disclosure pertains. It is also to be understood that terms defined in commonly used dictionaries should be interpreted as having meanings consistent with the meanings in the context of the related art, and are expressly defined herein unless they are interpreted in an ideal or overly formal sense.

It should be understood that the terms "includes," "including," "comprises," "comprising," and/or "have" are intended to specify the presence of stated features, integers, steps, operations, elements, components, or combinations thereof in the disclosure, but do not preclude the presence or addition of one or more other features, integers, steps, operations, elements, components, or combinations thereof.

In the description, the term "substituted or unsubstituted" may refer to a state of being unsubstituted, or substituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group. Each of the substituents may be further substituted or unsubstituted. For example, a biphenyl group may be interpreted as a named aryl group, or as a phenyl group substituted with a phenyl group.

In the description, the phrase "bonded to an adjacent group to form a ring" may indicate that one is bonded to an adjacent group to form a substituted or unsubstituted hydrocarbon ring, or a substituted or unsubstituted heterocycle. The hydrocarbon ring may be an aliphatic hydrocarbon ring or an aromatic hydrocarbon ring. The heterocycle may be an aliphatic heterocycle or an aromatic heterocycle. The rings formed by being bonded to an adjacent group may be monocyclic or polycyclic. In some embodiments, the rings formed by being bonded to each other may be connected to another ring to form a spiro structure.

In the description, the term "an adjacent group" may refer to a substituent on the same atom or point, a substituent on an atom that is directly connected to the base atom or point, or a substituent sterically positioned (e.g., within intramolecular bonding distance) to the corresponding substituent. For example, two methyl groups in 1,2-dimethylbenzene may be interpreted as "adjacent groups" to each other and two ethyl groups in 1,1-diethylcyclopentane may be interpreted as "adjacent groups" to each other. In addition, two methyl groups in 4,5-dimethylphenanthrene may be interpreted as "adjacent groups" to each other.

In the description, non-limiting examples of the halogen atom include a fluorine atom, a chlorine atom, a bromine atom, and/or an iodine atom.

In the description, the alkyl group may be a linear, branched or cyclic type or chain. The number of carbons in the alkyl group is 1 to 50, 1 to 30, 1 to 20, 1 to 10, or 1 to 6. Non-limiting examples of the alkyl group include a methyl group, an ethyl group, an n-propyl group, an isopropyl group, an n-butyl group, an s-butyl group, a t-butyl group, an i-butyl group, a 2-ethylbutyl group, a 3,3-dimethylbutyl group, an n-pentyl group, an i-pentyl group, a neopentyl group, a t-pentyl group, a cyclopentyl group, a 1-methylpentyl group, a 3-methylpentyl group, a 2-ethylpentyl group, a 4-methyl-2-pentyl group, an n-hexyl group, a 1-methylhexyl group, a 2-ethylhexyl group, a 2-butylhexyl group, a cyclohexyl group, a 4-methylcyclohexyl group, a 4-t-butylcyclohexyl group, an n-heptyl group, a 1-methylheptyl group, a 2,2-dimethylheptyl group, a 2-ethylheptyl group, a 2-butylheptyl group, an n-octyl group, a t-octyl group, a 2-ethyloctyl group, a 2-butyloctyl group, a 2-hexyloctyl group, a 3,7-dimethyloctyl group, a cyclooctyl group, an n-nonyl group, an n-decyl group, an adamantyl group, a 2-ethyldecyl group, a 2-butyldecyl group, a 2-hexyldecyl group, a 2-octyldecyl group, an n-undecyl group, an n-dodecyl group, a 2-ethyldodecyl group, a 2-butyldodecyl group, a 2-hexyldocecyl group, a 2-octyldodecyl group, an n-tridecyl group, an n-tetradecyl group, an n-pentadecyl group, an n-hexadecyl group, a 2-ethylhexadecyl group, a 2-butylhexadecyl group, a 2-hexylhexadecyl group, a 2-octylhexadecyl group, an n-heptadecyl group, an n-octadecyl group, an n-nonadecyl group, an n-eicosyl group, a 2-ethyleicosyl group, a 2-butyleicosyl group, a 2-hexyleicosyl group, a 2-octyleicosyl group, an n-henicosyl group, an n-docosyl group, an n-tricosyl group, an n-tetracosyl group, an n-pentacosyl group, an n-hexacosyl group, an n-heptacosyl group, an n-octacosyl group, an n-nonacosyl group, an n-triacontyl group, etc., but embodiments of the present disclosure are not limited thereto.

The term "hydrocarbon ring group" refers to any functional group or substituent derived from an aliphatic hydrocarbon ring. The hydrocarbon ring group may be a saturated hydrocarbon ring group having 5 to 20 ring-forming carbon atoms.

The term "aryl group" herein refers to any functional group or substituent derived from an aromatic hydrocarbon ring. The aryl group may be a monocyclic aryl group or a polycyclic aryl group. The number of ring-forming carbon atoms in the aryl group may be 6 to 30, 6 to 20, or 6 to 15. Non-limiting examples of the aryl group include a phenyl group, a naphthyl group, a fluorenyl group, an anthracenyl group, a phenanthryl group, a biphenyl group, a terphenyl group, a quaterphenyl group, a quinquephenyl group, a sexiphenyl group, a triphenylenyl group, a pyrenyl group, a benzofluoranthenyl group, a chrysenyl group, etc., but embodiments of the present disclosure are not limited thereto.

In the description, the fluorenyl group may be substituted, and two substituents may be combined with each other to form a spiro structure. Non-limiting examples of cases where the fluorenyl group is substituted are as follows. However, embodiments of the present disclosure are not limited thereto

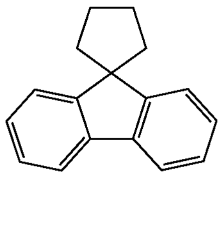
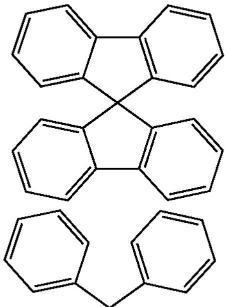
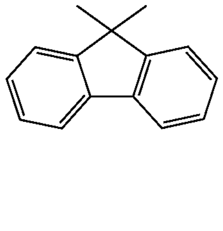
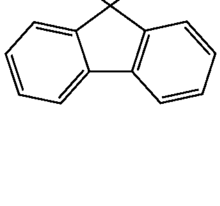.

The term “heterocyclic group” refers to any functional group or substituent derived from a ring including at least one of boron (B), oxygen (O), nitrogen (N), phosphorus (P), silicon (Si), or selenium (Se) as a heteroatom. The term “heterocyclic group” includes an aliphatic heterocyclic group and an aromatic heterocyclic group. The aromatic heterocyclic group may be a heteroaryl group. The aliphatic heterocycle and the aromatic heterocycle may each independently be monocyclic or polycyclic.

In the description, the heterocyclic group may include at least one of B, O, N, P, Si or S as a heteroatom. When the heterocyclic group includes two or more heteroatoms, the two or more heteroatoms may be the same as or different from each other. The heterocyclic group may be a monocyclic heterocyclic group or a polycyclic heterocyclic group and has the concept including a heteroaryl group. The ring-forming carbon number of the heterocyclic group may be 2 to 30, 2 to 20, or 2 to 10.

In the description, the aliphatic heterocyclic group may include one or more among B, O, N, P, Si, and S as a heteroatom. The number of ring-forming carbon atoms of the aliphatic heterocyclic group may be 2 to 30, 2 to 20, or 2 to 10. Non-limiting examples of the aliphatic heterocyclic group include an oxirane group, a thiirane group, a pyrrolidine group, a piperidine group, a tetrahydrofuran group, a tetrahydrothiophene group, a thiane group, a tetrahydropyran group, a 1,4-dioxane group, etc., but embodiments of the present disclosure are not limited thereto.

The heteroaryl group herein may include at least one of B, O, N, P, Si, or S as a heteroatom. When the heteroaryl group contains two or more heteroatoms, the two or more heteroatoms may be the same as or different from each other. The heteroaryl group may be a monocyclic heteroaryl group or a polycyclic heteroaryl group. The number of ring-forming carbon atoms in the heteroaryl group may be 2 to 30, 2 to 20, or 2 to 10. Non-limiting examples of the heteroaryl group include a thiophene group, a furan group, a pyrrole group, an imidazole group, a triazole group, a pyridine group, a bipyridine group, a pyrimidine group, a triazine group, a triazole group, an acridyl group, a pyridazine group, a pyrazinyl group, a quinoline group, a quinazoline group, a quinoxaline group, a phenoxazine group, a phthalazine group, a pyrido pyrimidine group, a pyrido pyrazine group, a pyrazino pyrazine group, an isoquinoline group, an indole group, a carbazole group, an N-arylcarbazole group, an N-heteroarylcarbazole group, an N-alkylcarbazole group, a benzoxazole group, a benzimidazole group, a benzothiazole group, a benzocarbazole group, a benzothiophene group, a dibenzothiophene group, a thienothiophene group, a benzofuran group, a phenanthroline group, a thiazole group, an isoxazole group, an oxazole group, an oxadiazolyl group, a thiadiazole group, a phenothiazine group, a dibenzosilole group, a dibenzofuran group, etc., but embodiments of the present disclosure are not limited thereto.

The description with respect to the aryl group may be applied to an arylene group, except that the arylene group is a divalent group. The description with respect to the heteroaryl group may be applied to a heteroarylene group, except that the heteroarylene group is a divalent group.

In the description, the silyl group includes an alkylsilyl group and an arylsilyl group. Non-limiting examples of the silyl group include trimethylsilyl, triethylsilyl, t-butyldimethylsilyl, vinyldimethylsilyl, propyldimethylsilyl, triphenylsilyl, diphenylsilyl, phenylsilyl, etc. However, embodiments of the present disclosure are not limited thereto.

In the description, the number of carbon atoms in the amino group is not specifically limited, but may be 1 to 30. The amino group may include an alkyl amino group, an aryl amino group, or a heteroaryl amino group. Non-limiting examples of the amino group include a methylamino group, a dimethylamino group, a phenylamino group, a diphenylamino group, a naphthylamino group, a 9-methyl-anthracenylamino group, a triphenylamino group, etc., but are not limited thereto.

In the description, the number of ring-forming carbon atoms in the carbonyl group may be 1 to 40, 1 to 30, or 1 to 20. The carbonyl group may have the following example structures, but embodiments of the present disclosure are not limited thereto.

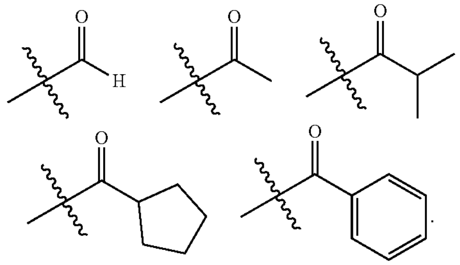

In the description, the number of carbon atoms in the sulfinyl group and the sulfonyl group is not particularly limited, but may be 1 to 30. The sulfinyl group may include an alkyl sulfinyl group and an aryl sulfinyl group. The sulfonyl group may include an alkyl sulfonyl group and an aryl sulfonyl group.

In the description, a thiol group may include an alkylthio group and an arylthio group. The term “thiol group” may refer to a sulfur atom bonded to thane alkyl group or an aryl group as defined above. Non-limiting examples of the thiol group include a methylthio group, an ethylthio group, a propylthio group, a pentylthio group, a hexylthio group, an octylthio group, a dodecylthio group, a cyclopentylthio group, a cyclohexylthio group, a phenylthio group, a naphthylthio group, but embodiments of the present disclosure are not limited thereto.

The term “oxy group” herein may refer to an oxygen atom is bonded to an alkyl group or an aryl group as defined. The oxy group may include an alkoxy group and an aryl oxy group. The alkoxy group may be a linear chain, a branched chain or a ring chain. The number of carbon atoms in the alkoxy group is not particularly limited, but may be, for example, 1 to 20 or 1 to 10. Non-limiting examples of the oxy group may methoxy, ethoxy, n-propoxy, isopropoxy, butoxy, pentyloxy, hexyloxy, octyloxy, nonyloxy, decyloxy, benzyloxy, etc., without limitation.

The term “boron group” herein may refer to a boron atom is bonded to an alkyl group or an aryl group as defined. The boron group includes an alkyl boron group and an aryl boron group. Non-limiting examples of the boron group include a trimethylboron group, a triethylboron group, a t-butyldimethylboron group, a triphenylboron group, a diphenylboron group, a phenylboron group, etc., but embodiments of the present disclosure are not limited thereto.

In the description, the alkenyl group may be linear or branched. The number of carbon atoms in the alkenyl group is not specifically limited, but may be 2 to 30, 2 to 20, or 2 to 10. Non-limiting examples of the alkenyl group include a vinyl group, a 1-butenyl group, a 1-pentenyl group, a 1,3-butadienyl aryl group, a styrenyl group, a styryl vinyl group, etc., but embodiments of the present disclosure are not limited thereto.

In the description, the number of carbon atoms in an amine group is not specifically limited, but may be 1 to 30. The amine group may include an alkyl amine group and an aryl amine group. Non-limiting examples of the amine group include a methylamine group, a dimethylamine group, a phenylamine group, a diphenylamine group, a naphthylamine group, a 9-methyl-anthracenylamine group, a triphenylamine group, etc., but embodiments of the present disclosure are not limited thereto.

In the description, the alkyl group in an alkylthio group, an alkylsulfoxy group, an alkylaryl group, an alkylamino group, an alkyl boron group, an alkyl silyl group, and an alkyl amine group is the same as in the examples of the alkyl group described.

In the description, the aryl group in an aryloxy group, an arylthio group, an arylsulfoxy group, an arylamino group, an arylboron group, an arylsilyl group, an arylamine group is substantially the same as in the examples of the aryl group described.

A "direct linkage" herein may refer to a single bond.

In some embodiments,

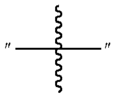

herein refers to a position to be connected to another formula, group or moiety.

Hereinafter, embodiments of the present disclosure will be described with reference to the accompanying drawings.

Figure 2:
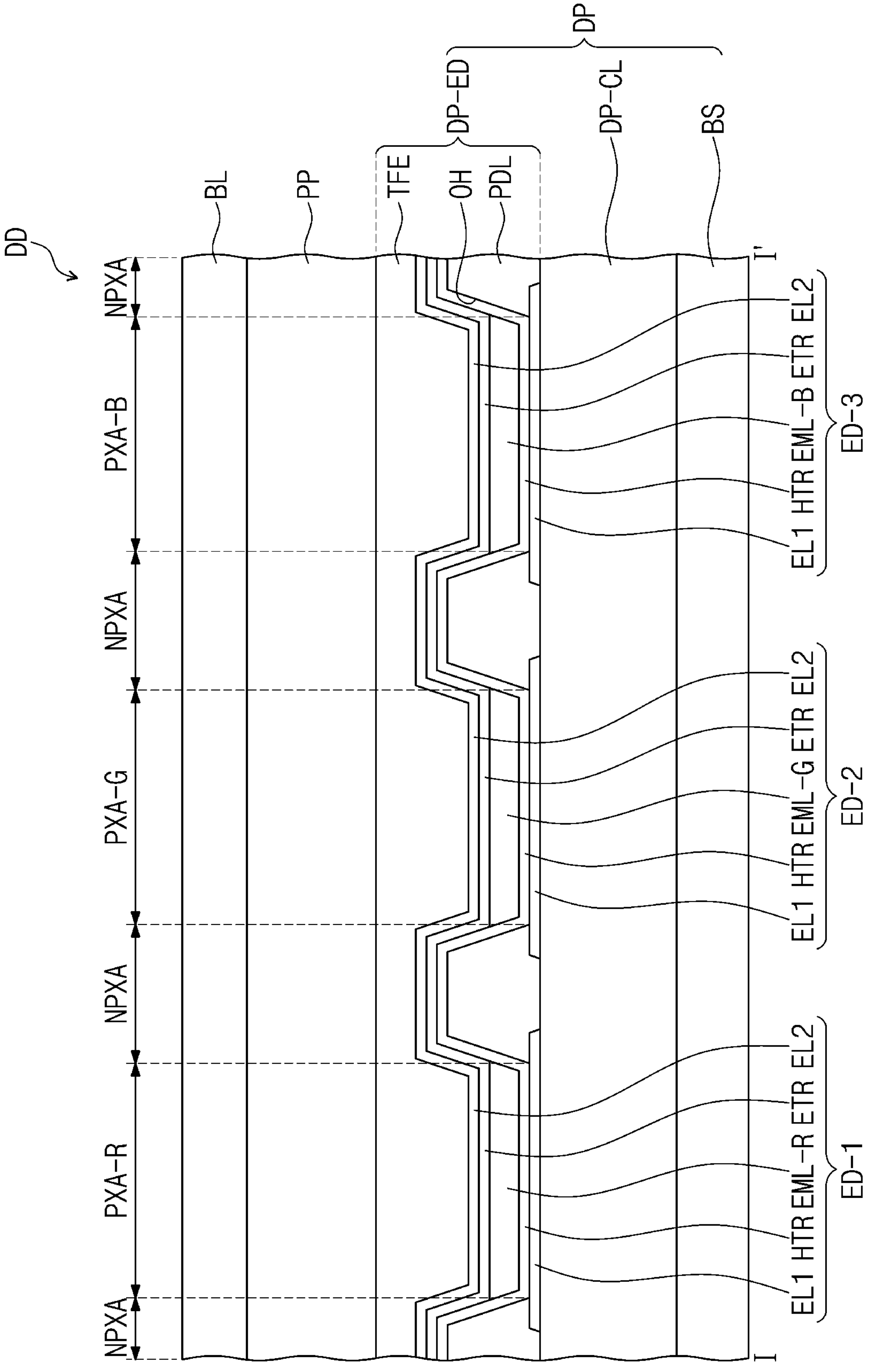
FIG. 2 is a cross-sectional view of a display apparatus according to an embodiment of the present disclosure.

FIG. 1 is a plan view illustrating an embodiment of a display apparatus DD. FIG. 2 is a cross-sectional view of the display apparatus DD of the embodiment. FIG. 2 is a cross-sectional view illustrating a part taken along line I-I' of FIG. 1.

The display apparatus DD may include a display panel DP and an optical layer PP disposed on the display panel DP. The display panel DP includes light emitting devices ED-1, ED-2, and ED-3. The display apparatus DD may include a plurality of light emitting devices ED-1, ED-2, and ED-3. The optical layer PP may be disposed on the display panel DP and control or reduce reflection of external light in the display panel DP. The optical layer PP may include, for example, a polarization layer or a color filter layer. In some embodiments, the optical layer PP may be omitted from the display apparatus DD of an embodiment. In some embodiments, a filling layer may be further included between the optical layer PP and the display panel DP. The filling layer may include, for example, at least any one of a silicone-based polymer resin, an acrylic-based polymer resin, or an urethane-based polymer resin.

The display panel DP may include a base layer BS, a circuit layer DP-CL provided on the base layer BS, and a display device layer DP-ED. The display device layer DP-ED may include a pixel defining film PDL, the light emitting devices ED-1, ED-2, and ED-3 disposed between portions of the pixel defining film PDL, and an encapsulation layer TFE disposed on the light emitting devices ED-1, ED-2, and ED-3.

The base layer BS may be a member which provides a base surface on which the display device layer DP-ED is disposed. The base layer BS may be a glass substrate, a metal substrate, a plastic substrate, etc. However, embodiments of the present disclosure are not limited thereto, and the base layer BS may be an inorganic layer, an organic layer, or a composite material layer.

In an embodiment, the circuit layer DP-CL is disposed on the base layer BS, and the circuit layer DP-CL may include a plurality of transistors. Each of the transistors may include a control electrode, an input electrode, and an output electrode. For example, the circuit layer DP-CL may include a switching transistor and a driving transistor in order to drive the light emitting devices ED-1, ED-2, and ED-3 of the display device layer DP-ED.

Each of the light emitting devices ED-1, ED-2, and ED-3 may have a structure of a light emitting device ED of an embodiment according to FIGS. 3 to 6, which will be described later. Each of the light emitting devices ED-1, ED-2 and ED-3 may include a first electrode EL1, a hole transport region HTR, one of emission layers EML-R, EML-G and EML-B, respectively, an electron transport region ETR, and a second electrode EL2.

FIG. 2 illustrates an embodiment in which the emission layers EML-R, EML-G, and EML-B of the light emitting devices ED-1, ED-2, and ED-3 in the openings OH defined in the pixel defining film PDL, and the hole transport region HTR, the electron transport region ETR, and the second electrode EL2 are provided as a common layer in the entire light emitting devices ED-1, ED-2, and ED-3. However, embodiments of the present disclosure are not limited thereto, and unlike the feature illustrated in FIG. 2, the hole transport region HTR and the electron transport region ETR in an embodiment may be provided by being patterned inside the opening hole OH defined in the pixel defining film PDL. For example, the hole transport region HTR, the emission layers EML-R, EML-G, and EML-B, and the electron transport region ETR in an embodiment may be provided by being patterned in an inkjet printing method.

The encapsulation layer TFE may cover the light emitting devices ED-1, ED-2 and ED-3. The encapsulation layer TFE may seal the display device layer DP-ED. The encapsulation layer TFE may be a thin film encapsulation layer. The encapsulation layer TFE may be formed by laminating one layer or a plurality of layers. The encapsulation layer TFE includes at least one insulation layer. The encapsulation layer TFE according to an embodiment may include at least one inorganic film (hereinafter, an encapsulation-inorganic film). The encapsulation layer TFE according to an embodiment may also include at least one organic film (hereinafter, an encapsulation-organic film) and at least one encapsulation-inorganic film.

The encapsulation-inorganic film may protect the display device layer DP-ED from moisture/oxygen, and the encapsulation-organic film may protect the display device layer DP-ED from foreign substances (such as dust particles). The encapsulation-inorganic film may include silicon nitride, silicon oxynitride, silicon oxide, titanium oxide, aluminum oxide, and/or the like, but embodiments of the present disclosure are not particularly limited thereto. The encapsulation-organic film may include an acrylic-based compound, an epoxy-based compound, and/or the like. The encapsulation-organic film may include a photopolymerizable organic material, but embodiments of the present disclosure are not particularly limited thereto.

The encapsulation layer TFE may be disposed on the second electrode EL2 and may be disposed filling the opening hole OH.

The upper base layer BL may be a member which provides a base surface on which the optical layer PP, or the like is disposed. The upper base layer BL may be a glass substrate, a metal substrate, a plastic substrate, etc. However, embodiments of the present disclosure are not limited thereto, and the upper base layer BL may be an inorganic layer, an organic layer, or a composite material layer. In an embodiment, the upper base layer BL may be omitted. When the upper base layer BL is omitted, the optical layer PP may be provided directly on the encapsulation layer TFE.

Referring to FIGS. 1 and 2, the display apparatus DD may include a non-light emitting region NPXA and light emitting regions PXA-R, PXA-G and PXA-B. The light emitting regions PXA-R, PXA-G and PXA-B may each be a region to emit light generated from the light emitting devices ED-1, ED-2 and ED-3, respectively. The light emitting regions PXA-R, PXA-G, and PXA-B may be spaced apart from each other in a plane.

Each of the light emitting regions PXA-R, PXA-G, and PXA-B may be divided or separated by the pixel defining film PDL. The non-light emitting regions NPXA may be regions between the adjacent light emitting regions PXA-R, PXA-G, and PXA-B, which correspond to portions of the pixel defining film PDL. In some embodiments, each of the light emitting regions PXA-R, PXA-G, and PXA-B may correspond to a pixel. The pixel defining film PDL may separate the light emitting devices ED-1, ED-2, and ED-3. The emission layers EML-R, EML-G and EML-B of the light emitting devices ED-1, ED-2 and ED-3 may be disposed in openings OH defined by the pixel defining film PDL and separated from each other.

The light emitting regions PXA-R, PXA-G and PXA-B may be divided into a plurality of groups according to the color of light generated by the plurality of light emitting devices ED-1, ED-2 and ED-3. In the display apparatus DD of an embodiment shown in FIGS. 1 and 2, three light emitting regions PXA-R, PXA-G, and PXA-B, which may be to respectively emit red light, green light, and blue light, are illustrated. For example, the display apparatus DD of an embodiment may include the red light emitting region PXA-R, the green light emitting region PXA-G, and the blue light emitting region PXA-B, which are different.

In the display apparatus DD according to an embodiment, the plurality of light emitting devices ED-1, ED-2 and ED-3 may be to emit light in different wavelength regions. For example, in an embodiment, the display apparatus DD may include the first light emitting device ED-1 to emit red light, the second light emitting device ED-2 to emit green light, and the third light emitting device ED-3 to emit blue light. For example, the red light emitting region PXA-R, the green light emitting region PXA-G, and the blue light emitting region PXA-B of the display apparatus DD may correspond to the first light emitting device ED-1, the second light emitting device ED-2, and the third light emitting device ED-3, respectively.

However, embodiments of the present disclosure are not limited thereto, and the first to the third light emitting devices ED-1, ED-2, and ED-3 may be to emit light in the same wavelength range, or at least one light emitting device may be to emit light in a wavelength range different from the others. For example, the first to third light emitting devices ED-1, ED-2, and ED-3 may all be to emit blue light.

The light emitting regions PXA-R, PXA-G, and PXA-B in the display apparatus DD according to an embodiment may be arranged in a stripe form. Referring to FIG. 1, the plurality of red light emitting regions PXA-R, the plurality of green light emitting regions PXA-G, and the plurality of blue light emitting regions PXA-B may each be arranged along a second directional axis DR2. The red light emitting region PXA-R, the green light emitting region PXA-G, and the blue light emitting region PXA-B may be alternately arranged in this order along a first directional axis DR1.

FIGS. 1 and 2 illustrate that all the light emitting regions PXA-R, PXA-G, and PXA-B have similar areas, but embodiments of the present disclosure are not limited thereto, and the light emitting regions PXA-R, PXA-G, and PXA-B may have different areas from each other according to a wavelength range of the emitted light. Here, the areas of the light emitting regions PXA-R, PXA-G, and PXA-B may be areas when viewed in a plane defined by the first directional axis DR1 and the second directional axis DR2.

In some embodiments, the arrangement of the light emitting regions PXA-R, PXA-G, and PXA-B is not limited to the feature illustrated in FIG. 1, and the order in which the red light emitting region PXA-R, the green light emitting region PXA-G, and the blue light emitting region PXA-B are arranged may be variously combined and modified according to the desired characteristics and display quality in the display apparatus DD. For example, the arrangement form of the light emitting regions PXA-R, PXA-G, and PXA-B may be a PENTILE® arrangement form or a diamond arrangement form.

In some embodiments, the areas of the light emitting regions PXA-R, PXA-G, and PXA-B may be different from each other. For example, in an embodiment, the area of the green light emitting region PXA-G may be smaller than that of the blue light emitting region PXA-B, but embodiments of the present disclosure are not limited thereto.

FIGS. 3 to 6 are cross-sectional views schematically illustrating organic electroluminescence devices according to embodiments of the present disclosure. Referring to FIGS. 3 to 6, in each of light emitting devices ED of embodiments, a first electrode EL1 and a second electrode EL2 are disposed facing each other, and a plurality of organic layers may be disposed between the first electrode EL1 and the second electrode EL2. The plurality of organic layers may include a hole transport region HTR, an emission layer EML, and an electron transport region ETR. For example, each of the light emitting devices ED according to embodiments may include the first electrode EL1, the hole transport region HTR, the emission layer EML, the electron transport region ETR, and the second electrode EL2, which are sequentially stacked. A capping layer CPL may be further disposed on the second electrode EL2.

Each of the light emitting devices ED of embodiments may include an amine compound of an embodiment described in at least one organic layer among the plurality of organic layers disposed between the first electrode EL1 and the second electrode EL2. For example, each of the light emitting devices ED of embodiments may include an amine compound of an embodiment in the hole transfer region HTR disposed between the first electrode EL1 and the second electrode EL2. However, embodiments of the present disclosure are not limited thereto, and each of the light emitting devices ED of embodiments may include an amine compound according to an embodiment in at least one organic layer included in the hole transport region HTR and the electron transfer region ETR, which are among the plurality of organic layers disposed between the first electrode EL1 and the second electrode EL2, or may include an amine compound according to an embodiment in the capping layer CPL disposed on the second electrode EL2.

Figure 3:
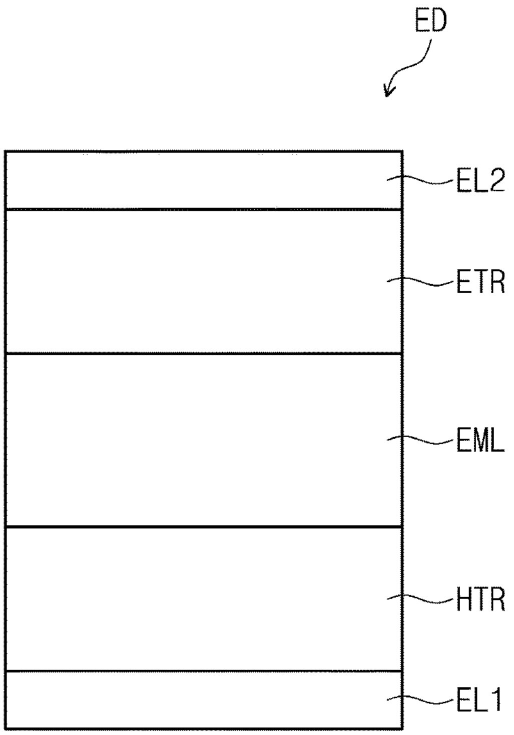
FIG. 3 is a cross-sectional view schematically illustrating an organic electroluminescence device according to an embodiment of the present disclosure.
Figure 4:
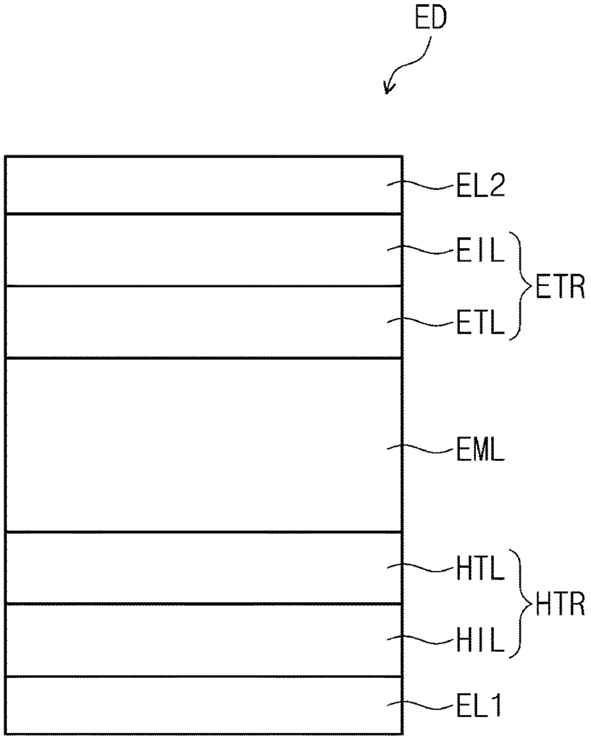
FIG. 4 is a cross-sectional view schematically illustrating an organic electroluminescence device according to an embodiment of the present disclosure.
Figure 5:
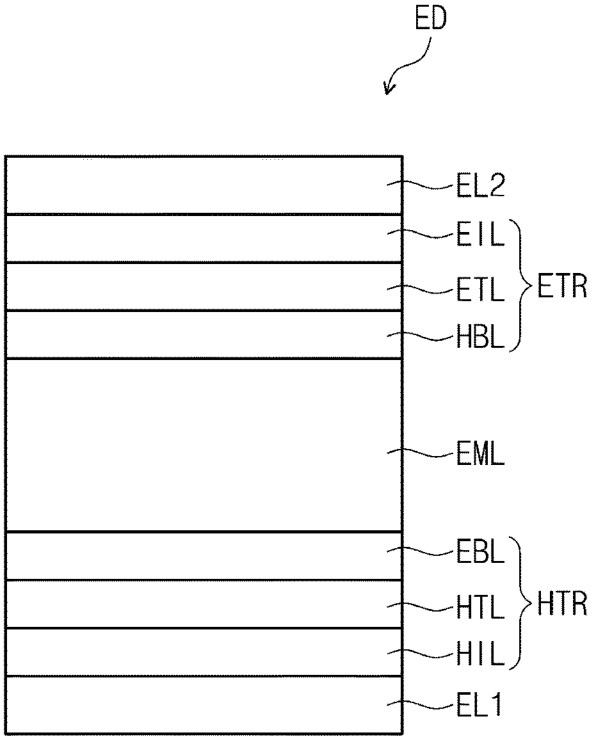
FIG. 5 is a cross-sectional view schematically illustrating an organic electroluminescence device according to an embodiment of the present disclosure.
Figure 6:
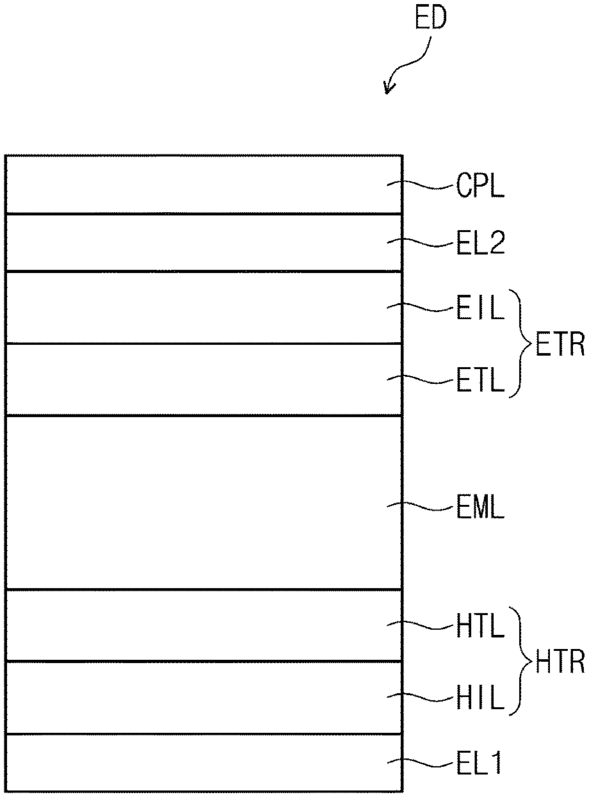
FIG. 6 is a cross-sectional view schematically illustrating an organic electroluminescence device according to an embodiment of the present disclosure.

Compared to FIG. 3, FIG. 4 illustrates a cross-sectional view of a light emitting device ED of an embodiment, in which a hole transport region HTR includes a hole injection layer HIL and a hole transport layer HTL, and an electron transport region ETR includes an electron injection layer EIL and an electron transport layer ETL. Compared to FIG. 3, FIG. 5 illustrates a cross-sectional view of a light emitting device ED of an embodiment, in which a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. Compared to FIG. 4, FIG. 6 illustrates a cross-sectional view of a light emitting device ED of an embodiment including a capping layer CPL disposed on a second electrode EL2.

Hereinafter, in the description of the light emitting device ED of an embodiment, it is described that the light emitting device ED includes an amine compound according to an embodiment in the hole transport region HTR, but embodiments of the present disclosure are not limited thereto, and an amine compound according to an embodiment may be included in the emission layer EML, and/or the electron transport region ETR.

The first electrode EL1 has conductivity. The first electrode EL1 may be formed of a metal alloy and/or a conductive compound. The first electrode EL1 may be an anode or a cathode. However, embodiments of the present disclosure are not limited thereto. In some embodiments, the first electrode EL1 may be a pixel electrode. The first electrode EL1 may be a transmissive electrode, a transflective electrode, or a reflective electrode. When the first electrode EL1 is a transmissive electrode, the first electrode EL1 may include a transparent metal oxide (such as indium tin oxide (ITO), indium zinc oxide (IZO), zinc oxide (ZnO), and/or indium tin zinc oxide (ITZO)). When the first electrode EL1 is a transflective electrode or a reflective electrode, the first electrode EL1 may include silver (Ag), magnesium (Mg), copper (Cu), aluminum (Al), platinum (Pt), palladium (Pd), gold (Au), nickel (Ni), neodymium (Nd), iridium (Ir), chromium (Cr), lithium (Li), calcium (Ca), LiF/Ca, LiF/Al, molybdenum (Mo), titanium (Ti), tungsten (W), indium (In), zinc (Zn), and/or tin (Sn), a compound thereof, a mixture thereof (e.g., a mixture of Ag and Mg), or at least one oxide thereof. The second electrode EL1 may have a multilayer structure including a reflective film or a transflective film formed of the above-described materials, and a transparent conductive film formed of ITO, IZO, ZnO, ITZO, etc. For example, the first electrode EL1 may have a three-layer structure of ITO/Ag/ITO, but embodiments of the present disclosure are not limited thereto. The thickness of the first electrode EL1 may be about 700 Å to about 10,000 Å. For example, the thickness of the first electrode EL1 may be about 1,000 Å to about 3,000 Å.

The hole transport region HTR is provided on the first electrode EL1. The hole transport region HTR may include at least one of the hole injection layer HIL, the hole transport layer HTL, a hole buffer layer, an emission auxiliary layer, or the electron blocking layer EBL. The thickness of the hole transport region HTR may be, for example, about 50 Å to about 15,000 Å.

The hole transport region HTR may have a single layer formed of a single material, a single layer formed of a plurality of different materials, or a multilayer structure including a plurality of layers formed of a plurality of different materials.

For example, the hole transport region HTR may have a single layer structure of the hole injection layer HIL or the hole transport layer HTL, or may have a single layer structure formed of a hole injection material and a hole transport material. In some embodiments, the hole transport region HTR may have a single layer structure formed of a plurality of different materials, or a structure in which a hole injection layer HIL/hole transport layer HTL, a hole injection layer HIL/hole transport layer HTL/hole buffer layer, a hole injection layer HIL/hole buffer layer, a hole transport layer HTL/hole buffer layer, or a hole injection layer HIL/hole transport layer HTL/electron blocking layer EBL are stacked in order from the first electrode EL1, but embodiments of the present disclosure are not limited thereto.

The hole transport region HTR may be formed utilizing one or more suitable methods (such as a vacuum deposition method, a spin coating method, a cast method, a Langmuir-Blodgett (LB) method, an inkjet printing method, a laser printing method, and/or a laser induced thermal imaging (LITI) method).

The hole transport region HTR in the light emitting device ED of an embodiment may include an amine compound of an embodiment.

The amine compound of an embodiment includes a spirofluorene-indene group as a substituent. For example, the amine compound of an embodiment includes an amine group, and a spirofluorene-indene group substituted at the amine group. The spirofluorene-indene group include a fluorene group and an indene group, and may be a substituent in which the 9-carbon position of the fluorene group and the 2-carbon position of the indene group are the same carbon, and thereby form a spiro structure with that carbon as a spiro center. For example, the spirofluorene-indene group may have a bicyclic structure including the fluorene group and the indene group. The amine group may be connected (bonded) to one benzene ring of the fluorene group moiety included in the spirofluorene-indene group. The spirofluorene-indene group included in the amine compound may be directly bonded to the amine group, or bonded via a linker. In an embodiment, the linker between the spirofluorene-indene group and the amine group may be a substituted or unsubstituted arylene group having 6 to 30 ring-forming carbon atoms, or a substituted or unsubstituted heteroarylene group having 2 to 30 ring-forming carbon atoms.

The amine compound of an embodiment may be a monoamine compound. For example, the amine compound may include one amine group in the compound structure.

The amine compound of an embodiment may be represented by Formula 1:

Formula 1

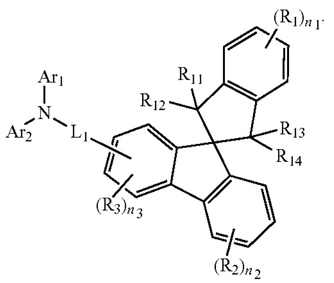

In Formula 1, $Ar_1$ and $Ar_2$ may each independently be a substituted or unsubstituted aryl group having 6 to 30 ring-forming carbon atoms, or a substituted or unsubstituted heteroaryl group having 2 to 30 ring-forming carbon atoms. In an embodiment, $Ar_1$ and $Ar_2$ may each independently be a substituted or unsubstituted phenyl group, a substituted or unsubstituted biphenyl group, a substituted or unsubstituted aryl group in which two or more rings are condensed, or a substituted or unsubstituted heteroaryl group in which two or more rings are condensed. $Ar_1$ and $Ar_2$ may each independently be a substituted or unsubstituted phenyl group, a substituted or unsubstituted biphenyl group, a substituted or unsubstituted naphthyl group, a substituted or unsubstituted fluorenyl group, a substituted or unsubstituted carbazole group, a substituted or unsubstituted dibenzofuran group, or a substituted or unsubstituted dibenzothiophene group. $Ar_1$ and $Ar_2$ may be different from each other.

$Ar_2$ may be a substituted or unsubstituted heteroaryl group in which two or more rings are condensed. $Ar_2$ may be a dibenzoheterole group including two benzene rings and a pentagonal ring containing a heteroatom. In some embodiments, $Ar_2$ may be a substituted or unsubstituted carbazole group. In some embodiments, $Ar_2$ may be a substituted or unsubstituted dibenzofuran group, or a substituted or unsubstituted dibenzothiophene group.

In Formula 1, $L_1$ may be a direct linkage, a substituted or unsubstituted arylene group having 6 to 30 ring-forming carbon atoms, or a substituted or unsubstituted heteroarylene group having 2 to 30 ring-forming carbon atoms. In an embodiment, $L_1$ may be a direct linkage, or a substituted or unsubstituted phenylene group. For example, $L_1$ may be a direct linkage, or an unsubstituted phenylene group.

In Formula 1, $R_1$ to $R_3$ may each independently be a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms. In Formula 1, the case where $R_1$ to $R_3$ each are bonded to an adjacent group to form a ring may be excluded. For example, in the amine compound represented by Formula 1, the spirofluorene-indene group moiety does not form or include an additional ring in addition to the fluorene group and indene group structure included in the spiro structure. In an embodiment, each of $R_1$ to $R_3$ may be a hydrogen atom.

In Formula 1, $R_{11}$ to $R_{14}$ may each independently be a hydrogen atom, a deuterium atom, a halogen atom, or a substituted or unsubstituted alkyl group having 1 to 20 carbon atoms. $R_{11}$ to $R_{14}$ may each independently be a substituent having a low steric hindrance. In an embodiment, each of $R_{11}$ to $R_{14}$ may be a hydrogen atom.

In Formula 1, $n_1$ and $n_2$ may each independently be an integer of 0 to 4, and $n_3$ may be an integer of 0 to 3. In Formula 1, when $n_1$ is 0, the amine compound of an embodiment may not be substituted with $R_1$. The case where $n_1$ is 4 and $R_1$'s are all hydrogen atoms in Formula 1 may be the same as the case where $n_1$ is 0 in Formula 1. In Formula 1, when $n_1$ is an integer of 2 or more, a plurality of $R_1$'s may be the same as each other or different from each other. In Formula 1, when $n_2$ is 0, the amine compound of an embodiment may not be substituted with $R_2$. The case where $n_2$ is 4 and $R_2$'s are all hydrogen atoms in Formula 1 may be the same as the case where $n_2$ is 0 in Formula 1. In Formula 1, when $n_2$ is an integer of 2 or more, a plurality of $R_2$'s may be the same as each other or different from each other. In Formula 1, when $n_3$ is 0, the amine compound of an embodiment may not be substituted with $R_3$. The case where $n_3$ is 3 and $R_3$'s are all hydrogen atoms in Formula 1 may be the same as the case where $n_3$ is 0 in Formula 1. In Formula 1, when $n_3$ is an integer of 2 or more, a plurality of $R_3$'s may be the same as each other or different from each other.

The amine compound of an embodiment includes the spirofluorene-indene group as a substituent connected to the amine (e.g., on the nitrogen atom). For example, the amine compound does not have a separately additional ring, and instead may include a substituent in which the fluorene group and the indene group form a spiro structure. The amine compound of an embodiment includes the spirofluorene-indene group as a substituent, and thus the compound structure is stabilized, whereby the ability of a hole transport between molecules may be improved. Therefore, the organic electroluminescence device including the amine compound of an embodiment as a hole transport material may have a long service life, in addition to high luminous efficiency, low driving voltage, and/or high brightness because the damage of materials caused by extra charges is protected.

The amine compound represented by Formula 1 may be represented by Formula 2-1 or Formula 2-2:

Formula 2-1

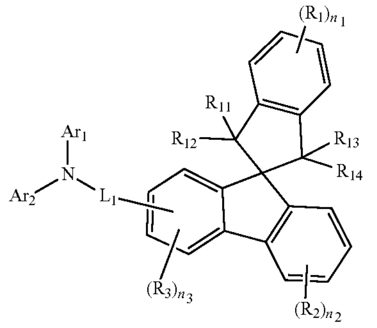

Formula 2-1

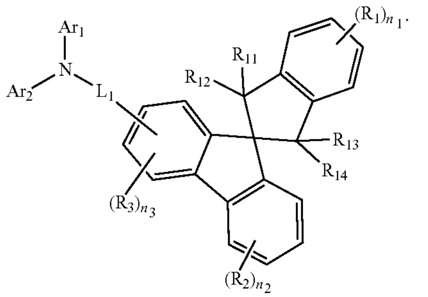

Formula 2-1 and Formula 2-2 are embodiments of Formula 1 in which the carbon position at which the spirofluorene-indene group moiety is connected, via $L_1$, to a center nitrogen atom of the amine compound, is specified.

As in Formula 2-1, the amine compound of an embodiment may be connected, via $L_1$, to the center nitrogen atom of the amine compound at the 2-carbon position of the fluorene group moiety of the spirofluorene-indene group moiety. In some embodiments, as in Formula 2-2, the amine compound of an embodiment may be connected, via $L_1$, to the center nitrogen atom of the amine compound at the 3-carbon position of the fluorene group moiety of the spirofluorene-indene group moiety.

In Formula 2-1 and Formula 2-2, the same described to $Ar_1$, $Ar_2$, $L_1$, $R_1$, $R_2$, $R_3$, $R_{11}$, $R_{12}$, $R_{13}$, $R_{14}$, $n_1$, $n_2$, and $n_3$ may be the same as described in connection with Formula 1.

The amine compound represented by Formula 1 may be represented by Formula 3:

Formula 3

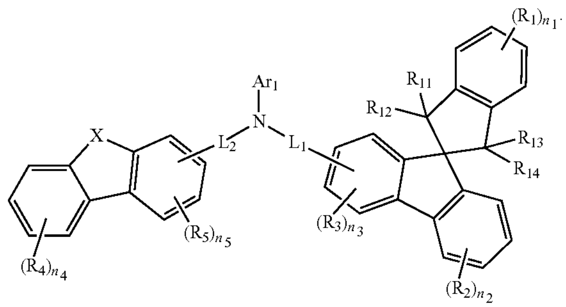

In Formula 3, X may be O, S or $NAr_3$. Formula 3 represents embodiments of Formula 1 in which the substituent represented by $Ar_2$ is a dibenzoheterole group (such as a carbazole group, a dibenzofuran group, and/or a dibenzothiophene group), and for example where the dibenzoheterole group is connected via a linker represented by $Ar_2$.

In Formula 3, $Ar_3$ may be a hydrogen atom, a substituted or unsubstituted aryl group having 6 to 30 ring-forming carbon atoms, or a substituted or unsubstituted heteroaryl group having 2 to 30 ring-forming carbon atoms. $Ar_3$ may be a substituted or unsubstituted phenyl group. For example, $Ar_3$ may be an unsubstituted phenyl group, or a phenyl group at which a halogen atom is substituted. $Ar_3$ may be a phenyl group at which a fluorine atom is substituted.

In Formula 3, $R_4$ and $R_5$ may each independently be a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms. In an embodiment, each of $R_4$ and $R_5$ may be a hydrogen atom.

In Formula 3, $n_4$ may be an integer of 0 to 4, and $n_5$ may be an integer of 0 to 3. In Formula 3, when $n_4$ is 0, the amine compound of an embodiment may not be substituted with $R_4$. The case where $n_4$ is 4 and $R_4$'s are all hydrogen atoms in Formula 3 may be the same as the case where $n_4$ is 0 in Formula 3. In Formula 3, when $n_4$ is an integer of 2 or more, a plurality of $R_4$'s may be the same as each other or different from each other. In Formula 3, when $n_5$ is 0, the amine compound of an embodiment may not be substituted with $R_5$. The case where $n_5$ is 3 and $R_5$'s are all hydrogen atoms in Formula 3 may be the same as the case where $n_5$ is 0 in Formula 3. In Formula 3, when $n_5$ is an integer of 2 or more, a plurality of $R_5$'s may be the same as each other or different from each other.

In Formula 3, $Ar_1$, $L_1$, $R_1$, $R_2$, $R_3$, $R_{11}$, $R_{12}$, $R_{13}$, $R_{14}$, $n_1$, $n_2$, and $n_3$ may be the same as described in connection with Formula 1.

The amine compound represented by Formula 3 may be represented by any one among Formula 4-1 to Formula 4-3:

Formula 4-1

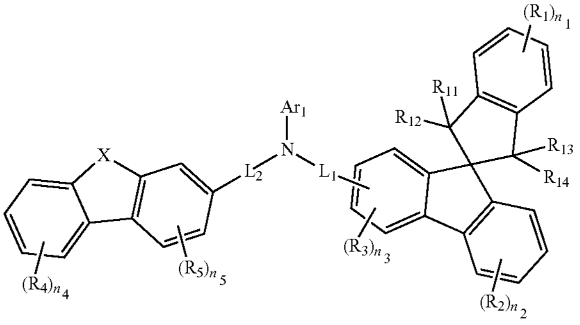

Formula 4-2

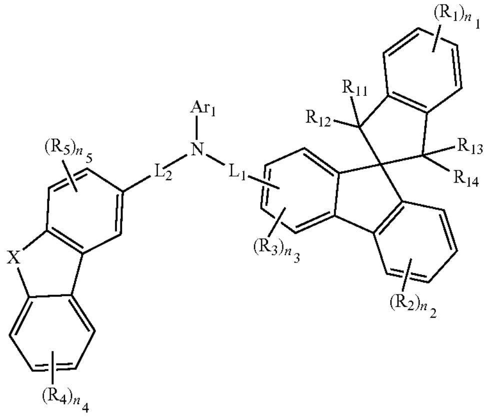

Formula 4-3

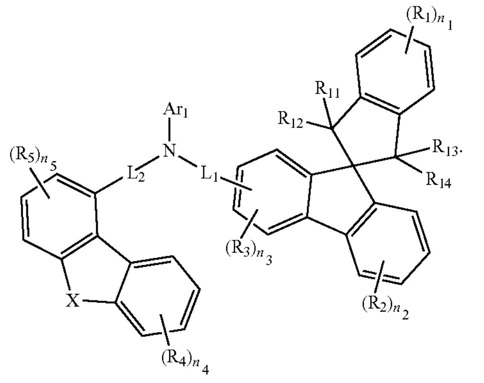

Formula 4-1 to Formula 4-3 are embodiments of Formula 3 in which the carbon position at which the dibenzoheterole group is connected, via $L_2$, to a center nitrogen atom of the amine compound, is specified.

As in Formula 4-1, the amine compound of an embodiment may be connected, via $L_2$, to the center nitrogen atom of the amine compound at the 2-carbon position of the dibenzoheterole group. As in Formula 4-2, the amine compound of an embodiment may be connected, via $L_2$, to the center nitrogen atom of the amine compound at the 3-carbon position of the dibenzoheterole group. As in Formula 4-3, the amine compound of an embodiment may be connected, via $L_2$, to the center nitrogen atom of the amine compound at the 4-carbon position of the dibenzoheterole group.

In Formula 4-1 to Formula 4-3, $Ar_1$, L, $L_1$, $L_2$, $R_1$, $R_2$, $R_3$, $R_4$, $R_5$, $R_{11}$, $R_{12}$, $R_{13}$, $R_{14}$, $n_1$, $n_2$, $n_3$, $n_4$, and $n_5$ may be the same as described in connection with Formula 1 and Formula 3.

The amine compound represented by Formula 3 may be represented by any one among Formula 5-1 to Formula 5-3:

Formula 5-1

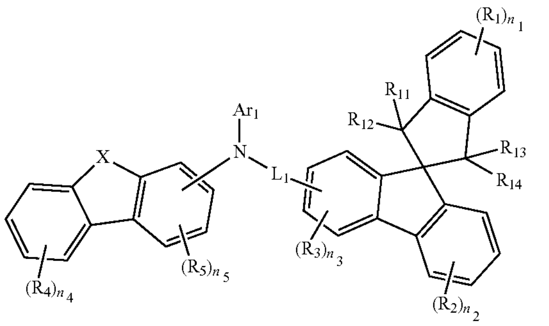

Formula 5-2

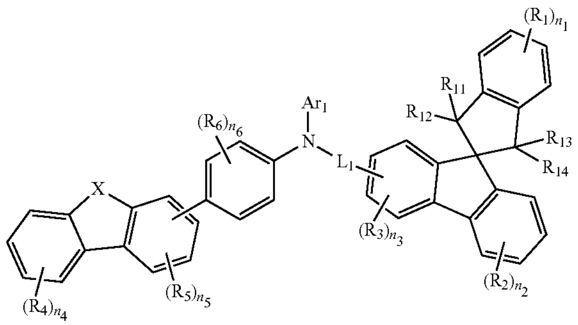

Formula 5-3

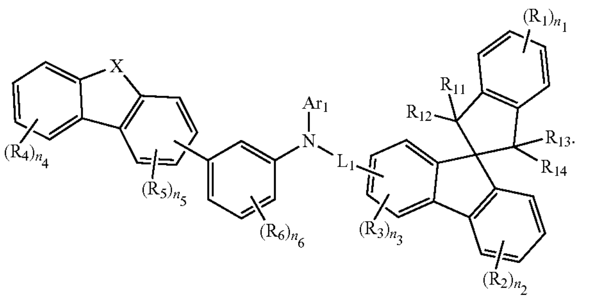

Formula 5-1 to Formula 5-3 are embodiments of Formula 3 in which $L_2$ is specified as a particular structure. Formula 5-1 is the case where in Formula 3, $L_2$ is a direct linkage. Formula 5-2 is the case where in Formula 3, $L_2$ is a p-phenylene group. Formula 5-3 is the case where in Formula 3, $L_2$ is a m-phenylene group.

In Formula 5-2 and Formula 5-3, $R_6$ may be a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms. In an embodiment, $R_6$ may be a hydrogen atom.

In Formula 5-2 and Formula 5-3, $n_6$ may be an integer of 0 to 4. In Formula 5-2 and Formula 5-3, when $n_6$ is 0, the amine compound of an embodiment may not be substituted with $R_6$. The case where $n_6$ is 4 and $R_6$'s are all hydrogen atoms in Formula 5-2 and Formula 5-3 may be the same as the case where $n_6$ is 0 in Formula 5-2 and Formula 5-3. In Formula 5-2 and Formula 5-3, when $n_6$ is an integer of 2 or more, a plurality of $R_6$'s may be the same as each other or different from each other.

In Formula 5-2 and Formula 5-3, $Ar_1$, X, $L_1$, $R_1$, $R_2$, $R_3$, $R_4$, $R_5$, $R_{11}$, $R_{12}$, $R_{13}$, $R_{14}$, $n_1$, $n_2$, $n_3$, $n_4$, and $n_5$ may be the same as described in connection with Formula 1 and Formula 3.

The amine compound may be any one of the compounds represented by Compound Group 1. The light emitting device ED of an embodiment may include at least one amine compound among the compounds represented by Compound Group 1 in the hole transport region HTR. The light emitting device ED of an embodiment may include at least one amine compound among the compounds represented by Compound Group 1 in the hole transport layer HTL.

Compound Group 1

1

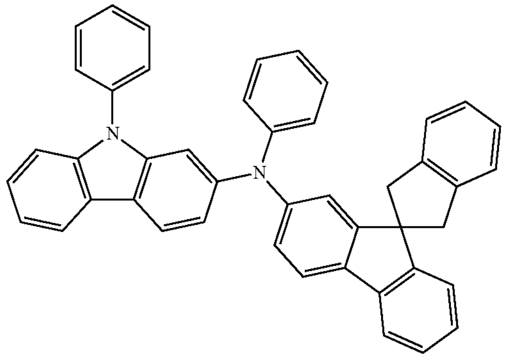

2

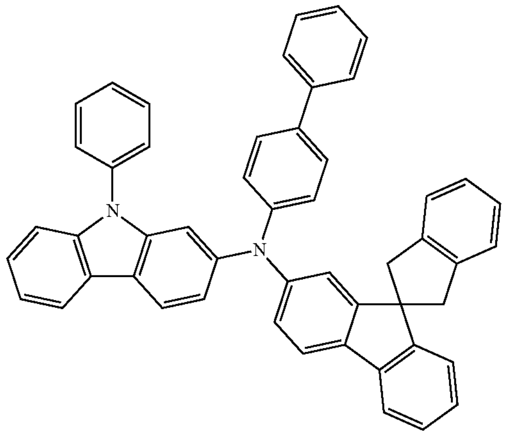

3

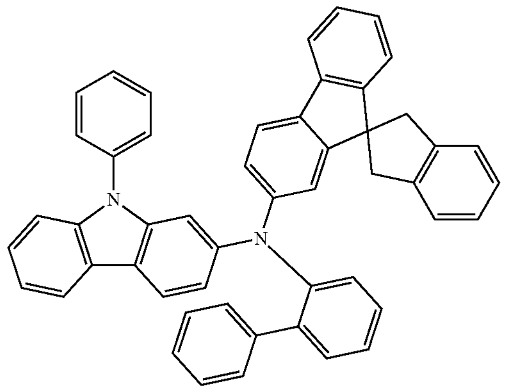

-continued
4
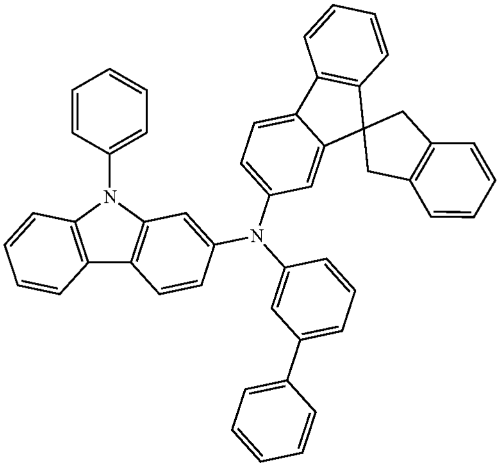
5
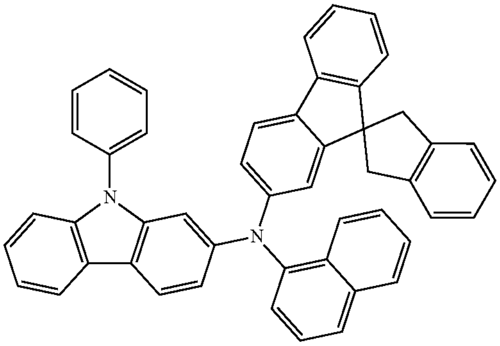
6
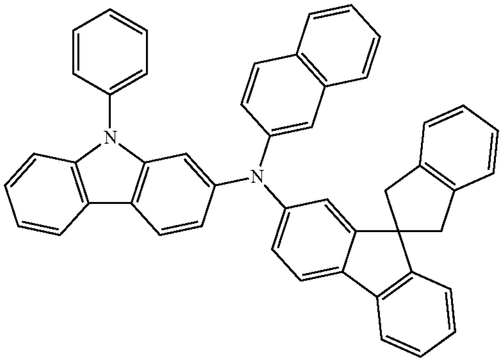
7
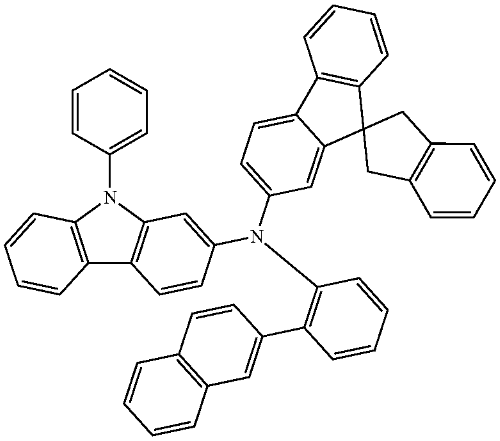
-continued
8
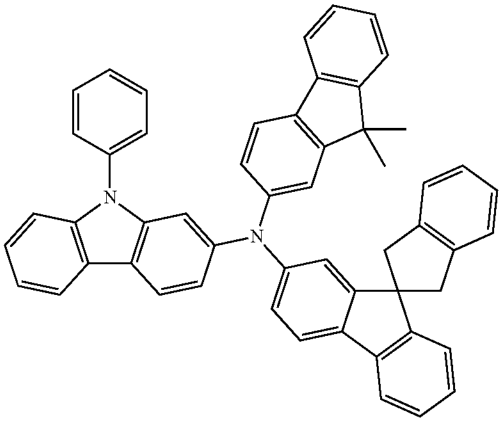
9
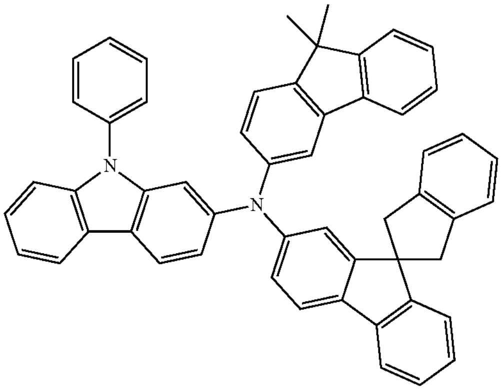
10
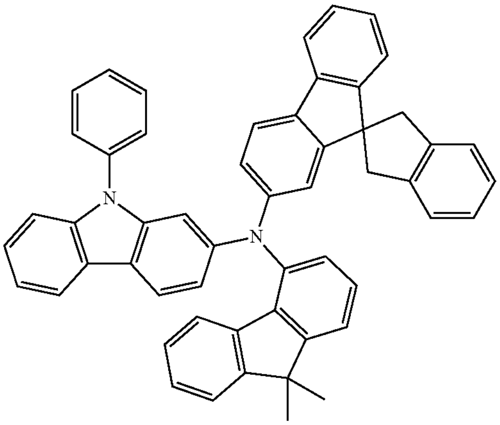

-continued
11
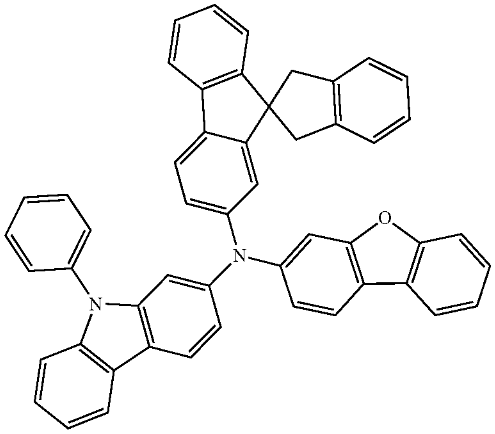
12
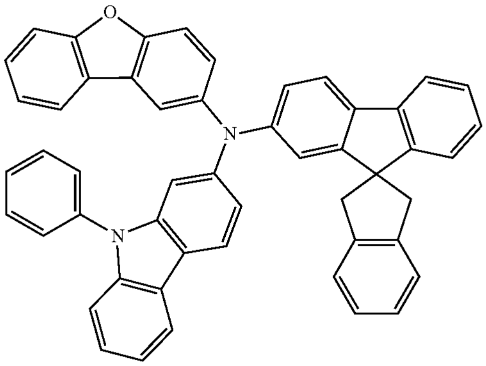
13
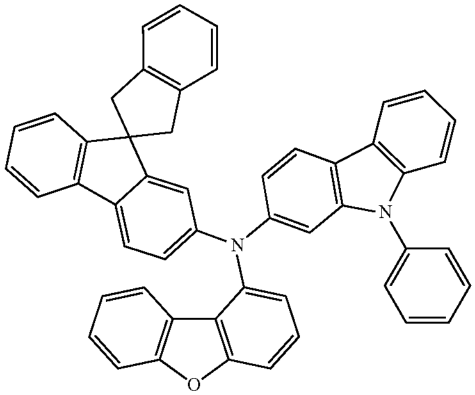
-continued
14
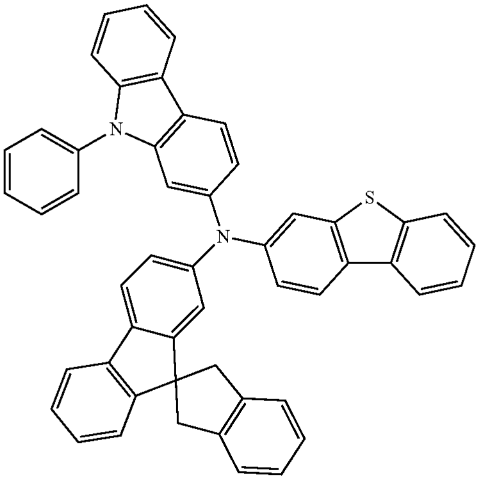
15
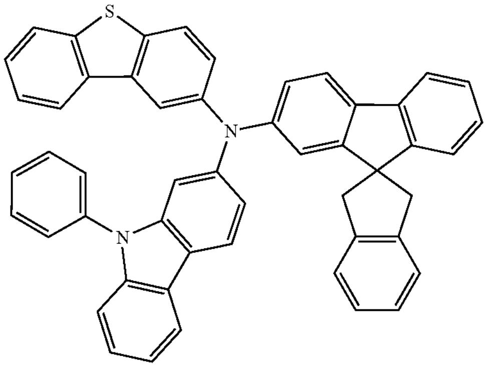
16
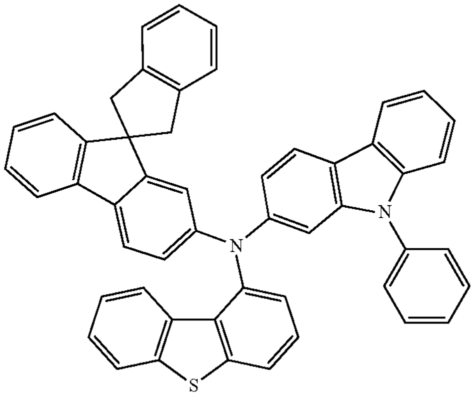

-continued
17
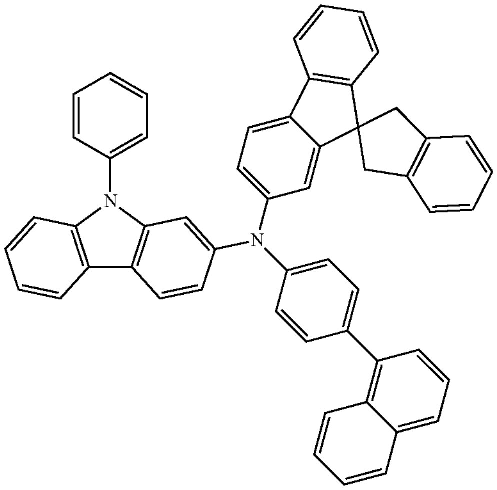
18
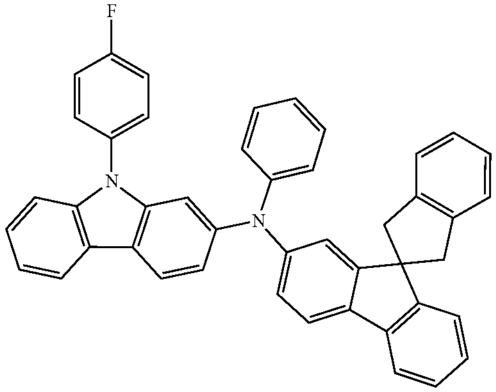
19
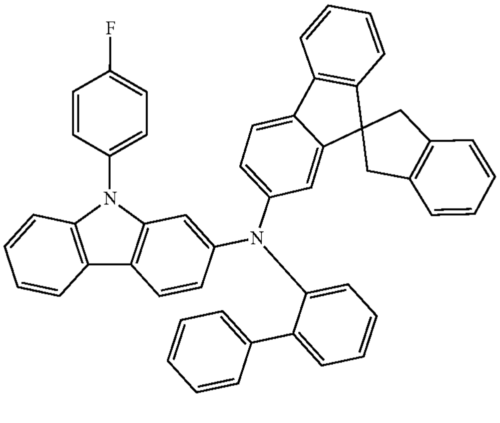
-continued
20
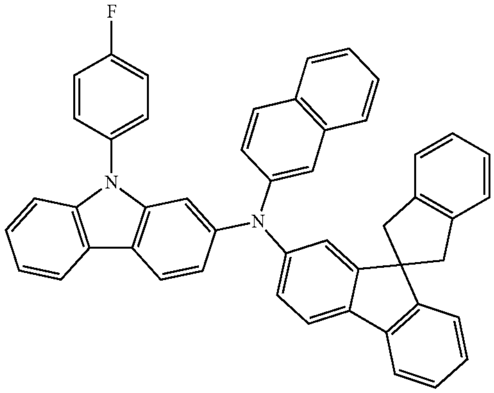
21
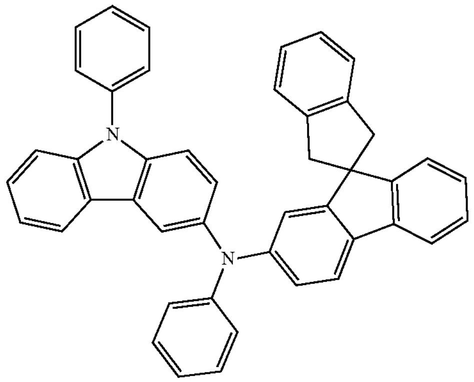
22
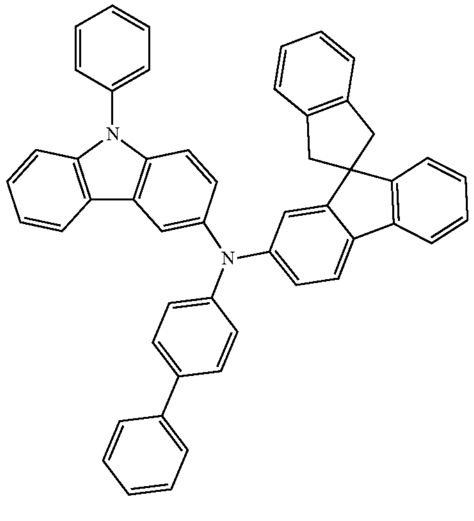

-continued
23
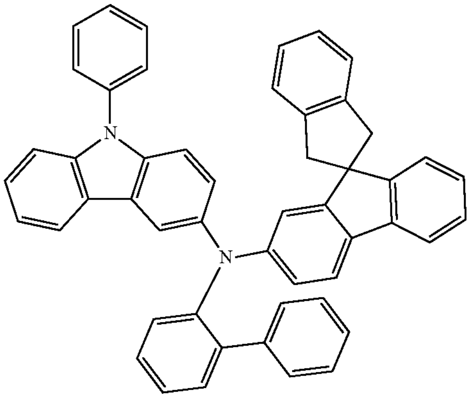
24
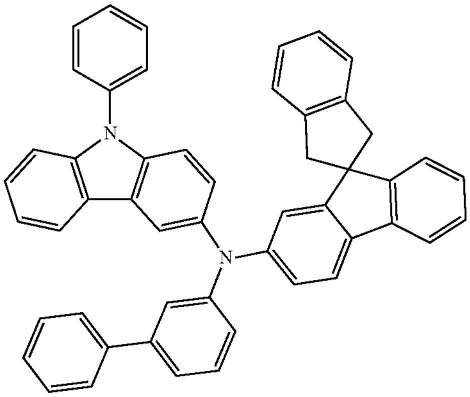
25
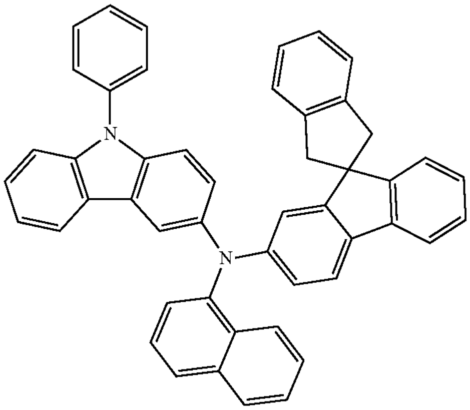
-continued
26
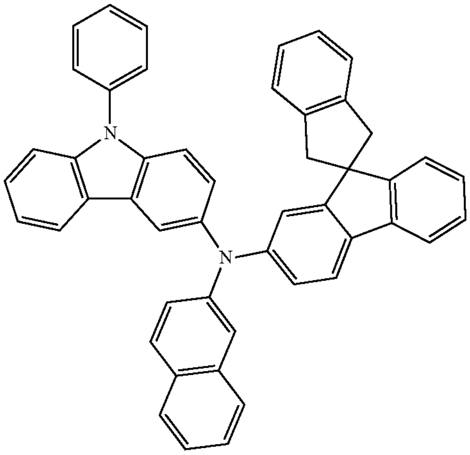
27
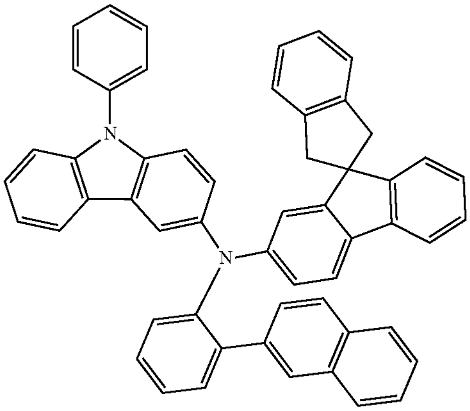
28
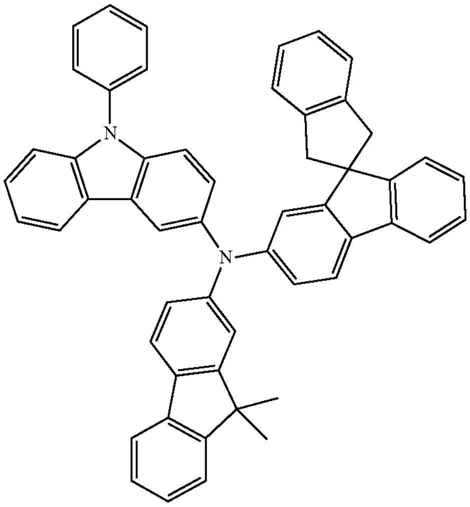

-continued
29
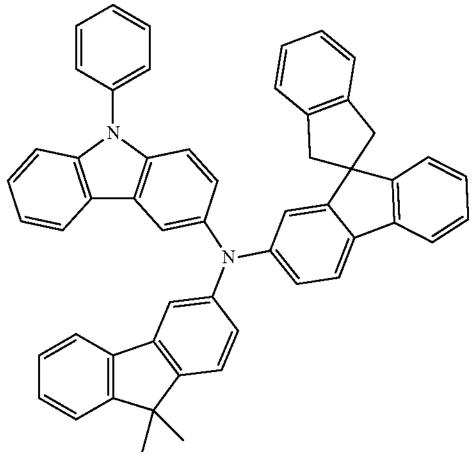
30
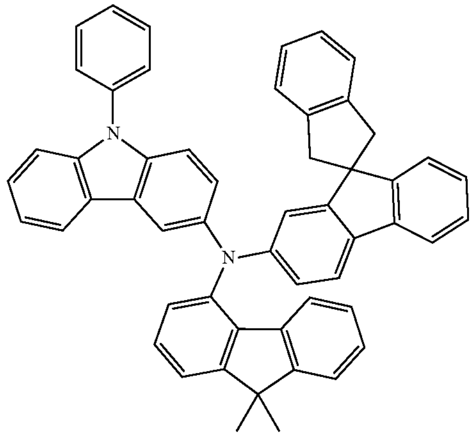
31
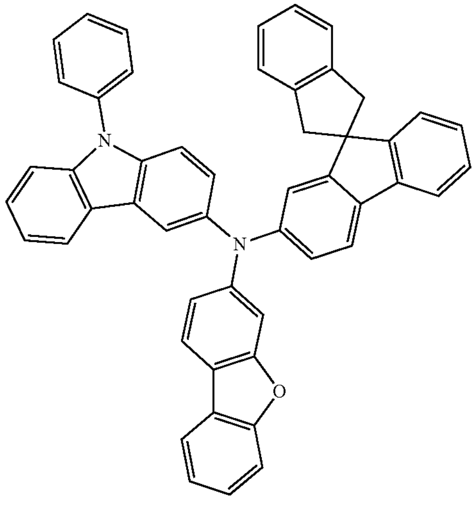
-continued
32
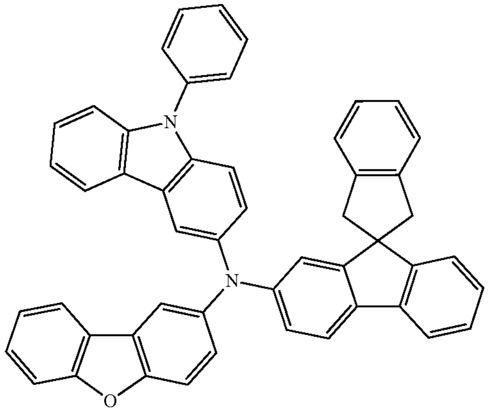
33
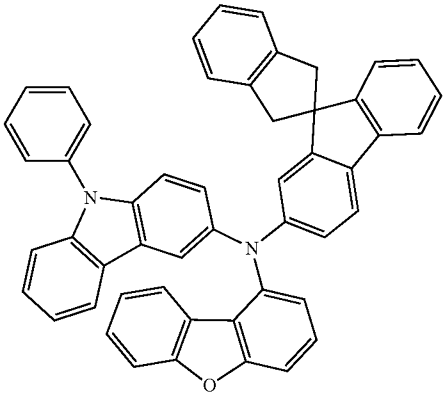
34
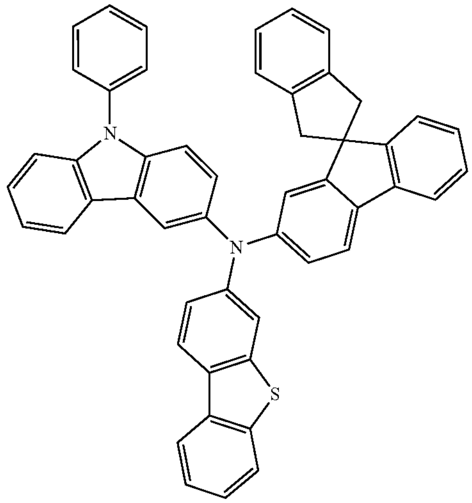

-continued
35
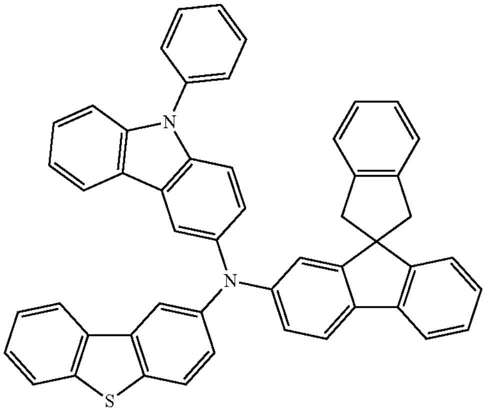
36
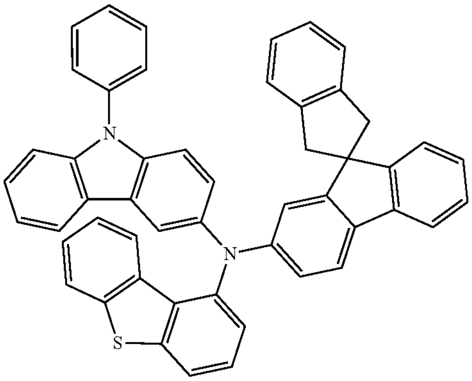
37
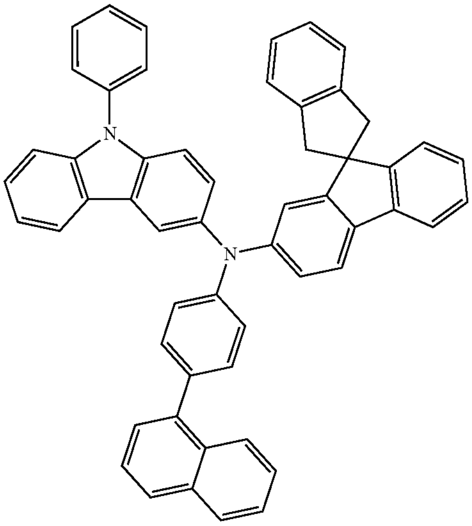
-continued
38
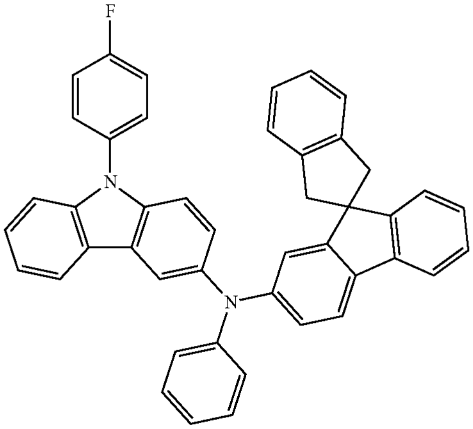
39
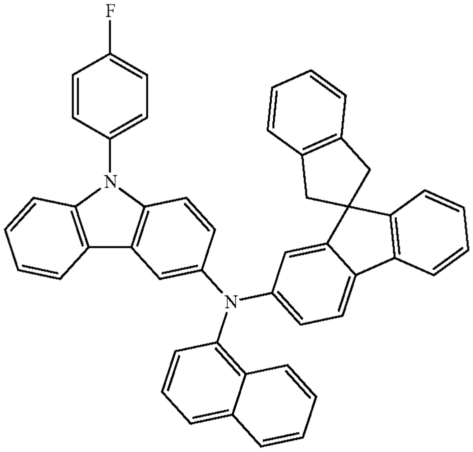
40
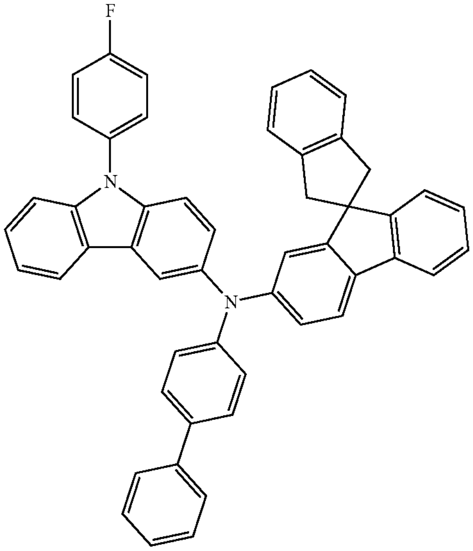

-continued
41
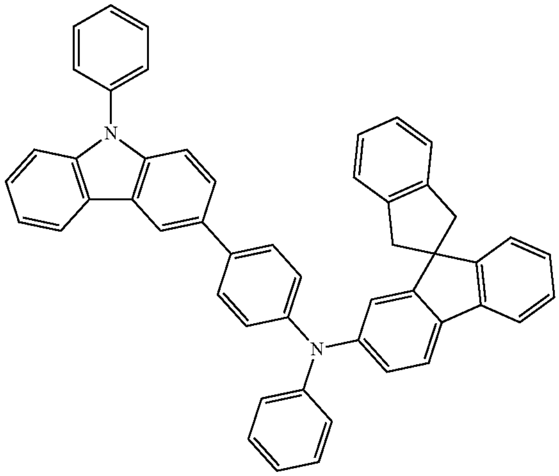
42
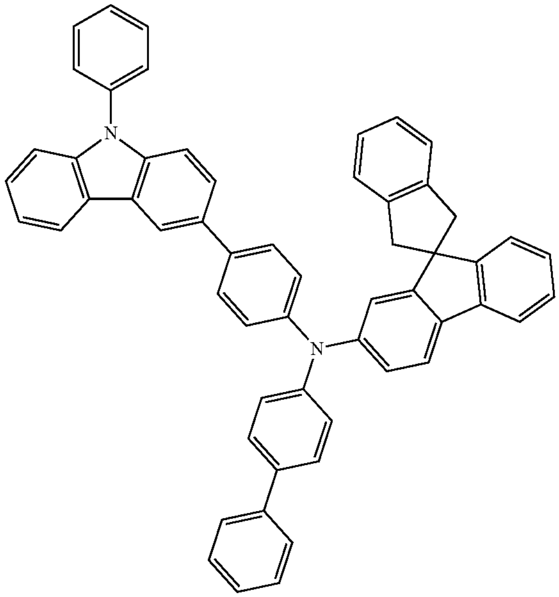
43
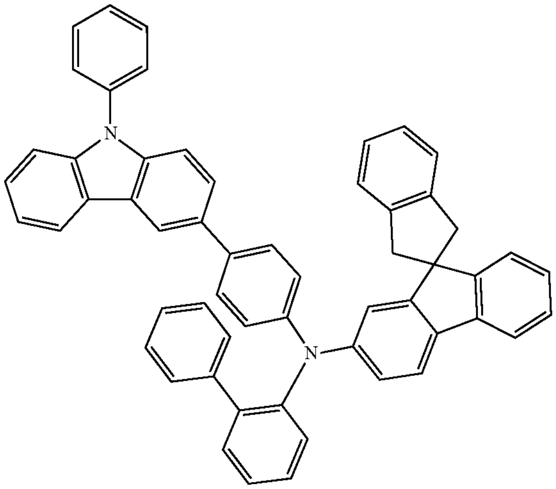
-continued
44
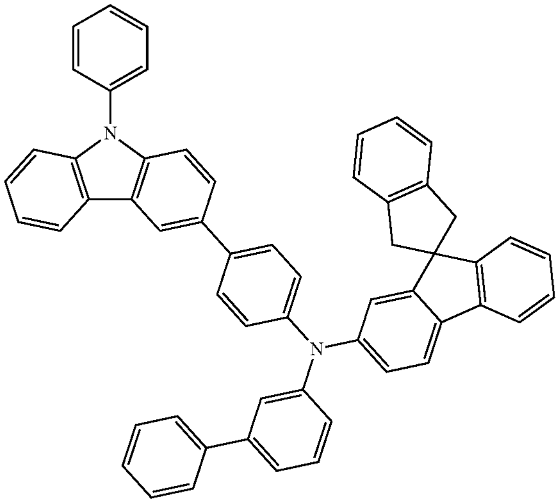
45
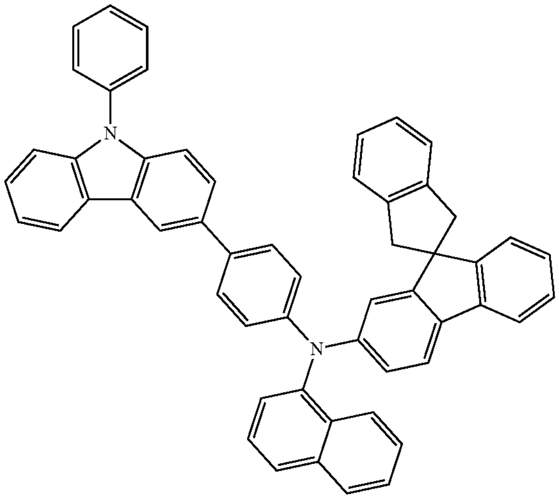
46
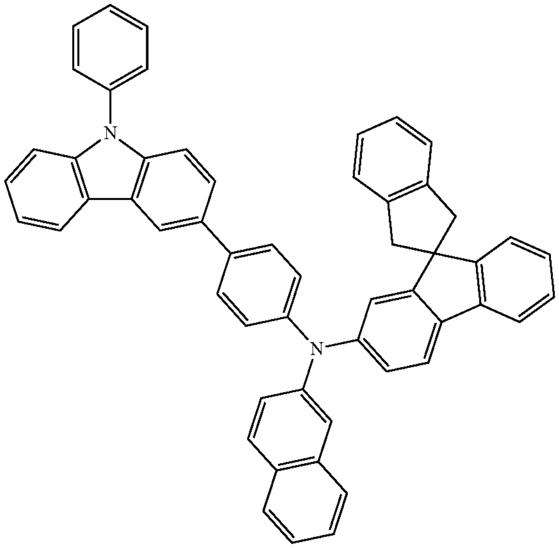

-continued
47
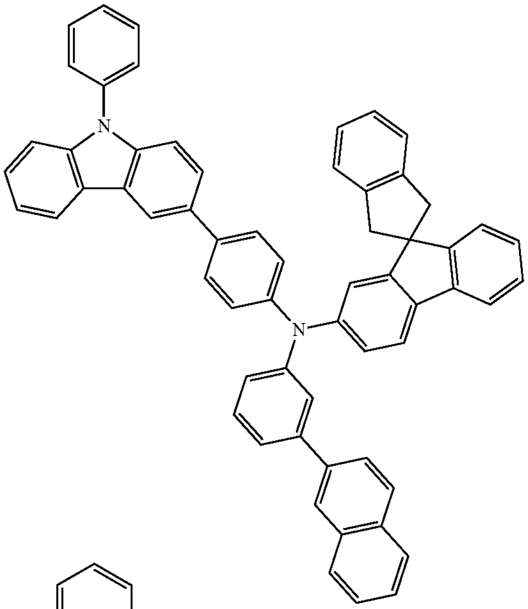
48
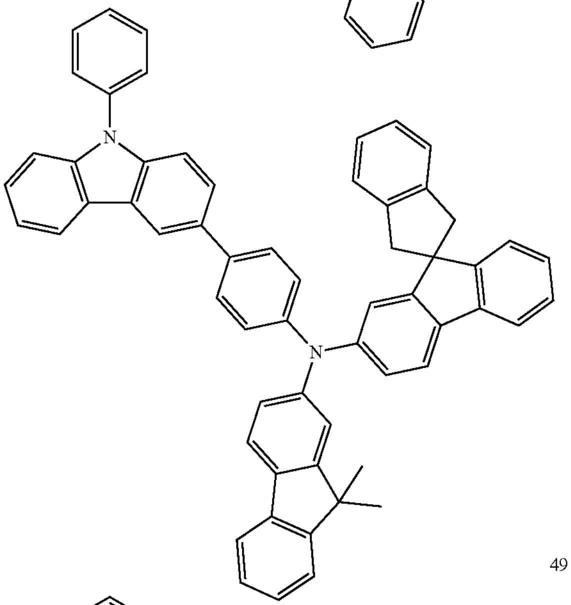
49
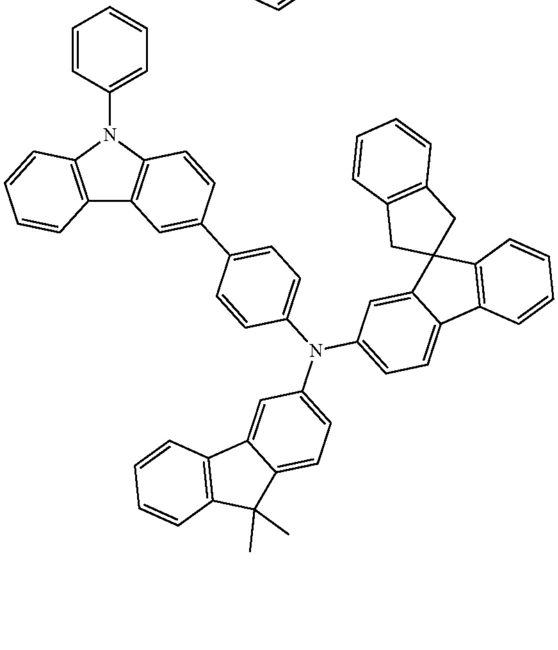
-continued
50
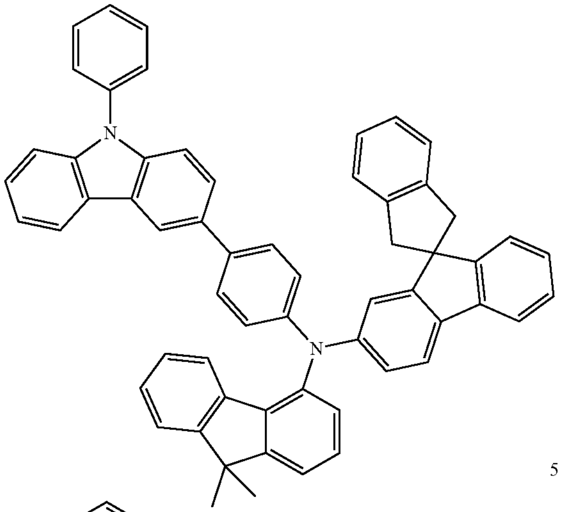
51
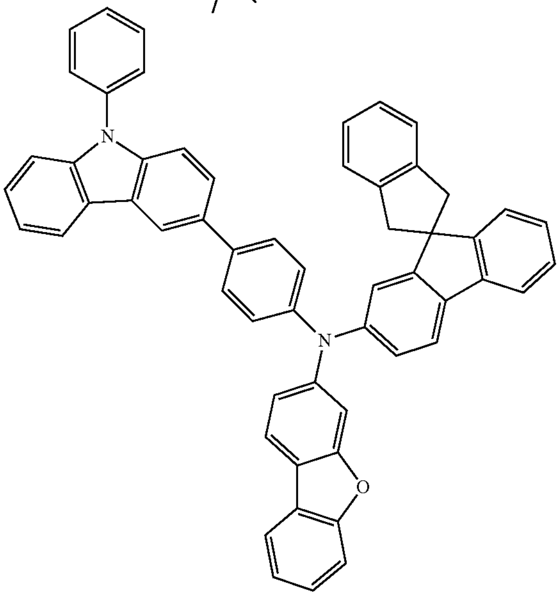
52
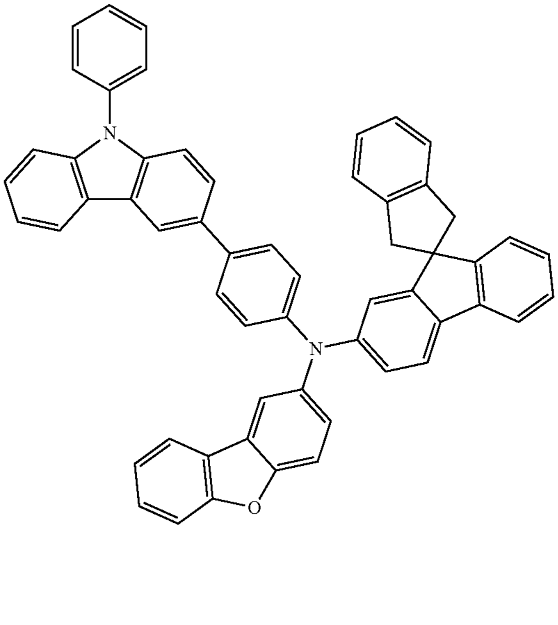

-continued
53
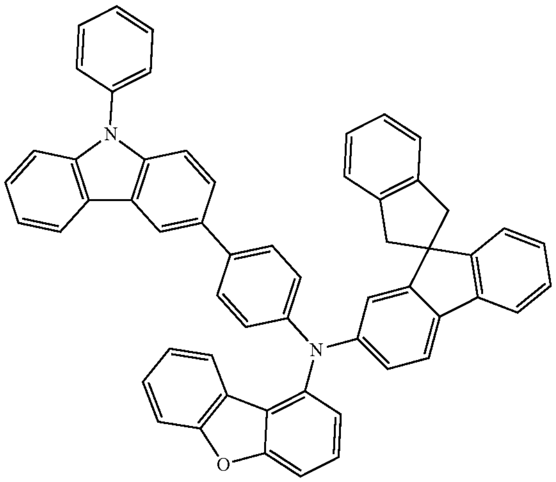
54
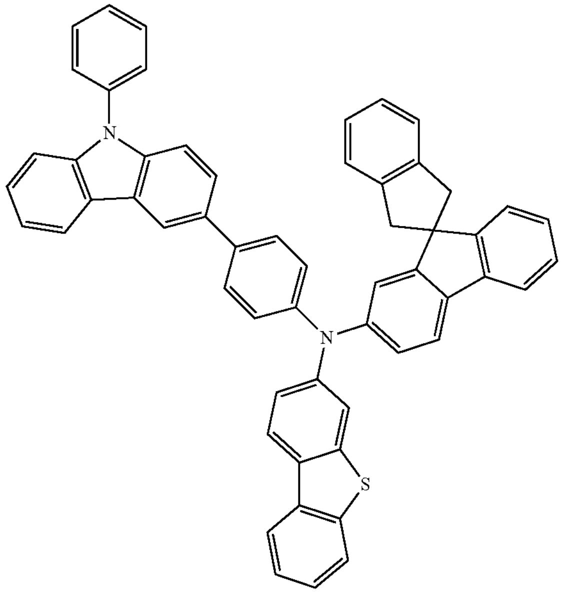
55
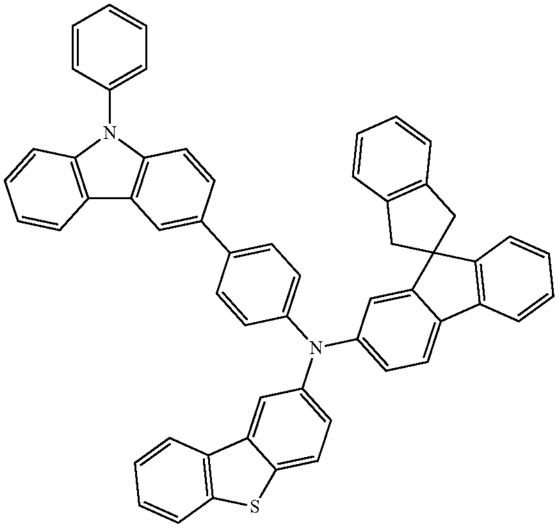
-continued
56
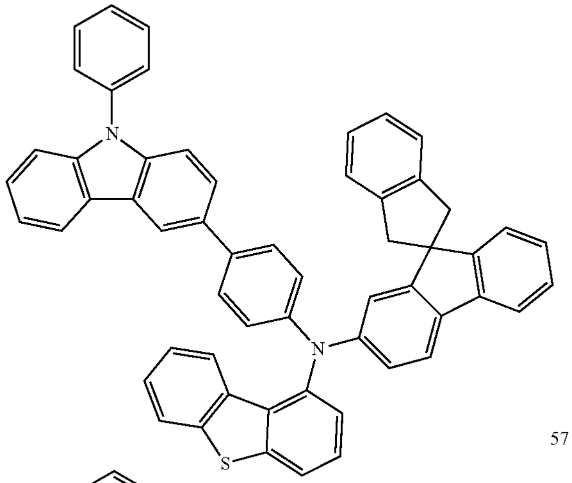
57
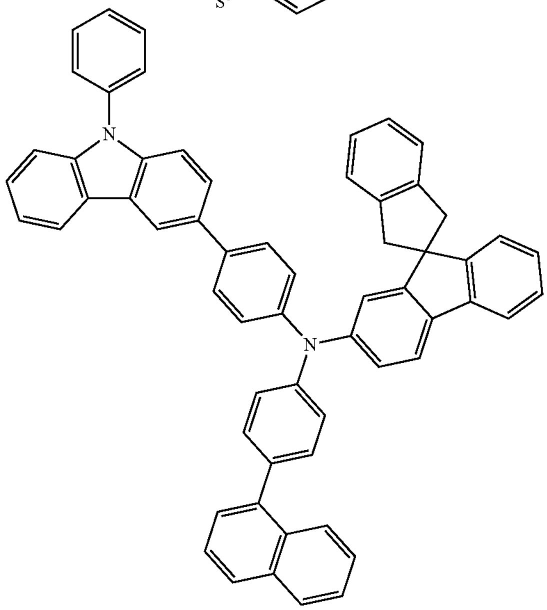
58
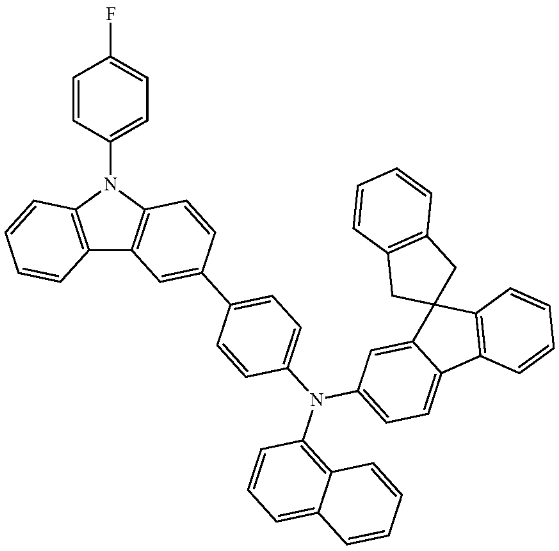

-continued
59
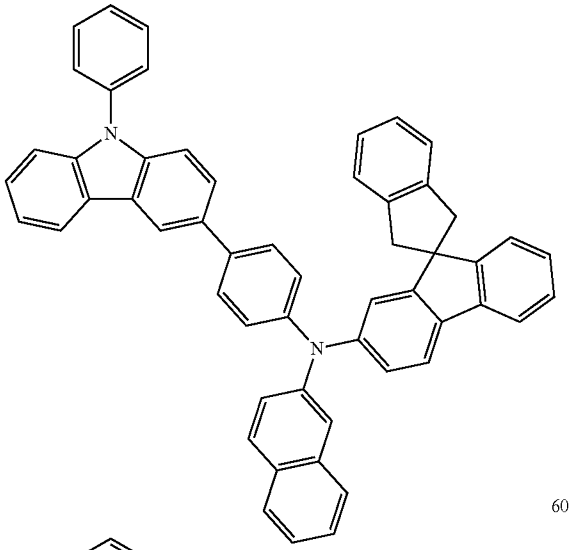
60
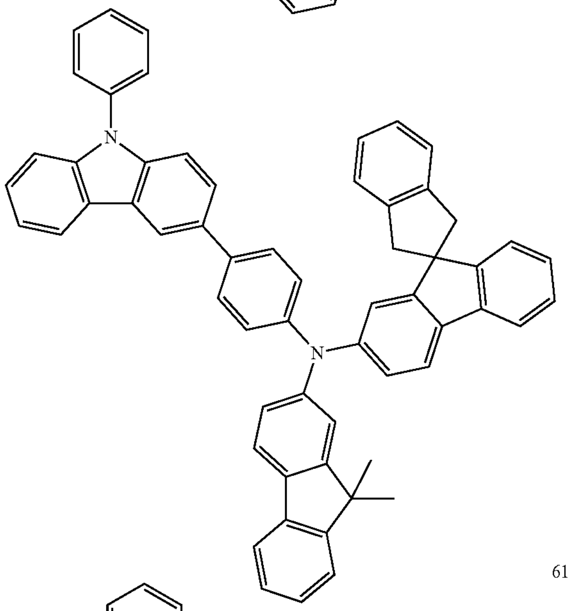
61
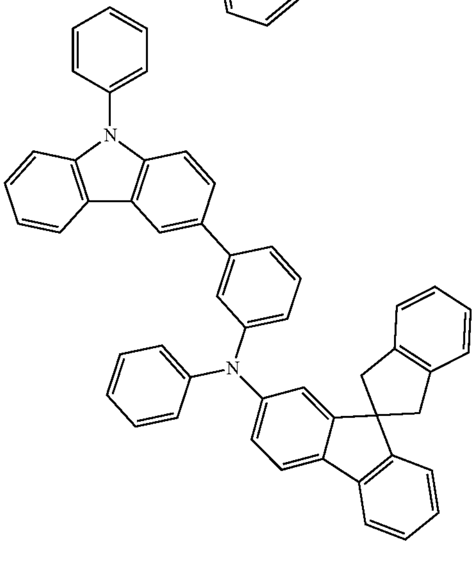
-continued
62
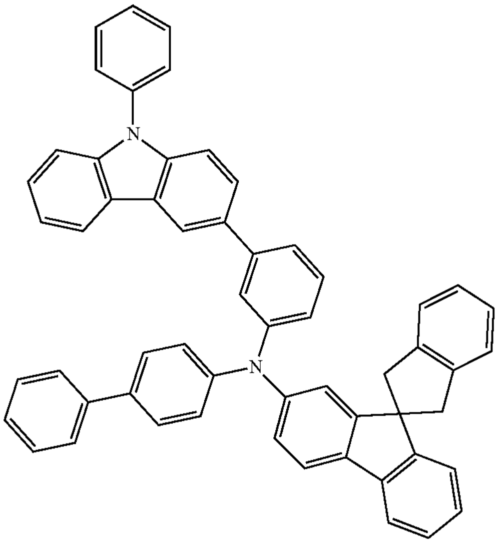
63
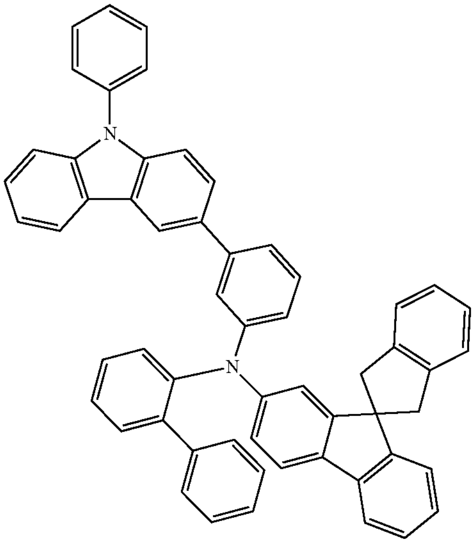

-continued
64
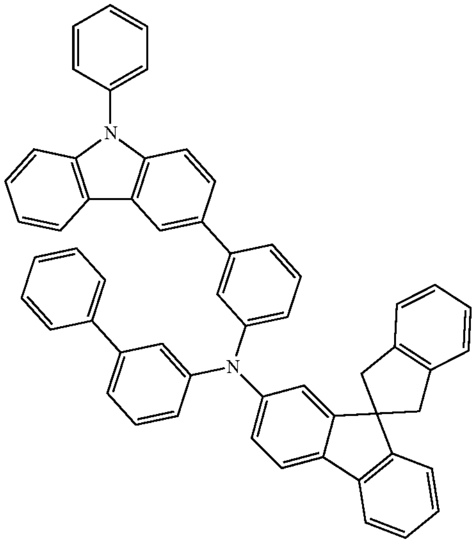
65
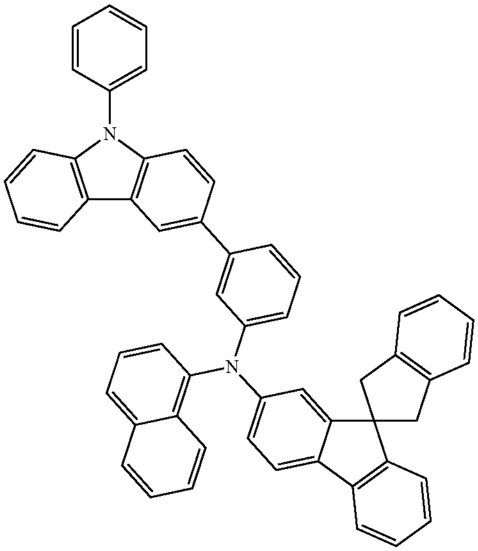
66
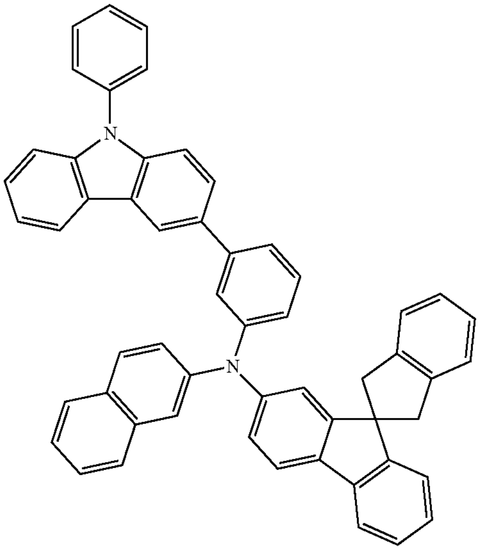
-continued
67
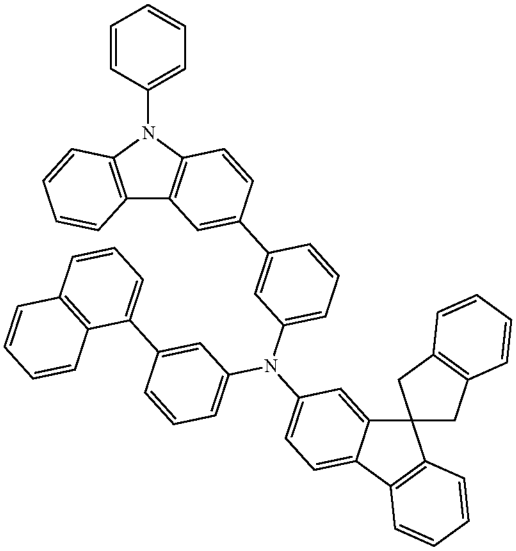
68
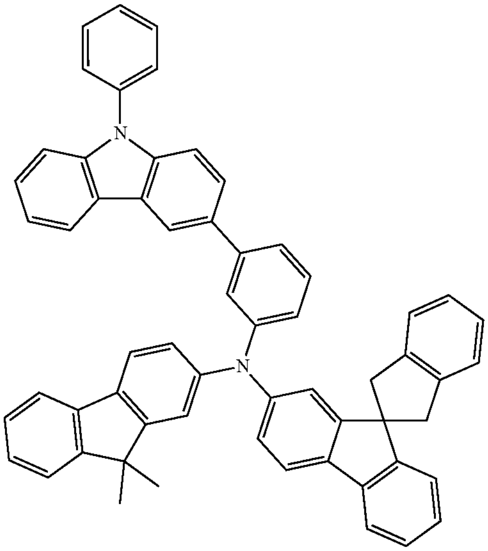
69
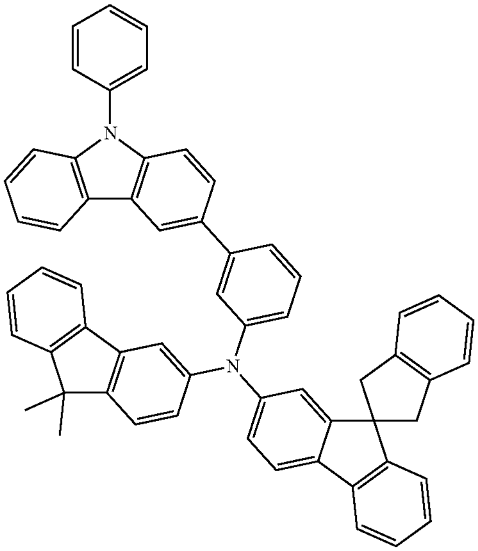

70
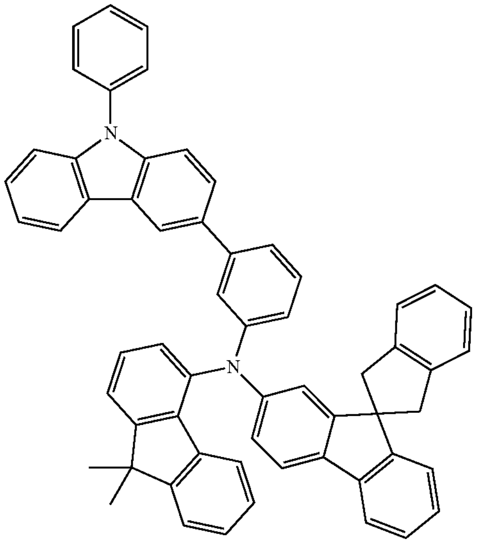
71
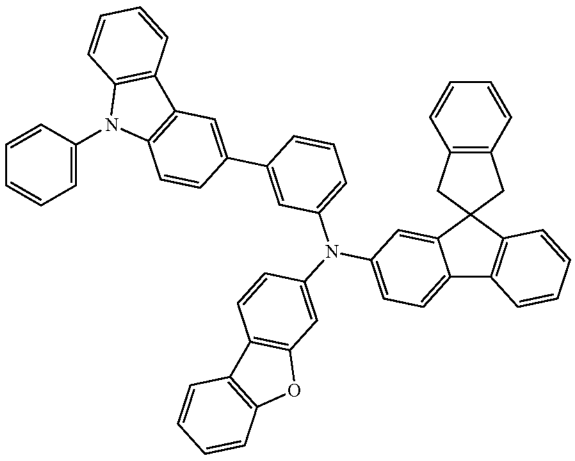
72
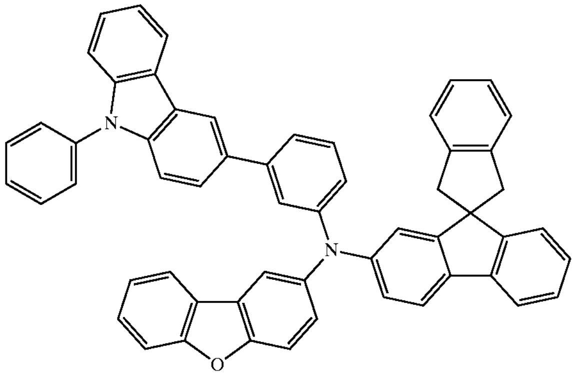
73
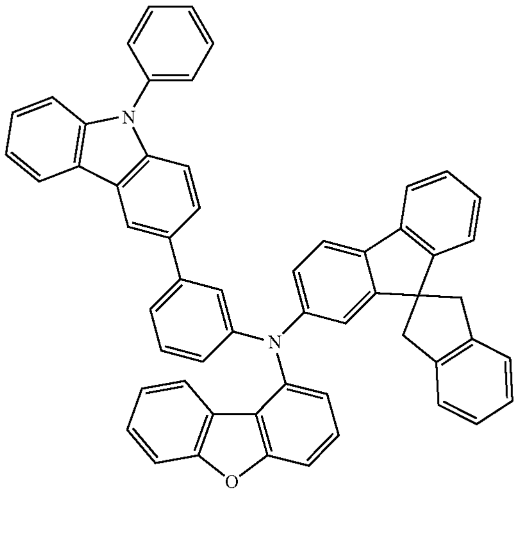
74
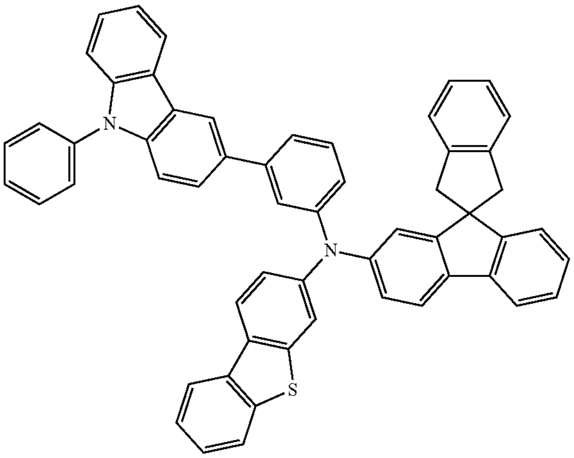
75
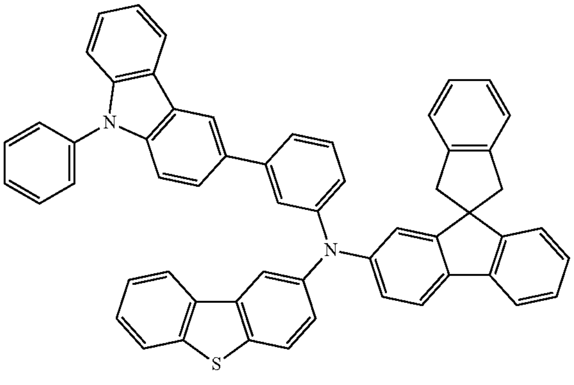

-continued
76
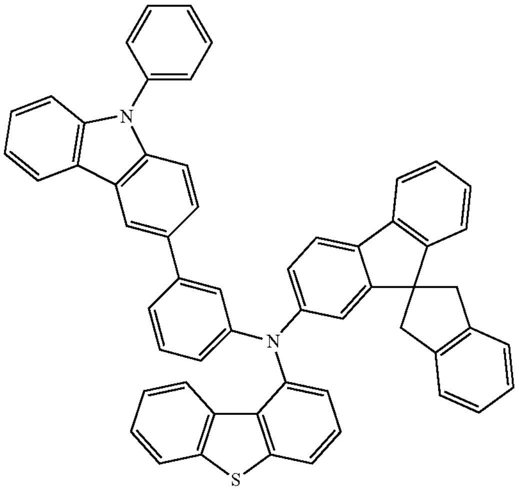
77
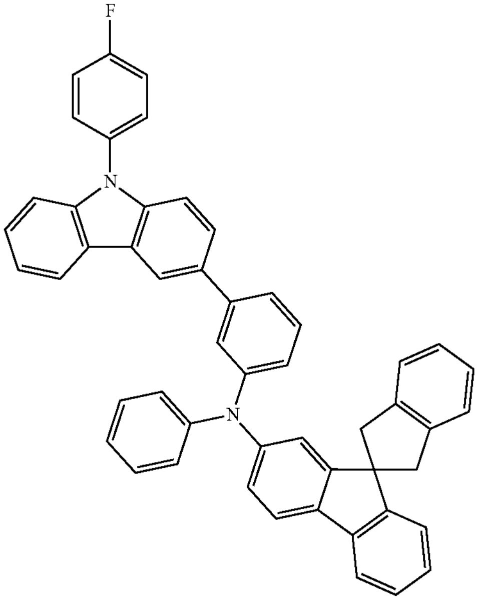
-continued
78
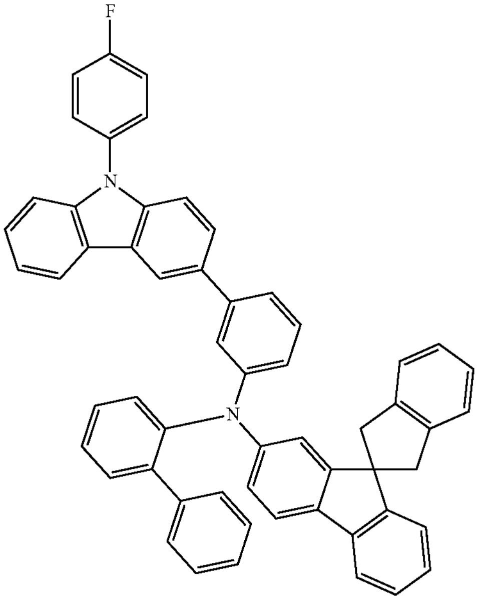
79
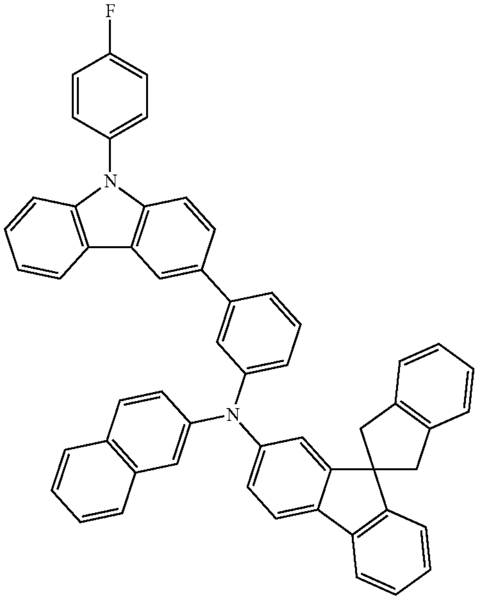

-continued
80
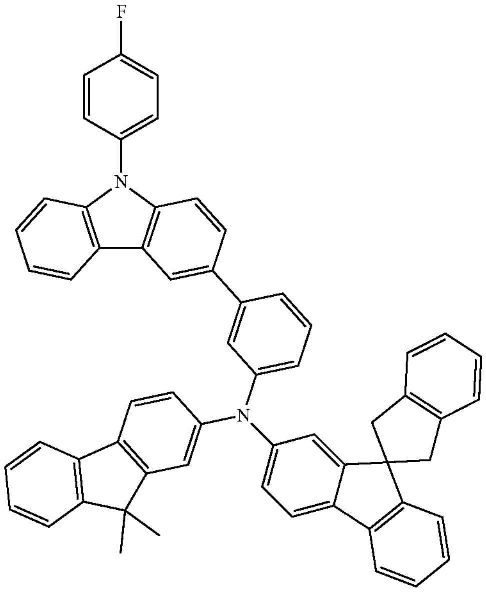
81
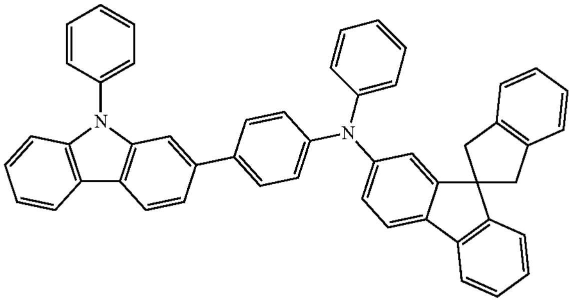
82
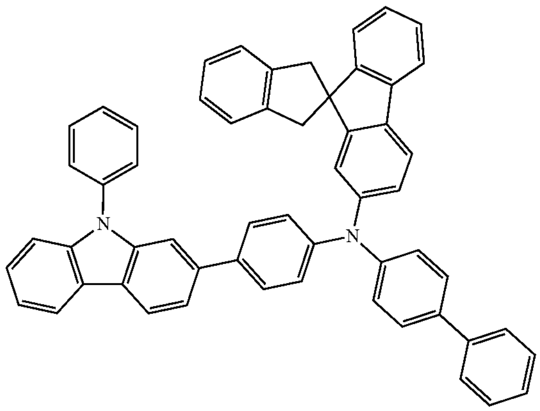
-continued
83
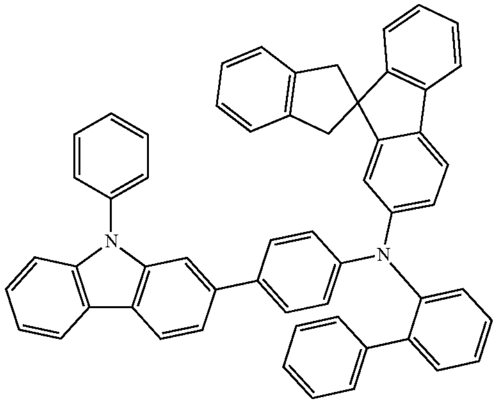
84
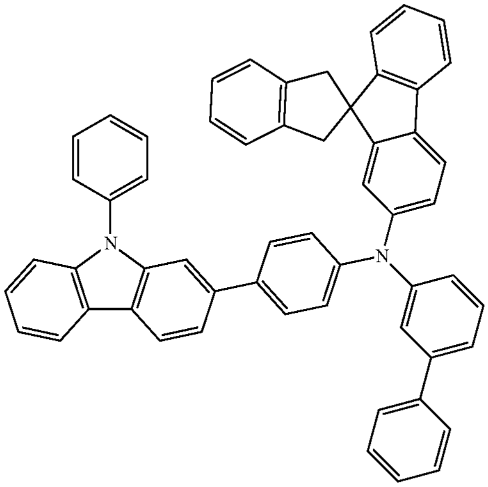
85
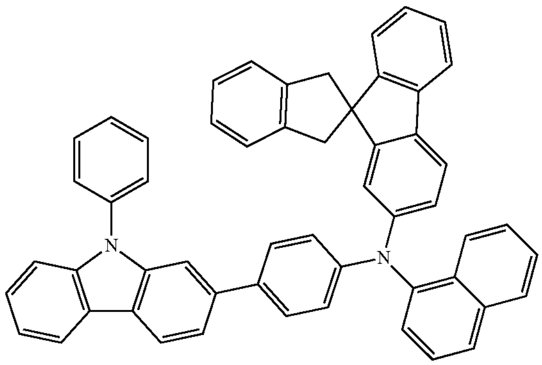

-continued
86
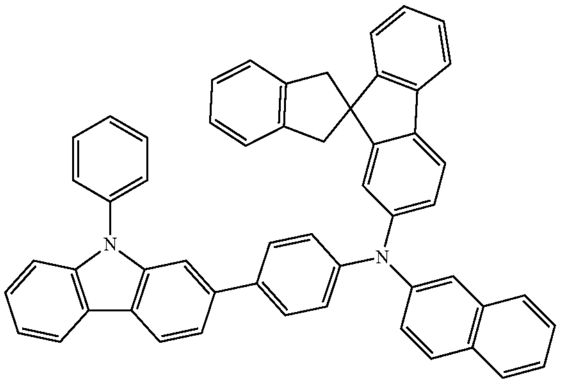
87
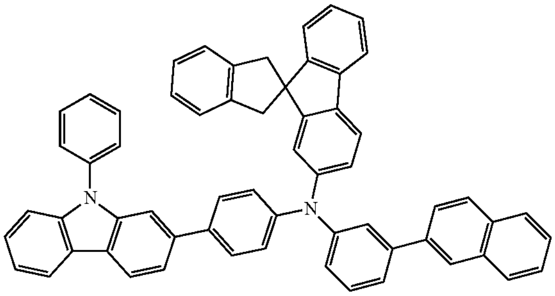
88
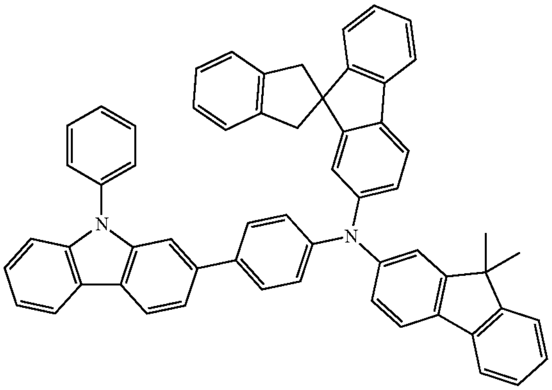
89
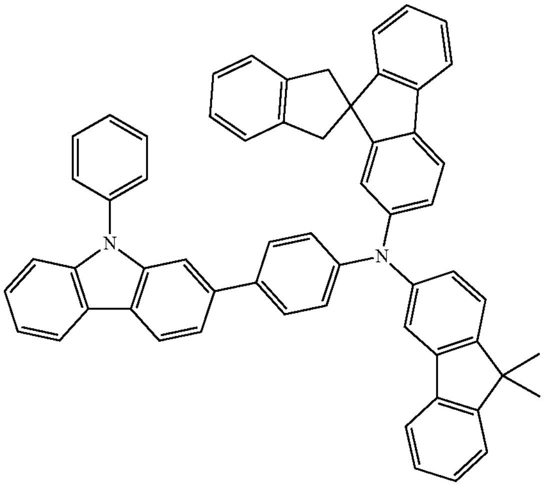
-continued
90
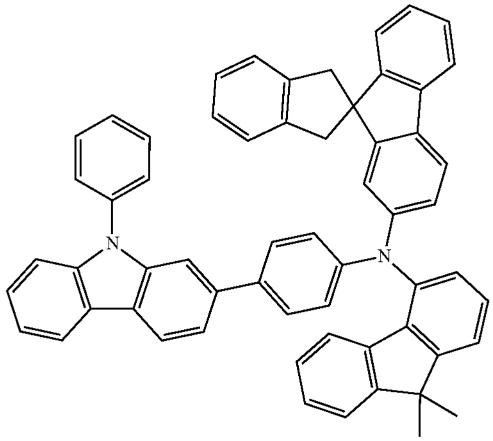
91
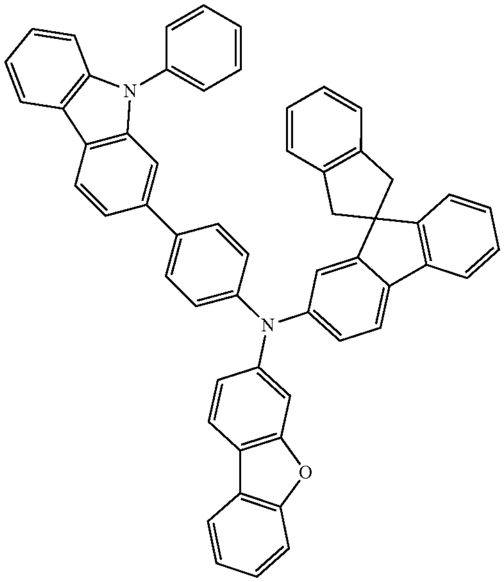
92
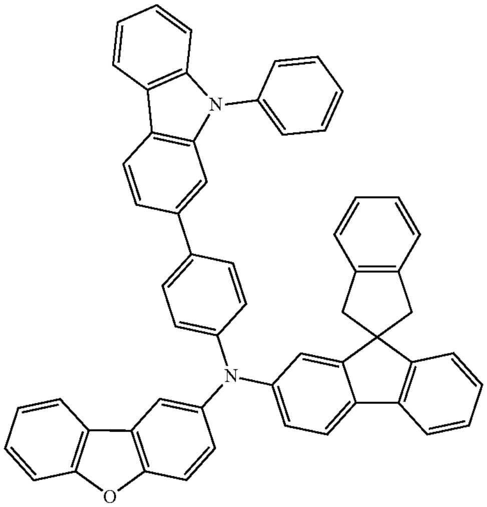

-continued
93
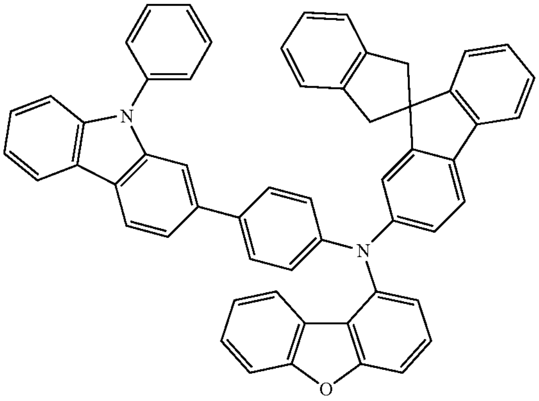
94
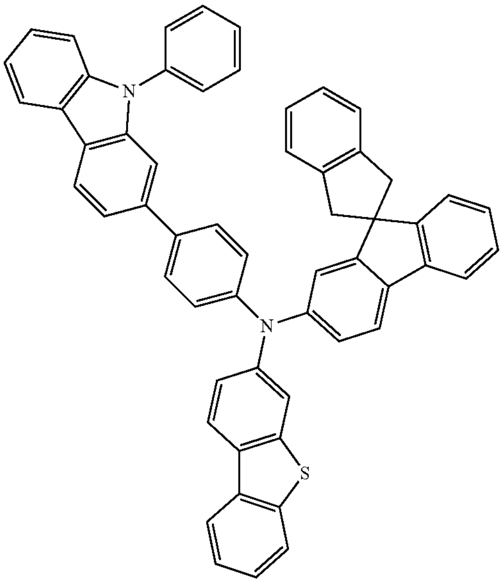
95
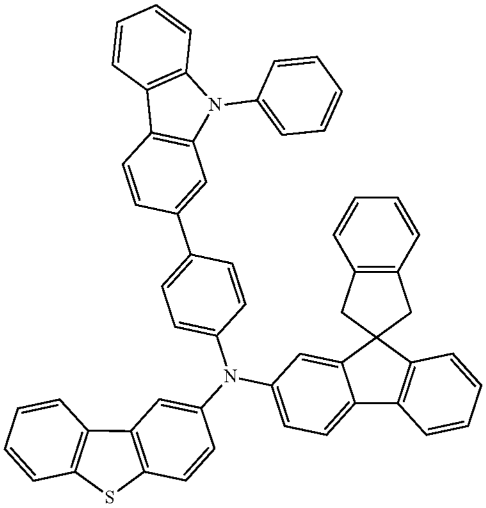
-continued
96
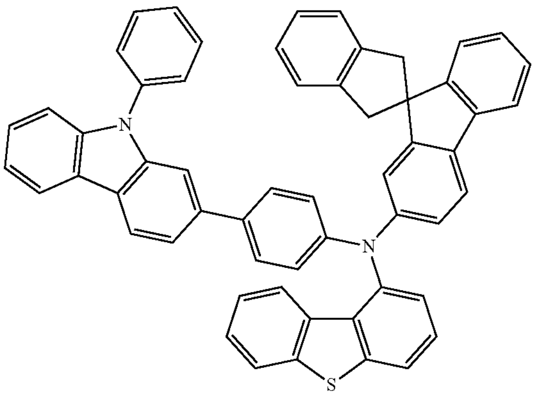
97
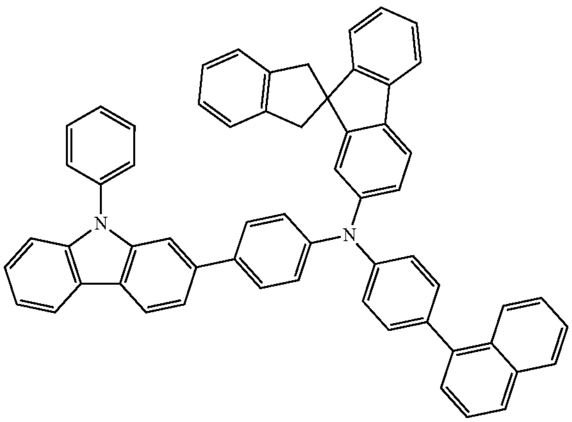
98
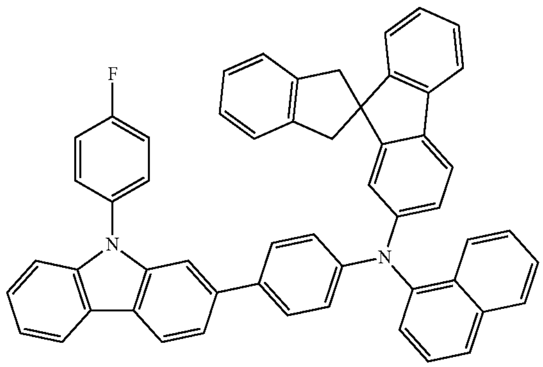
99
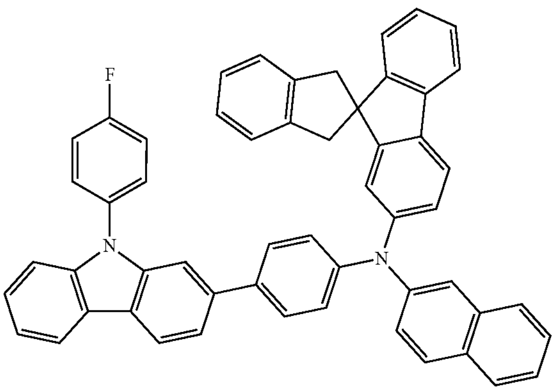

-continued
100
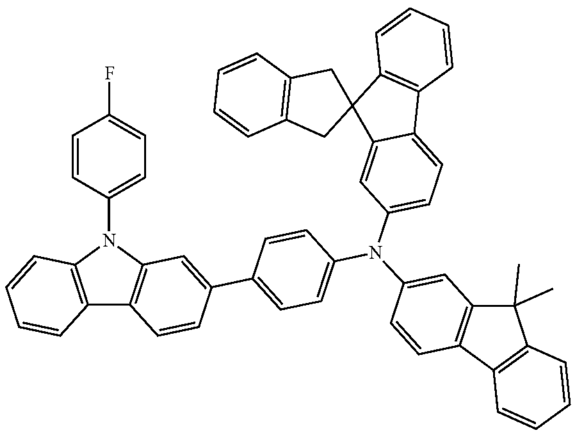
101
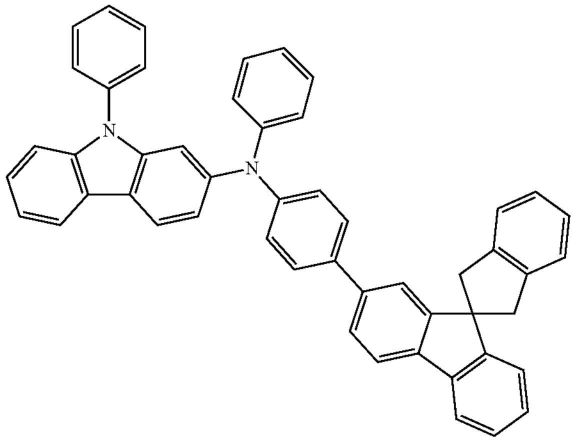
102
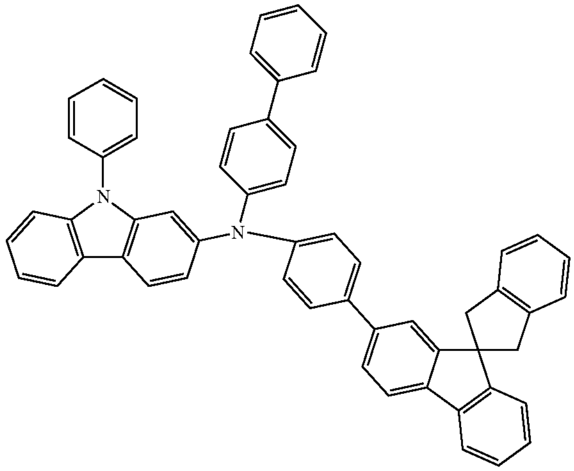
-continued
103
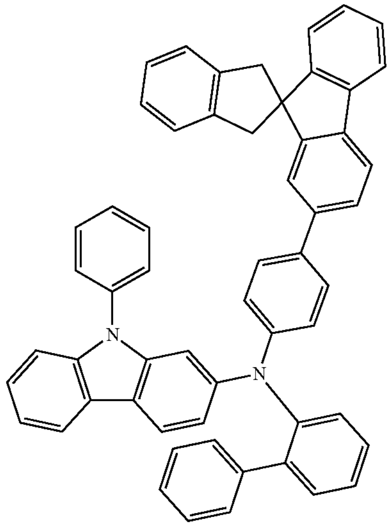
104
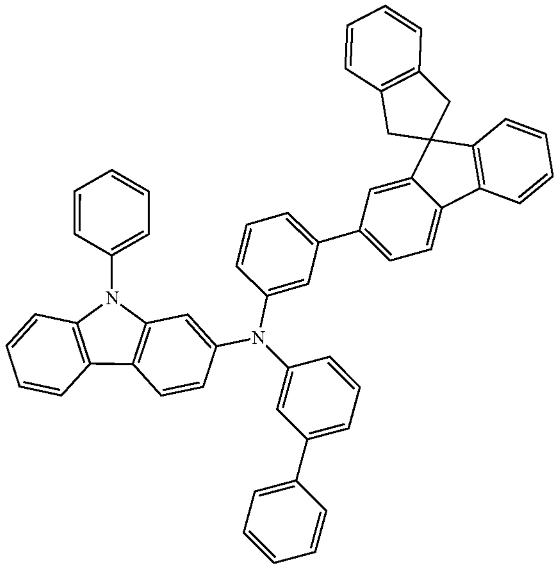
105
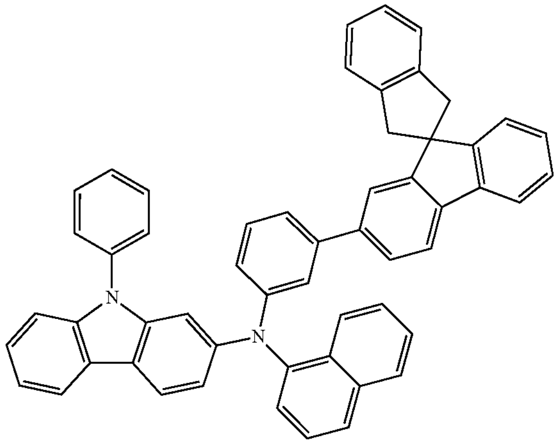

-continued
106
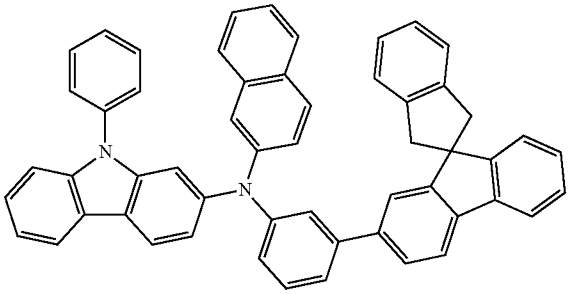
107
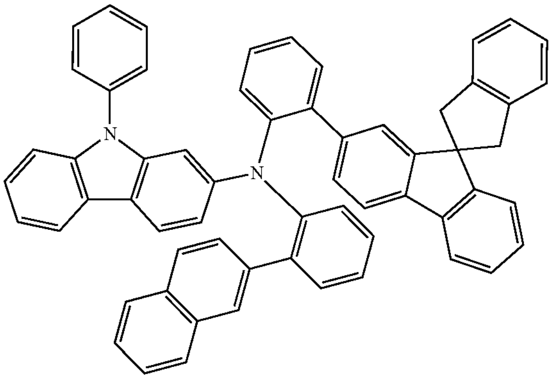
108
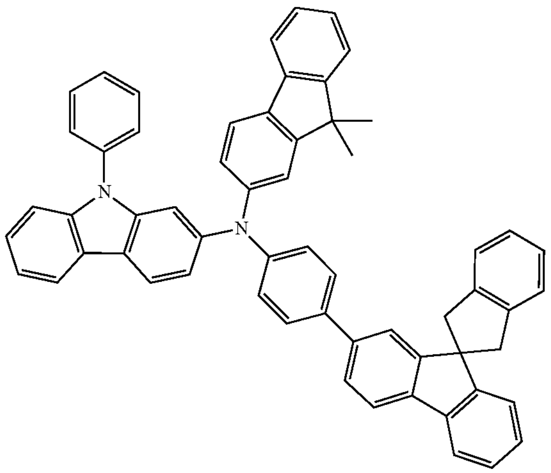
109
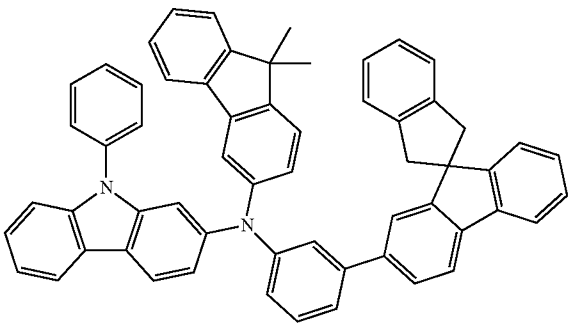
-continued
110
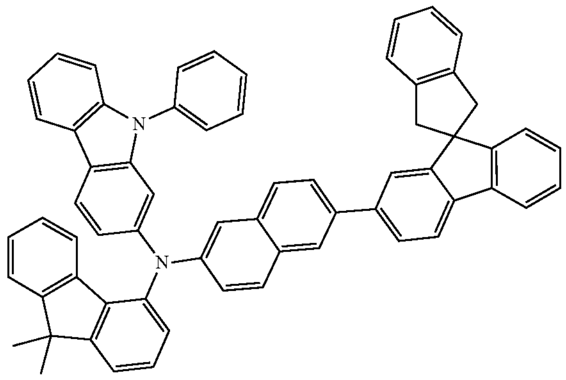
111
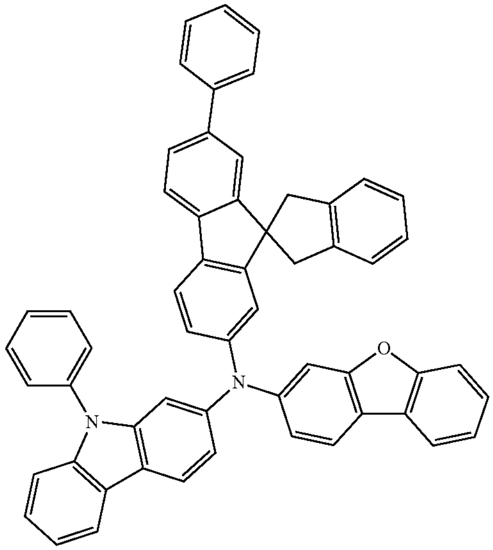
112
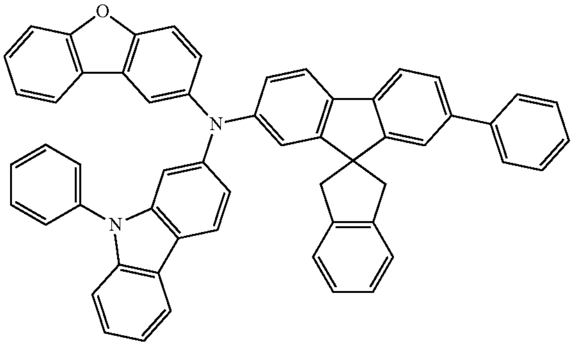

-continued
113
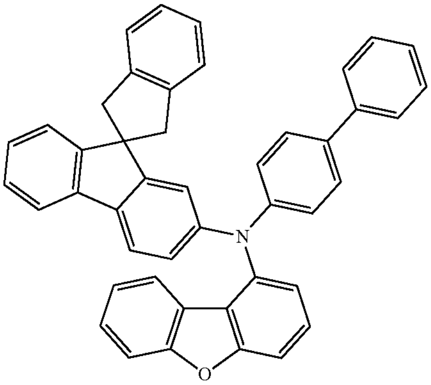
114
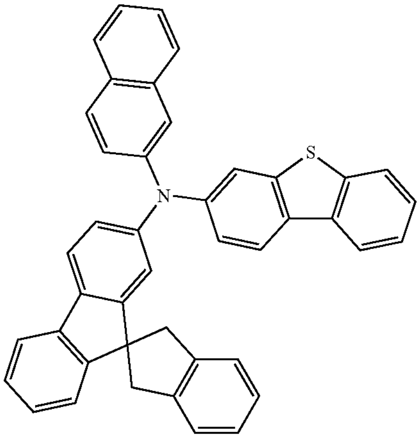
115
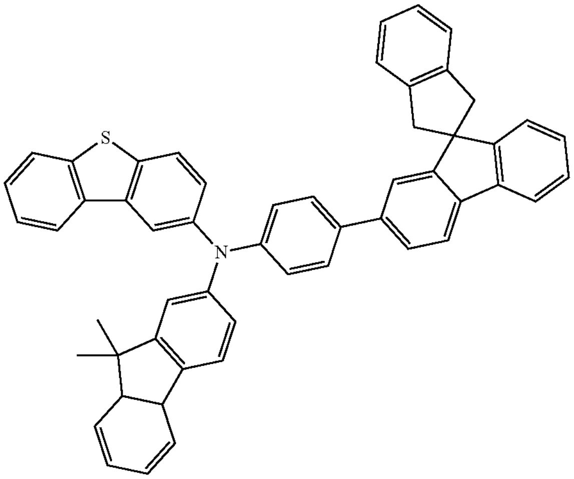
116
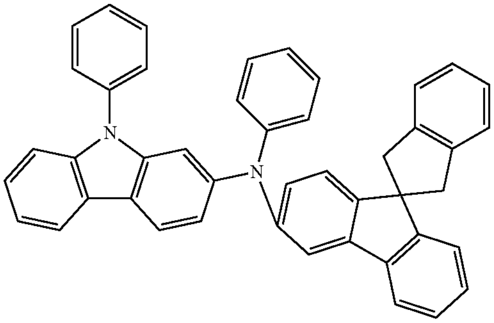
-continued
117
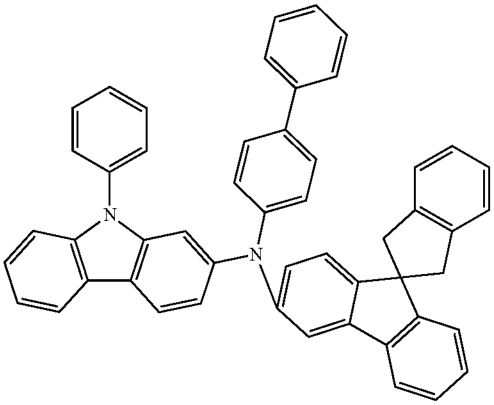
118
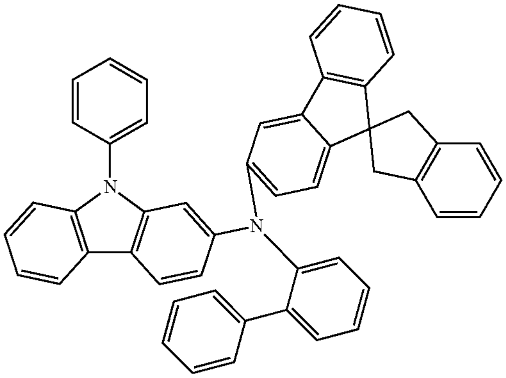
119
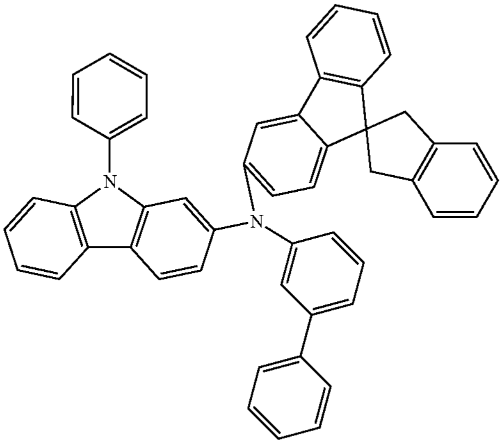
120
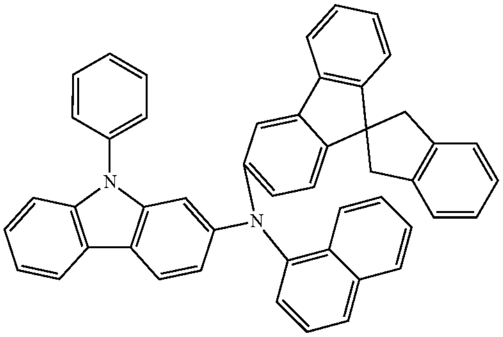

-continued
121
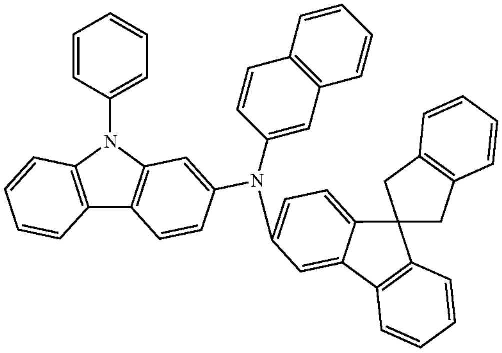
122
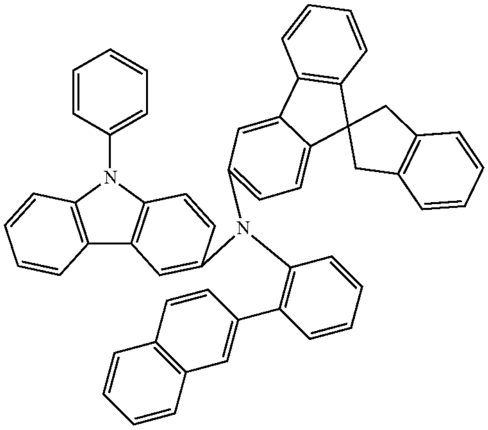
123
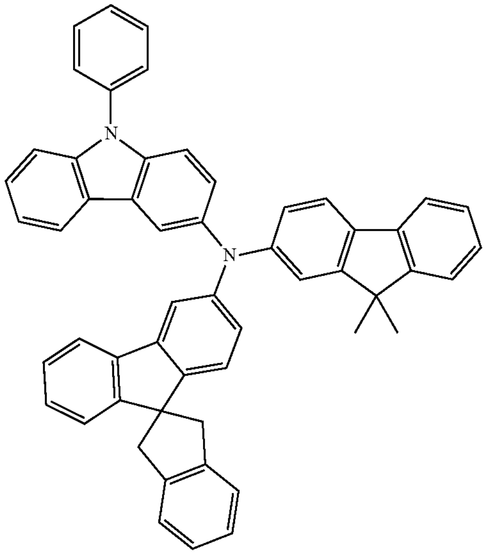
-continued
124
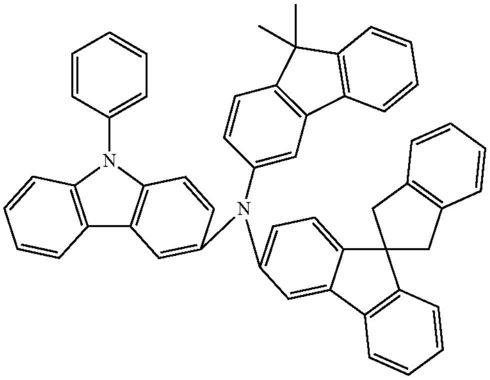
125
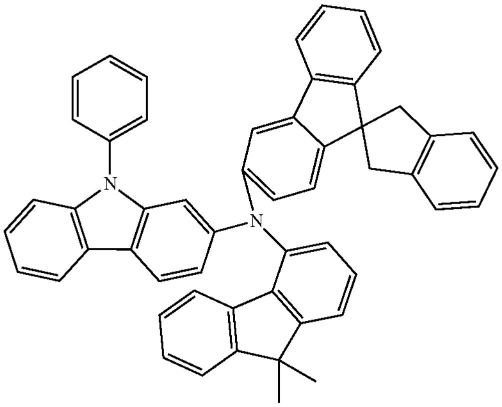
126
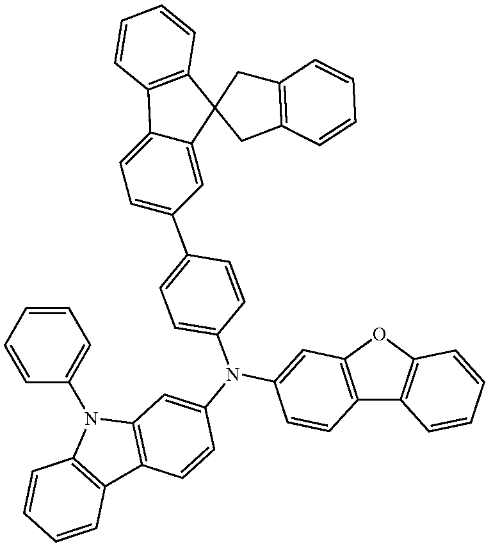

-continued

127

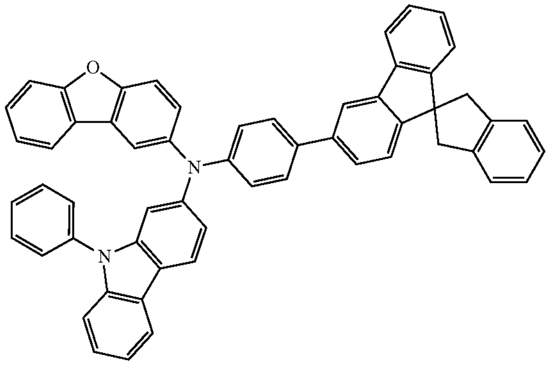

128

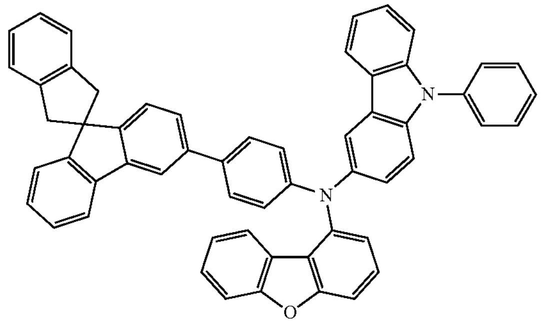

129

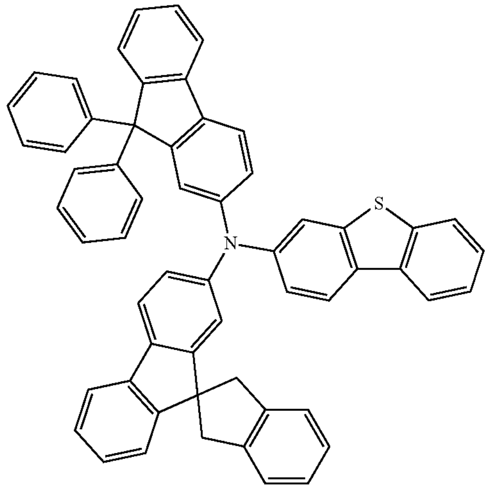

130

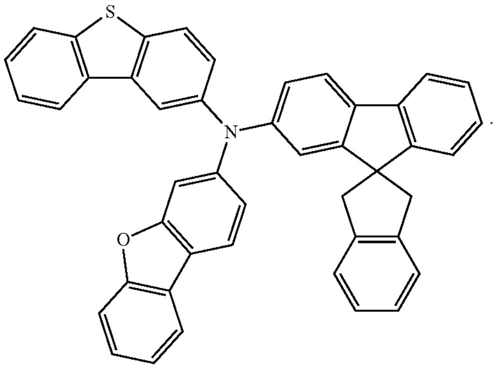

In some embodiments, in the light emitting device ED of an embodiment, the hole transport region HTR may further include any suitable material in the art.

The hole transport regions HTR may include, for example, a phthalocyanine compound (such as copper phthalocyanine);

$N^1$,$N^{1'}$-([1,1'-biphenyl]-4,4'-diyl)bis($N^1$-phenyl-$N^4$,$N^4$-di-m-tolylbenzene-1,4-diamine) (DNTPD), 4,4',4"-[tris(3-methylphenyl)phenylamino]triphenylamine] (m-MTDATA), 4,4',4"-tris(N,N-diphenylamino)triphenylamine (TDATA), 4,4',4"-tris {N,-(2-naphthyl)-N-phenylamino)-triphenylamine (2-TNATA), poly(3,4-ethylene dioxythiophene)/poly(4-styrene sulfonate) (PEDOT/PSS), polyaniline/dodecylbenzene sulfonic acid (PANI/DBSA), polyaniline/camphor sulfonic acid (PANI/CSA), polyaniline/poly(4-styrene sulfonate) (PANI/PSS), N,N'-di(naphthalene-1-yl)-N,N'-diphenyl-benzidine (NPB), triphenylamine-containing polyether ketone (TPAPEK), 4-isopropyl-4'-methyldiphenyliodonium [tetrakis(pentafluorophenyl) borate], dipyrazino[2,3-f: 2',3'-h]quinoxaline-2,3,6,7,10,11-hexacarbonitrile (HAT-CN), etc.

The hole transport region HTR may further include, for example, carbazole derivatives (such as N-phenyl carbazole and/or polyvinyl carbazole), fluorene derivatives, N,N'-bis (3-methylphenyl)-N, N'-diphenyl-[1, 1-biphenyl]-4,4'-diamine (TPD), triphenylamine derivatives (such as 4,4',4"-tris(N-carbazolyl)triphenylamine (TCTA)), N,N'-di (naphthalene-1-yl)-N, N'-diphenyl-benzidine (NPB), 4,4'-cyclohexylidene bis[N, N-bis(4-methylphenyl] benzenamine] (TAPC), 4,4'-bis[N,N'-(3-tolyl)amino]-3,3'-dimethylbiphenyl (HMTPD), 1,3-bis(N-carbazolyl)benzene (mCP), etc.

In some embodiments, the hole transport region HTR may include, for example, 9-(4-tert-butylphenyl)-3,6-bis(triphenylsilyl)-9H-carbazole (CzSi), 9-phenyl-9H-3,9'-bicarbazole (CCP), 1,3-bis(1,8-dimethyl-9H-carbazol-9-yl)benzene (mDCP), etc.

The hole transport region HTR may include the above-described compound of the hole transport region in at least one of a hole injection layer HIL, a hole transport layer HTL, or an electron blocking layer EBL.

The thickness of the hole transport region HTR may be about 100 Å to about 10,000 Å, for example, about 100 Å to about 5,000 Å. The thickness of the hole injection region HIL may be, for example, about 30 Å to about 1,000 Å, and the thickness of the hole transport layer HTL may be about 30 Å to about 1,000 Å. For example, the thickness of the electron blocking layer EBL may be about 10 Å to about 1,000 Å. When the thicknesses of the hole transport region HTR, the hole injection layer HIL, the hole transport layer HTL and the electron blocking layer EBL satisfy the above-described ranges, satisfactory hole transport properties may be achieved without a substantial increase in driving voltage.

The hole transport region HTR may further include a charge generating material in addition to the above-described materials to increase conductivity. The charge generating material may be dispersed substantially uniformly or non-uniformly in the hole transport region HTR. The charge generating material may be, for example, a p-dopant. The p-dopant may be one of quinone derivatives, metal oxides, or cyano group-containing compounds, but embodiments of the present disclosure are not limited thereto. For example, non-limiting examples of the p-dopant include quinone derivatives (such as tetracyanoquinodimethane (TCNQ) and/or 2,3,5,6-tetrafluoro-7,7',8,8'-tetracyanoquinodimethane (F4-TCNQ)), metal oxides (such as tungsten oxide and/or molybdenum oxide), metal halides (such as CuI and/or RbI), dipyrazino[2,3-f: 2',3'-h] quinoxaline-2,3,6,7,10,11-hexacarbonitrile (HAT-CN), 4-[2,3-bis[cyano-(4-cyano-2,3,5,6-tetrafluorophenyl)methylidene]cyclopropylidene]-cya nomethyl]-2,3,5,6-tetrafluorobenzonitrile, etc., but embodiments of the present disclosure are not limited thereto.

As described above, the hole transport region HTR may further include at least one of the hole buffer layer or the electron blocking layer EBL in addition to the hole injection layer HIL and the hole transport layer HTL. The hole buffer layer may compensate for a resonance distance of the wavelength of light emitted from the emission layer EML, and may thus increase light emission efficiency. Materials that may be included in the hole transport region HTR may be included in the hole buffer layer. The electron blocking layer EBL may prevent or reduce electrons from being injected from the electron transport region ETR to the hole transport region HTR. When the hole transport region HTR includes at least one of the hole buffer layer or the electron blocking layer adjacent to the emission layer EML, the amine compound according to an embodiment may be included in the hole buffer layer and/or the electron blocking layer adjacent to the emission layer EML.

The emission layer EML is provided on the hole transport region HTR. The emission layer EML may have a thickness of, for example, about 100 Å to about 1,000 Å or about 100 Å to about 300 Å. The emission layer EML may have a single layer formed of a single material, a single layer formed of a plurality of different materials, or a multilayer structure having a plurality of layers formed of a plurality of different materials.

In some embodiments, the emission layer EML of the light emitting device ED may be to emit blue light. For example, the emission layer EML of the light emitting device ED of an embodiment may be to emit blue light in the region of about 490 nm or more. However, embodiments of the present disclosure are not limited thereto, and the emission layer EML may be to emit green light or red light.

In some embodiments, the light emitting device ED of an embodiment may include a plurality of emission layers. The plurality of emission layers may be sequentially stacked, and for example, the light emitting device ED including the plurality of emission layers may be to emit white light. The organic electroluminescence device including a plurality of emission layers may be an organic electroluminescence device having a tandem structure.

In the light emitting device ED of an embodiment, the emission layer EML may include anthracene derivatives, pyrene derivatives, fluoranthene derivatives, chrysene derivatives, dihydrobenzanthracene derivatives, and/or triphenylene derivatives. For example, the emission layer EML may include anthracene derivatives and/or pyrene derivatives.

In each light emitting device ED of the embodiments illustrated in FIGS. 3 to 6, the emission layer EML may include a host and a dopant, and the emission layer EML may include a compound represented by Formula E-1. The compound represented by Formula E-1 may be utilized as a fluorescence host material.

Formula E-1

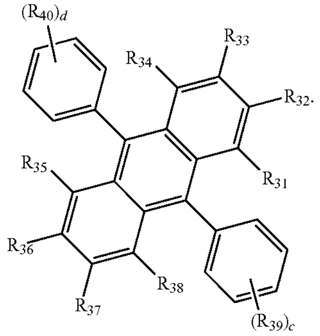

In Formula E-1, $R_{31}$ to $R_{40}$ may each independently be a hydrogen atom, a deuterium atom, a halogen atom, a substituted or unsubstituted silyl group, a substituted or unsubstituted alkyl group having 1 to 10 carbon atoms, a substituted or unsubstituted aryl group having 6 to 30 ring-forming carbon atoms, or a substituted or unsubstituted heteroaryl group having 2 to 30 ring-forming carbon atoms, and/or may be bonded to an adjacent group to form a ring. In some embodiments, $R_{31}$ to $R_{40}$ may be bonded to an adjacent group to form a saturated hydrocarbon ring or an unsaturated hydrocarbon ring.

In Formula E-1, c and d may each independently be an integer of 0 to 5.

Formula E-1 may be represented by any one among Compound E1 to Compound E18:

E1

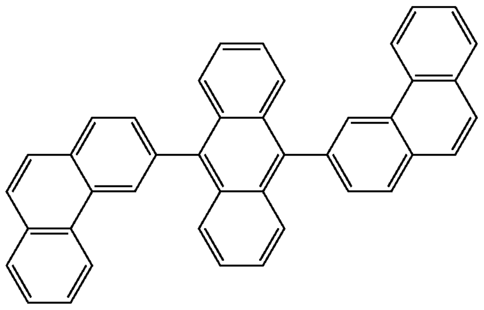

E2

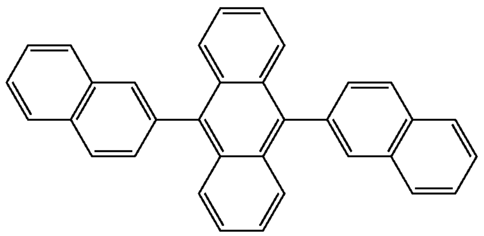

E3

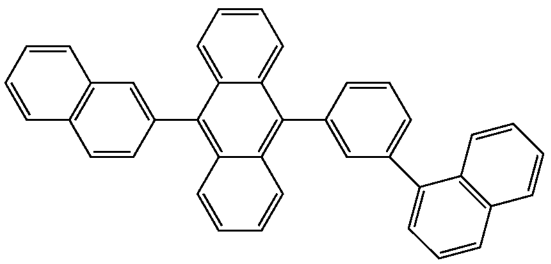

-continued
E4
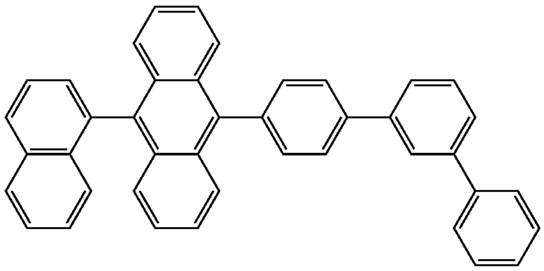
E5
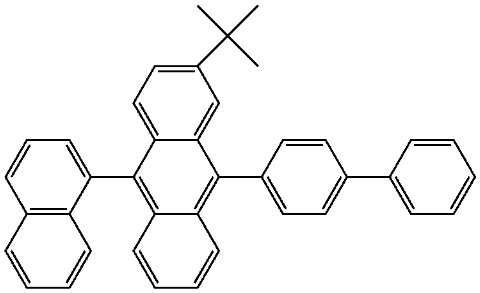
E6
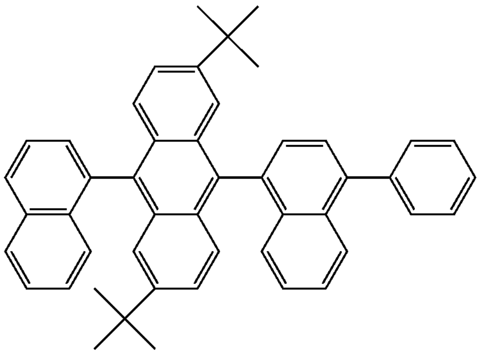
E7
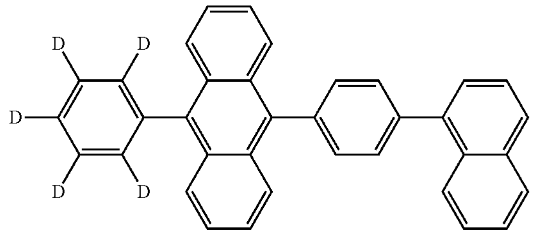
E8
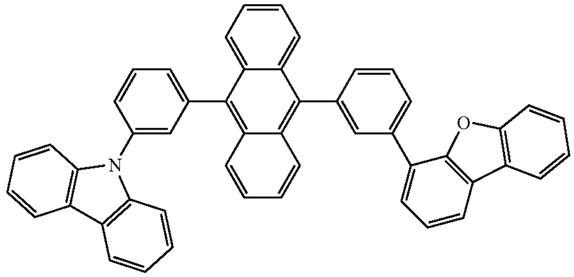
-continued
E9
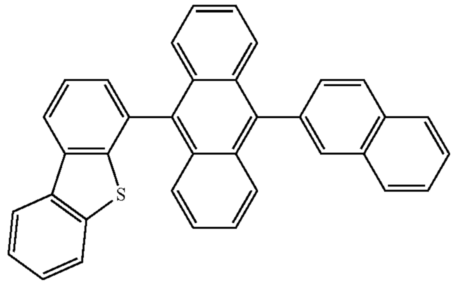
E10
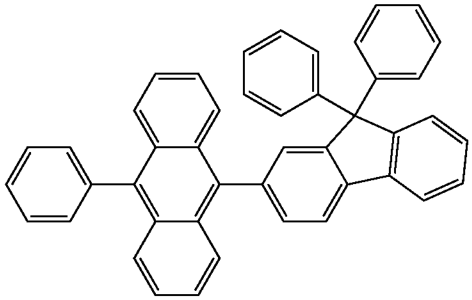
E11
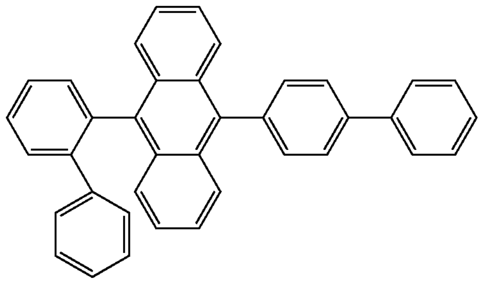
E12
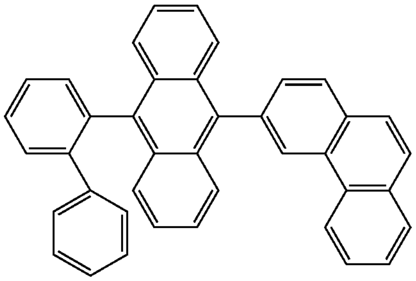
E13
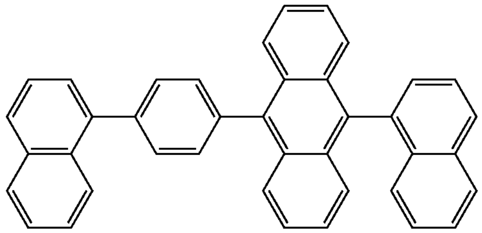

-continued

E14

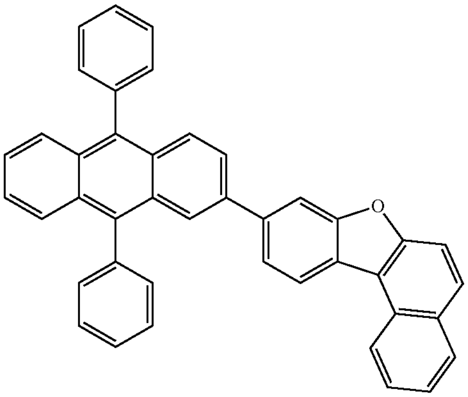

E15

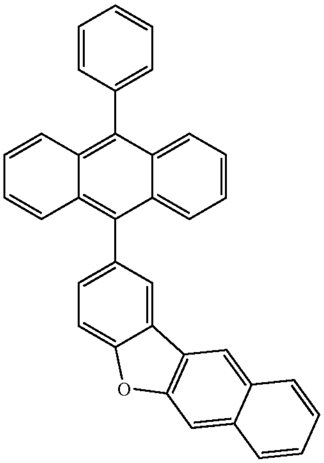

E16

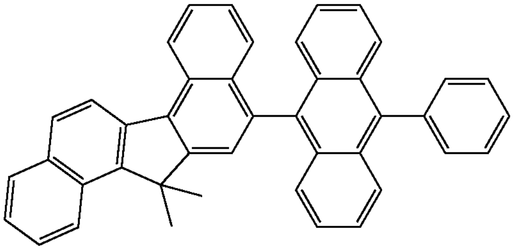

E17

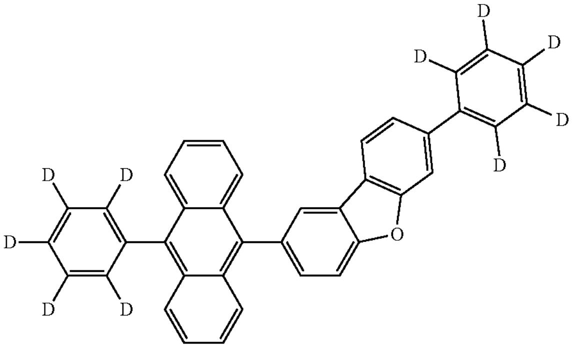

-continued

E18

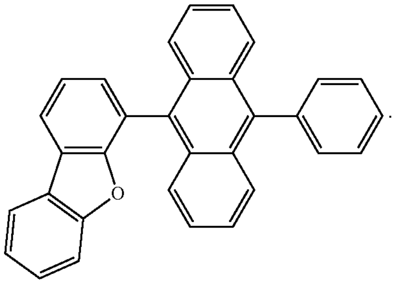

In an embodiment, the emission layer EML may include a compound represented by Formula E-2a or Formula E-2b. The compound represented by Formula E-2a or Formula E-2b may be utilized as a phosphorescence host material.

Formula E-2a

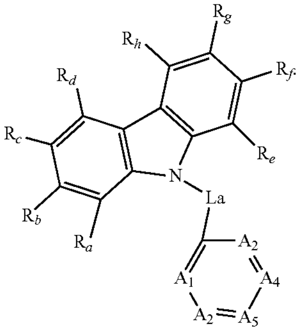

In Formula E-2a, La may be a direct linkage, or a substituted or unsubstituted arylene group having 6 to 30 ring-forming carbon atoms. In Formula E-2a, $A_1$ to $A_5$ may each independently be N or $CR_i$. $R_a$ to $R_i$ may each independently be a hydrogen atom, a deuterium atom, a substituted or unsubstituted amine group, a substituted or unsubstituted thio group, a substituted or unsubstituted oxy group, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, and/or may be bonded to an adjacent group to form a ring. In some embodiments, $R_a$ to $R_i$ may each independently be bonded to an adjacent group to form a hydrocarbon ring or a heterocycle containing N, O, S, etc. as a ring-forming atom.

In some embodiments, in Formula E-2a, two or three selected from among $A_1$ to $A_5$ may be N, and the others may be $CR_i$.

Formula E-2b $$(Cbz1)-L_b-(Cbz2).$$

In Formula E-2b, Cbz1 and Cbz2 may each independently be an unsubstituted carbazole group, or a carbazole group substituted with an aryl group having 6 to 30 ring-forming carbon atoms. $L_b$ may be a direct linkage, or a substituted or unsubstituted arylene group having 6 to 30 ring-forming carbon atoms.

The compound represented by Formula E-2a or Formula E-2b may be represented by any one among the compounds of Compound Group E-2. However, the compounds listed in Compound Group E-2 are examples, and the compound represented by Formula E-2a or Formula E-2b is not limited to those represented by Compound Group E-2.
Compound Group E-2
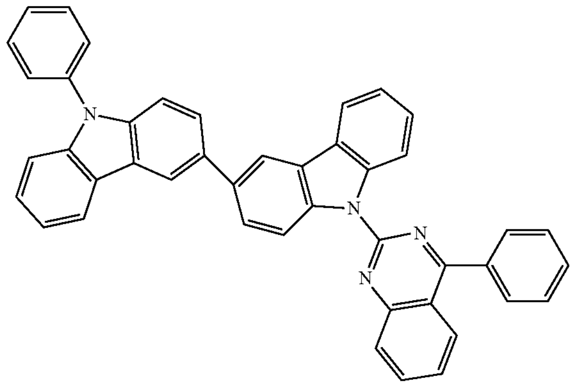
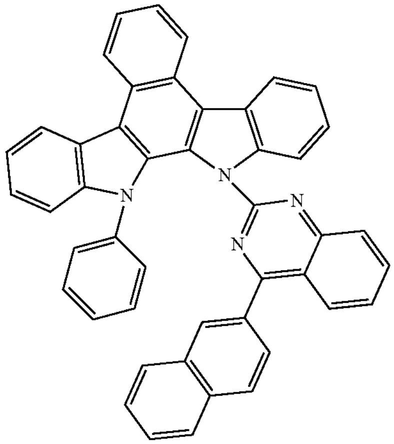
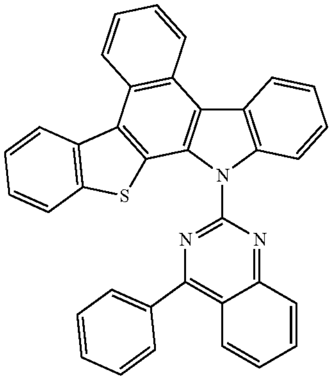
-continued
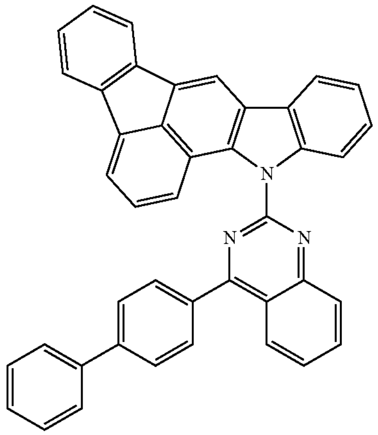
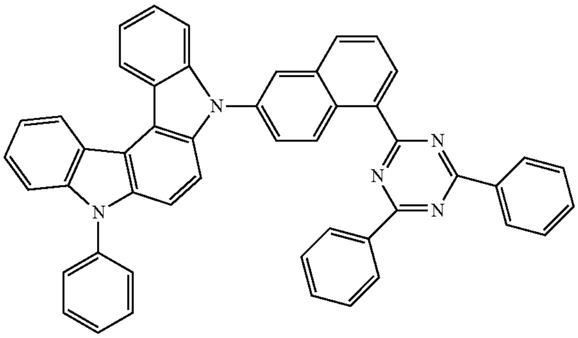
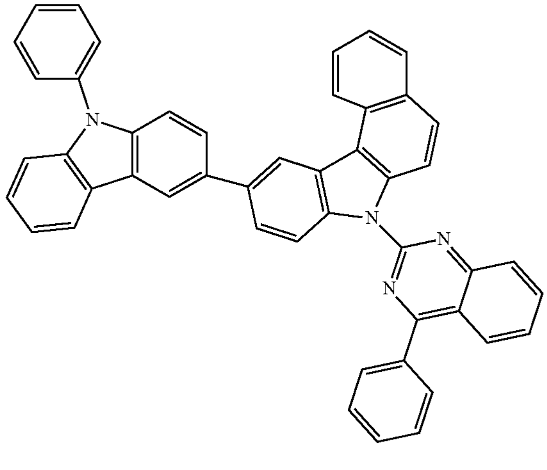
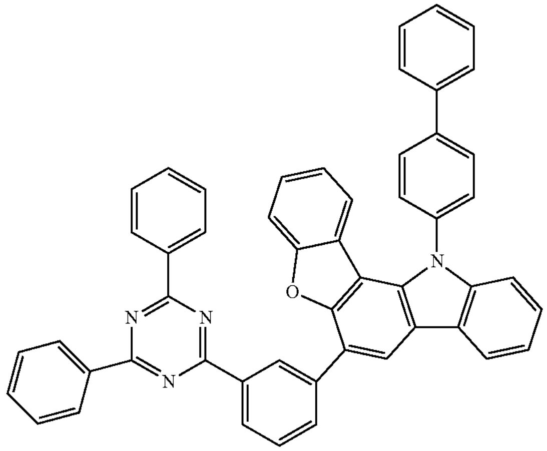

-continued
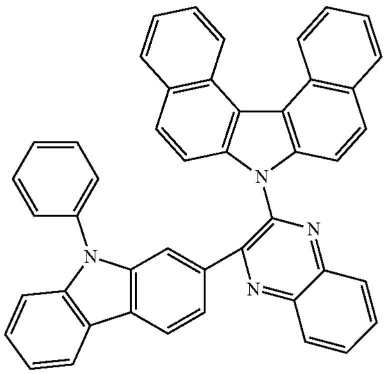
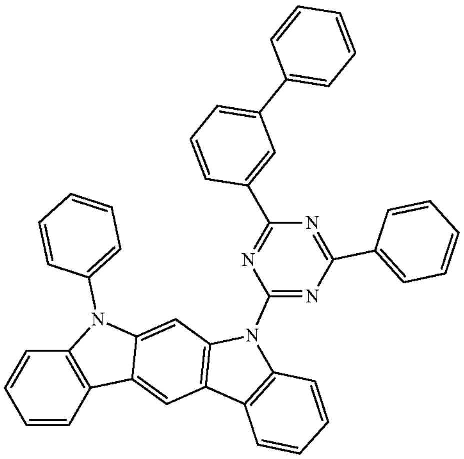
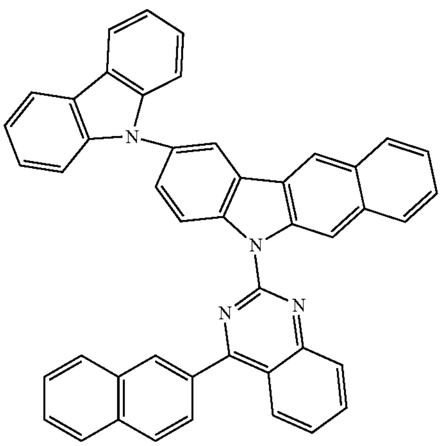
-continued
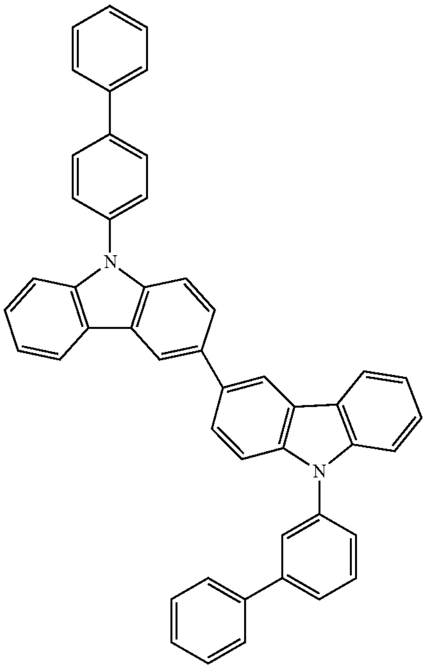
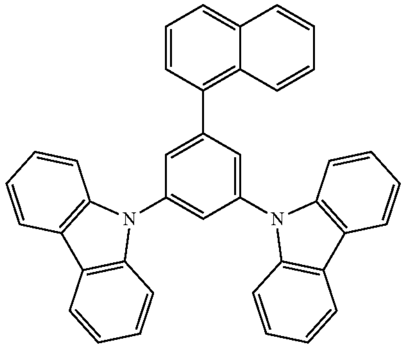
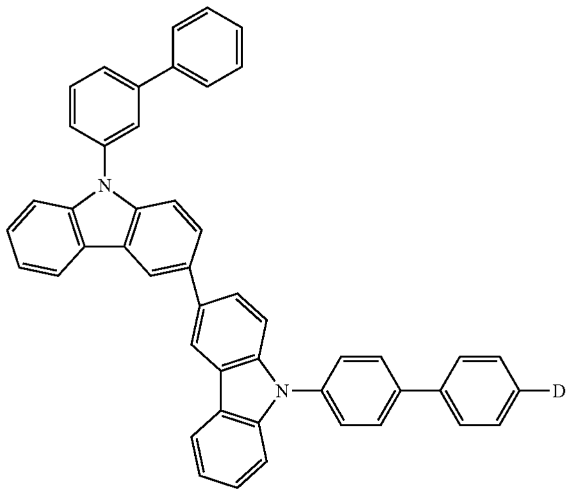

-continued

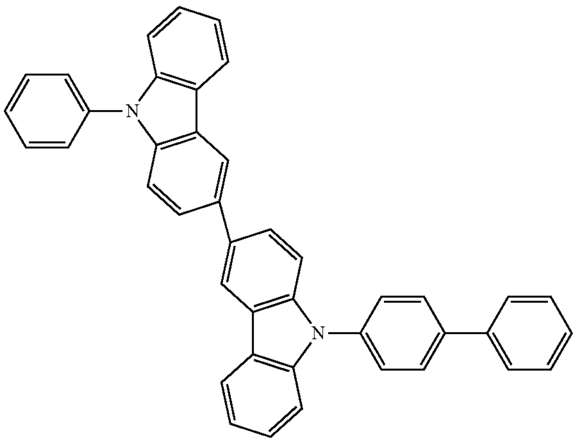

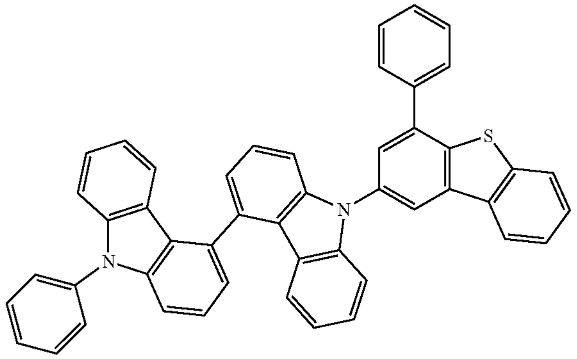

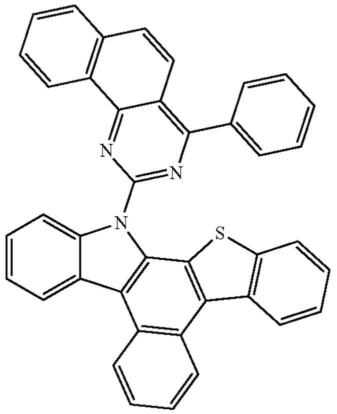

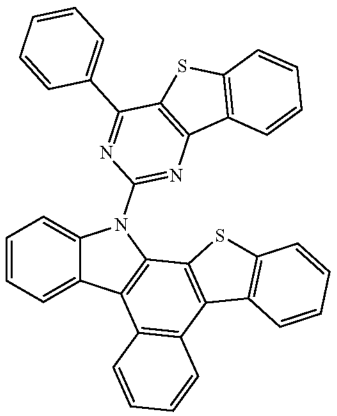

-continued

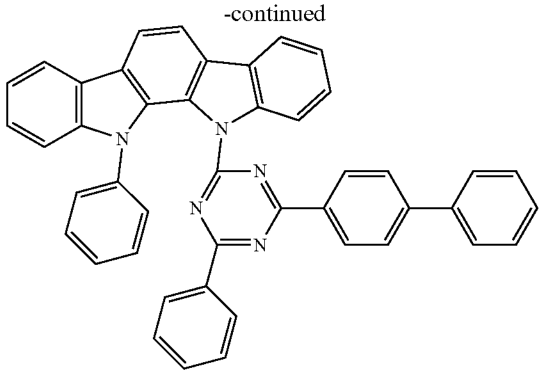

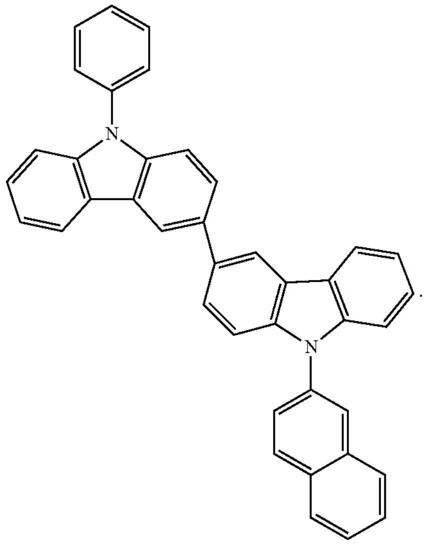

The emission layer EML may further include any suitable in the art as a host material. For example, the emission layer EML may include, as a host material, at least one of bis[2-(diphenylphosphino)phenyl] ether oxide (DPEPO), 4,4'-bis(carbazol-9-yl) biphenyl (CBP), 1,3-bis(carbazol-9-yl)benzene (mCP), 2,8-bis(diphenylphosphoryl)dibenzo[b,d]furan (PPF), 4,4',4"-tris(carbazol-9-yl)-triphenylamine (TCTA), or 1,3,5-tris(1-phenyl-1H-benzo[d]imidazole-2-yl)benzene (TPBi). However, embodiments of the present disclosure are not limited thereto, and for example, tris(8-hydroxyquinolino)aluminum ($Alq_3$), 4,4'-bis(N-carbazolyl)-1,1'-biphenyl (CBP), poly(n-vinylcarbazole (PVK), 9,10-di(naphthalene-2-yl) anthracene (ADN), 4,4',4"-tris(carbazol-9-yl)-triphenylamine (TCTA), 1,3,5-tris(N-phenylbenzimidazole-2-yl)benzene (TPBi), 2-tert-butyl-9,10-di(naphth-2-yl) anthracene (TBADN), distyrylarylene (DSA), 4,4'-bis(9-carbazolyl)-2,2'-dimethyl-biphenyl (CDBP), 2-methyl-9,10-bis(naphthalen-2-yl) anthracene (MADN), hexaphenylcyclotriphosphazene (CP1), 1,4-bis(triphenylsilyl)benzene (UGH2), hexaphenylcyclotrisiloxane (DPSiO3), octaphenylcyclotetra siloxane (DPSiO4), 2,8-bis(diphenylphosphoryl)dibenzofuran (PPF), etc. may be utilized as a host material.

The emission layer EML may include a compound represented by Formula M-a or Formula M-b. The compound represented by Formula M-a or Formula M-b may be utilized as a phosphorescence dopant material:

Formula M-a

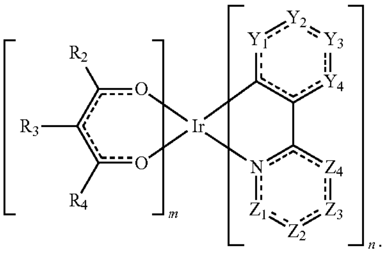

In Formula M-a, $Y_1$ to $Y_4$ and $Z_1$ to $Z_4$ may each independently be $CR_1$ or N, $R_1$ to $R_4$ may each independently be a hydrogen atom, a deuterium atom, a substituted or unsubstituted amine group, a substituted or unsubstituted thio group, a substituted or unsubstituted oxy group, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, and/or may be bonded to an adjacent group to form a ring. In Formula M-a, m may be 0 or 1, and n may be 2 or 3. In Formula M-a, when m is 0, n may be 3, and when m is 1, n may be 2.

The compound represented by Formula M-a may be utilized as a red phosphorescence dopant or a green phosphorescence dopant.

The compound represented by Formula M-a may be represented by any one among Compound M-a1 to Compound M-a6. However, Compounds M-a1 to M-a6 are examples, and the compound represented by Formula M-a is not limited to those represented by Compounds M-a1 to M-a6:

M-a1

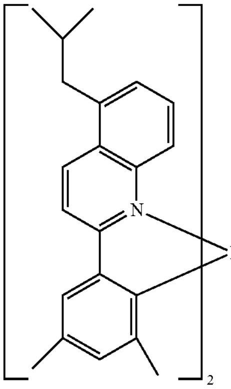

-continued

M-a2

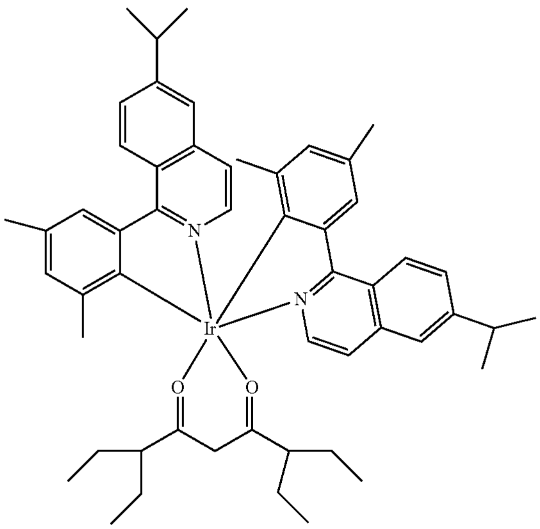

M-a3

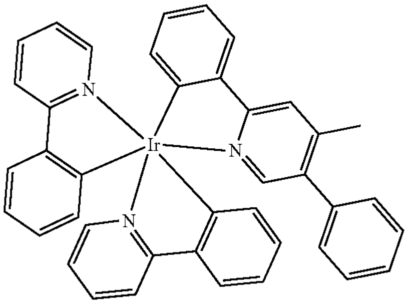

M-a4

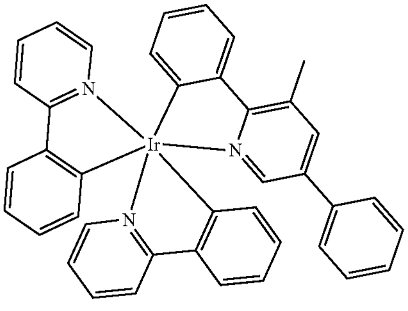

M-a5

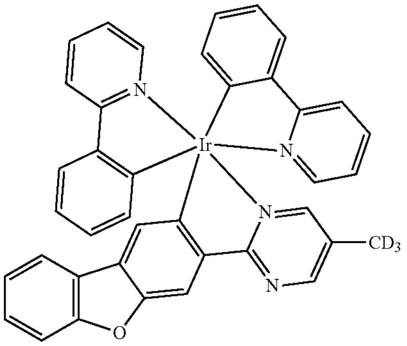

-continued

M-a6

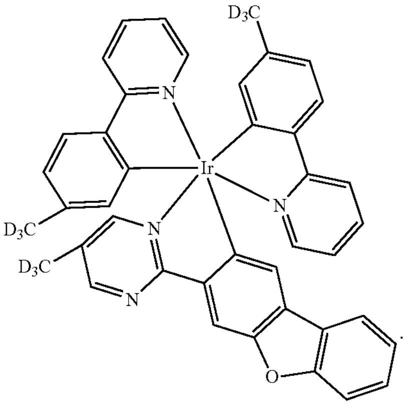

Compound M-a1 and Compound M-a2 may be utilized as a red dopant material, and Compound M-a3 and Compound M-a4 may be utilized as a green dopant material.

Formula M-b

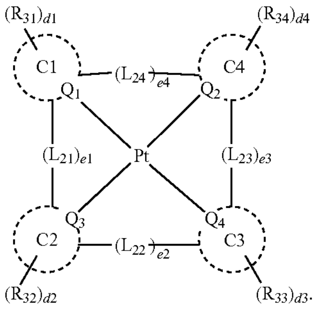

In Formula M-b, $Q_1$ to $Q_4$ may each independently be C or N, and $C_1$ to $C_4$ may each independently be a substituted or unsubstituted hydrocarbon ring having 5 to 30 ring-forming carbon atoms, or a substituted or unsubstituted heterocycle having 2 to 30 ring-forming carbon atoms. $L_{21}$ to $L_{24}$ may each independently be a direct linkage,

*—O—*, *—S—*, 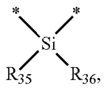, 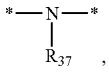,

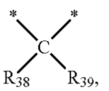, 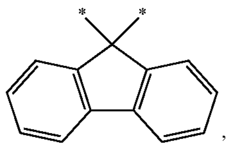, substituted or unsubstituted divalent alkyl group having 1 to 20 carbon atoms, a substituted or unsubstituted arylene group having 6 to 30 ring-forming carbon atoms, or a substituted or unsubstituted heteroarylene group having 2 to 30 ring-forming carbon atoms, and e1 to e4 may each independently be 0 or 1. $R_{31}$ to $R_{39}$ may each independently be a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and/or may be bonded to an adjacent group to form a ring, and d1 to d4 may each independently be an integer of 0 to 4.

The compound represented by Formula M-b may be utilized as a blue phosphorescence dopant or a green phosphorescence dopant.

The compound represented by Formula M-b may be represented by any one among the compounds below. However, the compounds below are examples, and the compound represented by Formula M-b is not limited to those represented by the compounds below.

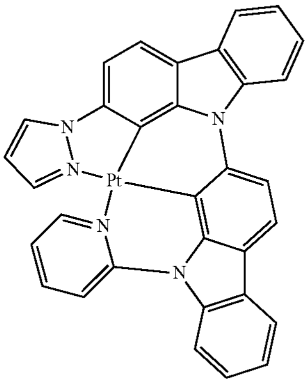

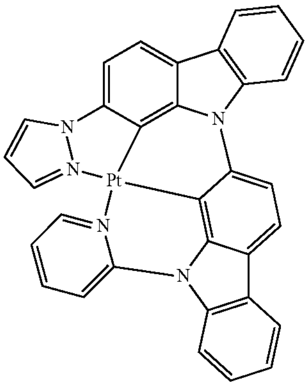

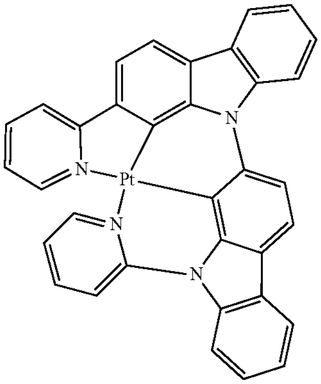

-continued
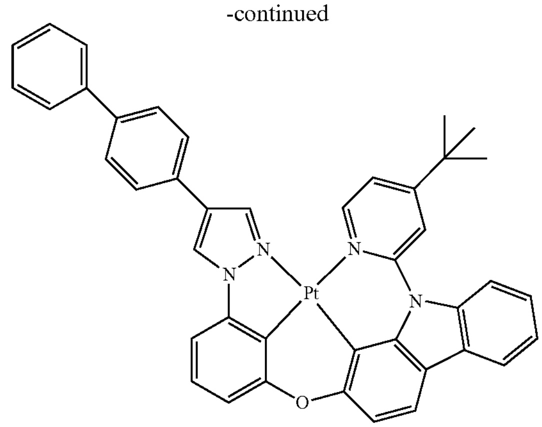
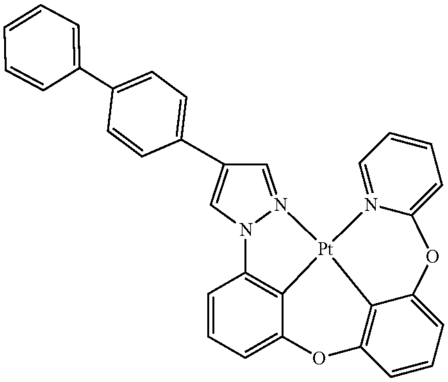
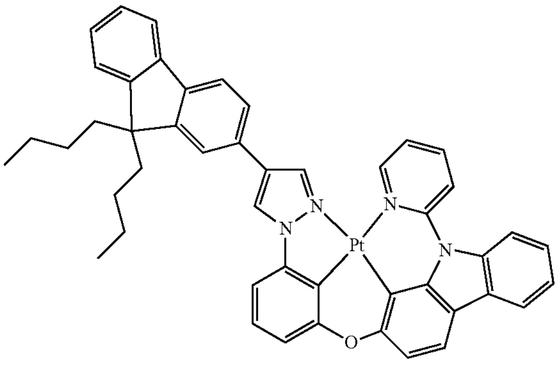
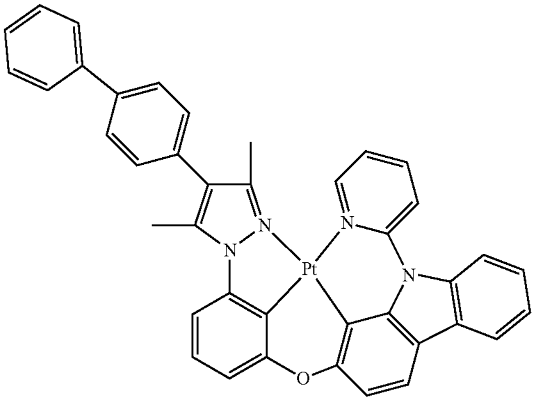
-continued
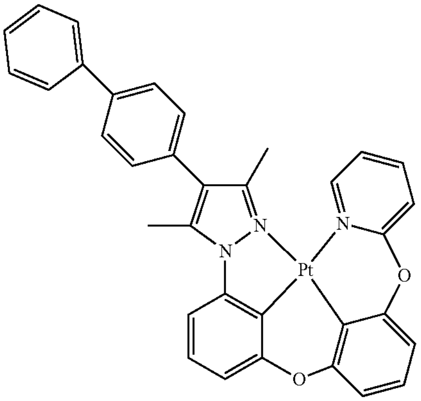
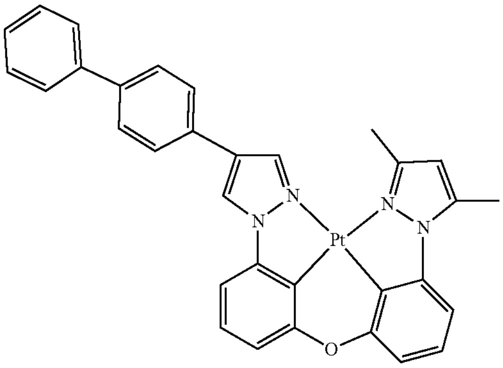
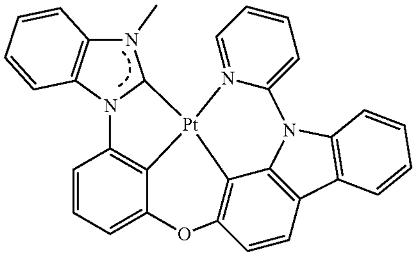
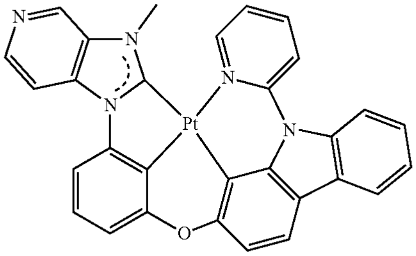
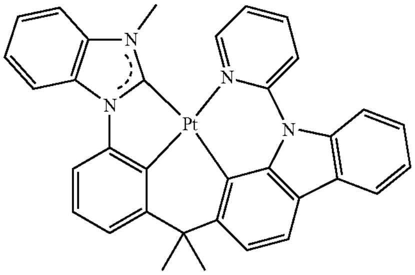
.
The emission layer EML may include a compound represented by any one among Formula F-a to Formula F-c. The compound represented by Formula F-a or Formula F-c may be utilized as a fluorescence dopant material:

Formula F-a

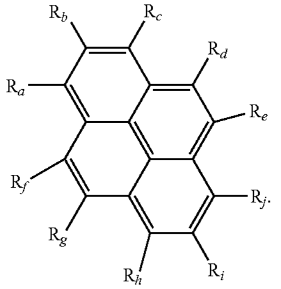

In Formula F-a, two selected from among $R_a$ to $R_j$ may each independently be substituted with •—$NAr_1Ar_2$. The others, which are not substituted with •—$NAr_1Ar_2$, among $R_a$ to $R_j$ may each independently be a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. In •—$NAr_1Ar_2$, $Ar_1$ and $Ar_2$ may each independently be a substituted or unsubstituted aryl group having 6 to 30 ring-forming carbon atoms, or a substituted or unsubstituted heteroaryl group having 2 to 30 ring-forming carbon atoms. For example, at least one of $Ar_1$ or $Ar_2$ may be a heteroaryl group containing O or S as a ring-forming atom.

Formula F-b

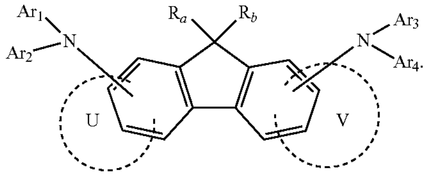

In Formula F-b, U and V may each independently be a substituted or unsubstituted hydrocarbon ring having 5 to 30 ring-forming carbon atoms, or a substituted or unsubstituted heterocycle having 2 to 30 ring-forming carbon atoms.

In Formula F-b, the number of rings represented by U and V may each independently be 0 or 1. For example, in Formula F-b, when the either of U or Vis 1, a condensed ring is present at a part described as U and/or V, and when either of U or V is 0, a ring described as U or V is not present. For example, when the number of U is 0 and the number of V is 1, or when the number of U is 1 and the number of V is 0, the condensed ring having a fluorene core of Formula F-b may be a four-ring cyclic compound. In some embodiments, when U and V are each 0, the condensed ring of Formula F-b may be a three-ring cyclic compound. In some embodiments, when U and V are each 1, the condensed ring having a fluorene core of Formula F-b may be a five-ring cyclic compound.

Formula F-c

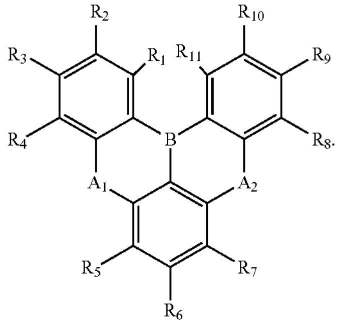

In Formula F-c, $A_1$ and $A_2$ may each independently be O, S, Se, or $NR_m$, and $R_m$ may be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. $R_1$ to $R_{11}$ may each independently be a hydrogen atom, a deuterium atom, a halogen atom, a cyano group, a substituted or unsubstituted amine group, a substituted or unsubstituted boryl group, a substituted or unsubstituted oxy group, a substituted or unsubstituted thio group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and/or may be bonded to an adjacent group to form a ring.

In Formula F-c, $A_1$ and $A_2$ may each independently be bonded to substituents of an adjacent ring to form a condensed ring. For example, when $A_1$ and $A_2$ are each independently $NR_m$, $A_1$ may be bonded to $R_4$ or $R_5$ to form a ring. In some embodiments, $A_2$ may be bonded to $R_7$ or $R_8$ to form a ring.

In an embodiment, the emission layer EML may include, as a dopant material, styryl derivatives (e.g., 1,4-bis[2-(3-N-ethylcarbazolyl) vinyl]benzene (BCzVB), 4-(di-p-tolylamino)-4'-[(di-p-tolylamino) styryl]stilbene (DPAVB), and N-(4-((E)-2-(6-((E)-4-(diphenylamino) styryl) naphthalen-2-yl) vinyl)phenyl)-N-phenylbenz enamine (N-BDAVBi), perylene and/or derivatives thereof (e.g., 2,5,8,11-tetra-t-butylperylene (TBP)), pyrene and/or derivatives thereof (e.g., 1,1-dipyrene, 1,4-dipyrenylbenzene, 1,4-bis(N,N-diphenylamino) pyrene), etc.

The emission layer EML may include any suitable phosphorescence dopant material. For example, a metal complex including iridium (Ir), platinum (Pt), osmium (Os), *aurum* (Au), titanium (Ti), zirconium (Zr), hafnium (Hf), europium (Eu), terbium (Tb), and/or thulium (Tm) may be utilized as a phosphorescence dopant. For example, iridium (III) bis(4,6-difluorophenylpyridinato-N, C2') picolinate (FIrpic), bis(2,4-difluorophenylpyridinato)-tetrakis(1-pyrazolyl) borate iridium (III) (Fir6), and/or platinum octaethyl porphyrin (PtOEP) may be utilized as a phosphorescence dopant. However, embodiments of the present disclosure are not limited thereto.

The emission layer EML may include a quantum dot material. The core of the quantum dot may be selected from among a Group II-VI compound, a Group III-V compound, a Group IV-VI compound, a Group IV element, a Group IV compound, and a combination thereof.

The Group II-VI compound may be selected from the group consisting of a binary compound selected from the group consisting of CdSe, CdTe, CdS, ZnS, ZnSe, ZnTe, ZnO, HgS, HgSe, HgTe, MgSe, MgS, and a mixture thereof, a ternary compound selected from the group consisting of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and a mixture thereof, and a quaternary compound selected from the group consisting of HgZnTeS, CdZnSeS, CdZnSeTe, CdZnSTe, CdHgSeS, CdHgSeTe, CdHgSTe, HgZnSeS, HgZnSeTe, HgZnSTe, and a mixture thereof.

The Group III-VI compound may include a binary compound (such as $In_2S_3$ and/or $In_2Se_3$), a ternary compound (such as $InGaS_3$ and/or $InGaSe_3$), or any combination thereof.

A Group I-III-VI compound may be selected from a ternary compound selected from the group consisting of AgInS, $AgInS_2$, CuInS, $CuInS_2$, $AgGaS_2$, $CuGaS_2$ $CuGaO_2$, $AgGaO_2$, $AgAlO_2$, and a mixture thereof, or a quaternary compound (such as $AgInGaS_2$ and/or $CuInGaS_2$).

The Group III-V compound may be selected from the group consisting of a binary compound selected from the group consisting of GaN, GaP, GaAs, GaSb, AlN, AlP, AlAs, AlSb, InN, InP, InAs, InSb, and a mixture thereof, a ternary compound selected from the group consisting of GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, InAsP, and a mixture thereof, and a quaternary compound selected from the group consisting of GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and a mixture thereof. In some embodiments, the Group III-V compound may further include a Group II metal. For example, InZnP, etc. may be selected as a Group III-II-V compound.

The Group IV-VI compound may be selected from the group consisting of a binary compound selected from the group consisting of SnS, SnSe, SnTe, PbS, PbSe, PbTe, and a mixture thereof, a ternary compound selected from the group consisting of SnSeS, SnSeTe, SnSTe, PbSeS, PbSeTe, PbSTe, SnPbS, SnPbSe, SnPbTe, and a mixture thereof, and a quaternary compound selected from the group consisting of SnPbSSe, SnPbSeTe, SnPbSTe, and a mixture thereof. The Group IV element may be selected from the group consisting of Si, Ge, and a mixture thereof. The Group IV compound may be a binary compound selected from the group consisting of SiC, SiGe, and a mixture thereof.

In this case, a binary compound, a ternary compound, or a quaternary compound may be present in a particle with a substantially uniform concentration distribution, or may be present in the same particle with a partially different concentration. In some embodiments, the quantum dot may have a core/shell structure in which one quantum dot surrounds another quantum dot. An interface between the core and the shell may have a concentration gradient in which the concentration of an element present in the shell becomes lower toward the center.

In some embodiments, a quantum dot may have the above-described core-shell structure including a core having nanocrystals and a shell surrounding the core. The shell of the quantum dot may serve as a protective layer to prevent or reduce the chemical deformation of the core so as to maintain semiconductor properties, and/or a charging layer to impart electrophoresis properties to the quantum dot. The shell may be a single layer or multiple layers. An interface between the core and the shell may have a concentration gradient in which the concentration of an element present in the shell becomes lower toward the center. An example of the shell of the quantum dot may include a metal or non-metal oxide, a semiconductor compound, or a combination thereof.

For example, the metal or non-metal oxide may be a binary compound (such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, and/or NiO), and/or a ternary compound (such as $MgAl_2O_4$, $CoFe_2O_4$, $NiFe_2O_4$, and/or $CoMn_2O_4$), but embodiments of the present disclosure are not limited thereto.

Also, the semiconductor compound may be, for example, CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, etc., but embodiments of the present disclosure are not limited thereto.

The quantum dot may have a full width of half maximum (FWHM) of a light emission wavelength spectrum of about 45 nm or less, about 40 nm or less, and for example about 30 nm or less, and color purity or color reproducibility may be improved in the above range. In some embodiments, light emitted through such a quantum dot is emitted in all directions, and thus a wide viewing angle may be achieved.

The form of the quantum dot is not particularly limited as long as it is a form commonly utilized in the art, and for example may have the form of spherical, pyramidal, multi-arm, and/or cubic nanoparticles, nanotubes, nanowires, nanofibers, nanoplate particles, etc..

The quantum dot may control the color of emitted light according to the particle size thereof. Accordingly, the quantum dot may have one or more suitable light emission colors (such as blue, red, and/or green).

Further, in an embodiment, the emission layer EML may include two dopant materials which have different lowest triplet exciton energy levels (T1 levels) from each other. The emission layer EML of the light emitting device ED of an embodiment may include a host having a first lowest triplet exciton energy level, a first dopant having a second lowest triplet exciton energy level lower than the first lowest triplet exciton energy level, and a second dopant having a third lowest triplet exciton energy level lower than the second lowest triplet exciton energy level.

In the light emitting device ED of an embodiment including a host, a first dopant, and a second dopant in the emission layer EML, the first dopant may be a delayed fluorescence dopant, and the second dopant may be a fluorescence dopant.

For example, when the emission layer EML of the light emitting device ED of an embodiment includes a plurality of dopants, the emission layer EML may include a first dopant and a second dopant (which are different from each other). For example, when the emission layer EML is to emit blue light, the emission layer EML may further include, as a second dopant, any one selected from the group consisting of spiro-DPVBi, spiro-6P, distyryl-benzene (DSB), distyryl-arylene (DSA), polyfluorene (PFO)-based polymer and poly (p-phenylene vinylene) (PPV)-based polymer. An organometallic complex or a metal complex (such as (4,6-$F_2$ppy)$_2$Irpic), perylene and/or derivatives thereof, etc. may be utilized as a second dopant.

In each light emitting device ED of embodiments illustrated in FIGS. 3 to 6, the electron transport region ETR is provided on the emission layer EML. The electron transport region ETR may include at least one of the hole blocking layer HBL, the electron transport layer ETL, or the electron injection layer EIL, but embodiments of the present disclosure are not limited thereto.

The electron transport region ETR may have a single layer formed of a single material, a single layer formed of a plurality of different materials, or a multilayer structure including a plurality of layers formed of a plurality of different materials.

For example, the electron transport region ETR may have a single layer structure of the electron injection layer EIL or the electron transport layer ETL, or may have a single layer structure formed of an electron injection material and an electron transport material. In some embodiments, the electron transport region ETR may have a single layer structure formed of a plurality of different materials, or may have a structure in which an electron transport layer ETL/electron injection layer EIL and a hole blocking layer HBL/electron transport layer ETL/electron injection layer EIL are stacked in order from the emission layer EML, but embodiments of the present disclosure are not limited thereto. The thickness of the electron transport region ETR may be, for example, about 1,000 Å to about 1,500 Å.

The electron transport region ETR may be formed by utilizing one or more suitable methods (such as a vacuum deposition method, a spin coating method, a cast method, a Langmuir-Blodgett (LB) method, an inkjet printing method, a laser printing method, and/or a laser induced thermal imaging (LITI) method).

For example, the electron transport layer ETL may include a compound represented by Formula ET-1:

Formula ET-1

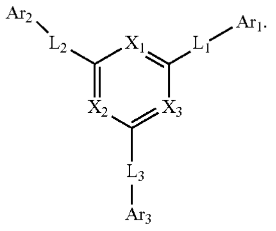

In Formula ET-1, at least one among $X_1$ to $X_3$ may be N, and the others may be $CR_a$. $R_a$ may be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. $Ar_1$ to $Ar_3$ may each independently be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In Formula ET-1, $L_1$ to $L_3$ may each independently be a direct linkage, a substituted or unsubstituted arylene group having 6 to 30 ring-forming carbon atoms, or a substituted or unsubstituted heteroarylene group having 2 to 30 ring-forming carbon atoms.

The electron transport region ETR may include an anthracene-based compound. However, embodiments of the present disclosure are not limited thereto, and the electron transport region ETR may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl) biphenyl-3-yl)-1,3,5-triazine, 2-(4-(N-phenylbenzimidazolyl-1-ylphenyl)-9,10-dinaphthylanthracene, 1,3,5-tri (1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), beryllium bis(benzoquinolin-10-olate ($Bebq_2$), 9,10-di(naphthalene-2-yl) anthracene (ADN), 1,3-bis[3,5-di(pyridin-3-yl)phenyl]benzene (BmPyPhB), or a mixture thereof.

In some embodiments, the electron transport regions ETR may include a metal halide (such as LiF, NaCl, CsF, RbCl, RbI, CuI, and/or KI), a lanthanide metal (such as Yb), or a co-deposited material of the metal halide and the lanthanide metal. For example, the electron transport region ETR may include KI: Yb, RbI: Yb, etc. as a co-deposited material. In some embodiments, the electron transport region ETR may be formed utilizing a metal oxide (such as $Li_2O$ and/or BaO), or 8-hydroxyl-lithium quinolate (LiQ), etc., but embodiments of the present disclosure are not limited thereto. The electron injection layer EIL may also be formed of a mixture material of an electron transport material and an insulating organometallic salt. The organometallic salt may be a material having an energy band gap of about 4 eV or more. The organometallic salt may include, for example, metal acetates, metal benzoates, metal acetoacetates, metal acetylacetonates, and/or metal stearates.

The electron transport region ETR may further include at least one of 2,9-dimethyl-4,7-diphenyl-1,10-phenanthroline (BCP), or 4,7-diphenyl-1,10-phenanthroline (Bphen) in addition to the above-described materials, but embodiments of the present disclosure are not limited thereto.

The electron transport region ETR may include the above-described compounds of the hole transport region in at least one of the electron injection layer EIL, the electron transport layer ETL, or the hole blocking layer HBL.

When the electron transport region ETR includes the electron transport layer ETL, the electron transport layer ETL may have a thickness of about 100 Å to about 1,000 Å, for example, about 150 Å to about 500 Å. When the thickness of the electron transport layer ETL satisfies the above-described range, satisfactory electron transport characteristics may be obtained without a substantial increase in driving voltage.

When the electron transport region ETR includes the electron injection layer EIL, the electron injection layer EIL may have a thickness of about 1 Å to about 100 Å, for example, about 3 Å to about 90 Å. When the thickness of the electron injection layer EIL satisfies the above-described range, satisfactory electron injection characteristics may be obtained without a substantial increase in driving voltage.

The second electrode EL2 is provided on the electron transport region ETR. The second electrode EL2 may be a common electrode. The second electrode EL2 may be a cathode or an anode, but embodiments of the present disclosure are not limited thereto. For example, when the first electrode EL1 is an anode, the second electrode EL2 may be a cathode, and when the first electrode EL1 is a cathode, the second electrode EL2 may be an anode.

The second electrode EL2 may be a transmissive electrode, a transflective electrode, or a reflective electrode. When the second electrode EL2 is a transmissive electrode, the second electrode EL2 may include a transparent metal oxide, for example, ITO, IZO, ZnO, ITZO, etc.

When the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, W, In, Zn, and Sn, a compound thereof, or a mixture thereof (e.g., a mixture of Ag and Mg), or at least one oxide thereof. The second electrode EL2 may be a multilayer structure including reflective film or a transflective film formed of the above-described materials, and a transparent conductive film formed of ITO, IZO, ZnO, ITZO, etc.

In some embodiments, the second electrode EL2 may be connected with an auxiliary electrode. When the second electrode EL2 is connected with the auxiliary electrode, the resistance of the second electrode EL2 may decrease.

In some embodiments, the light emitting device ED of an embodiment may further include a buffer layer between the emission layer EML and the electron transport region ETR. The buffer layer may control the concentration of excitons is generated in the emission layer EML. The buffer layer may include a part (e.g., some) of the emission layer EML materials. For example, the buffer layer may include host materials of the emission layer EML materials. The lowest triplet exciton energy level of the buffer layer material may be controlled to be higher than or equal to the lowest triplet exciton energy level of the second dopant or to be lower than or equal to the lowest triplet exciton energy level of the second dopant according to a combination of host and dopant materials included in the emission layer EML.

In some embodiments, the capping layer CPL may be disposed on the second electrode EL2 of the light emitting device ED of an embodiment. The capping layer CPL may include a multilayer or a single layer.

In an embodiment, the capping layer CPL may be an organic layer or an inorganic layer. For example, when the capping layer CPL includes an inorganic material, the inorganic material may include an alkaline metal compound (such as LiF), an alkaline earth metal compound (such as $MgF_2$, SiON, $SiN_x$, $SiO_y$), etc.

For example, when the capping layer CPL includes an organic material, the organic material may include α-NPD, NPB, TPD, m-MTDATA, $Alq_3$, CuPc, N4,N4, N4', N4'-tetra (biphenyl-4-yl) biphenyl-4,4'-diamine (TPD15), 4,4',4"-tris (carbazol-9-yl)triphenylamine (TCTA), etc., an epoxy resin, and/or an acrylate (such as methacrylate). However, embodiments of the present disclosure are not limited thereto, and the organic material may also include one or more of Compounds P1 to P5.

P1

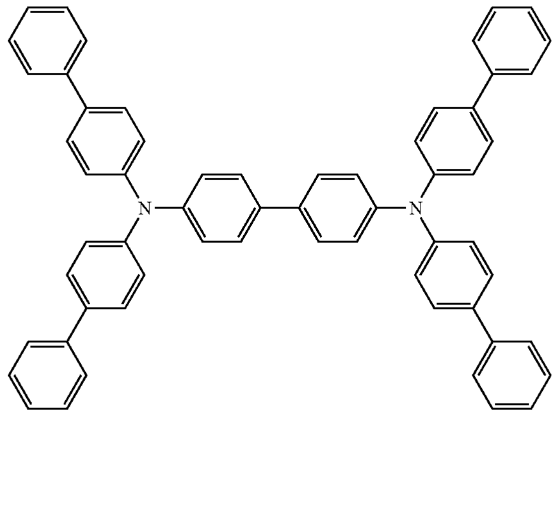

-continued

P2

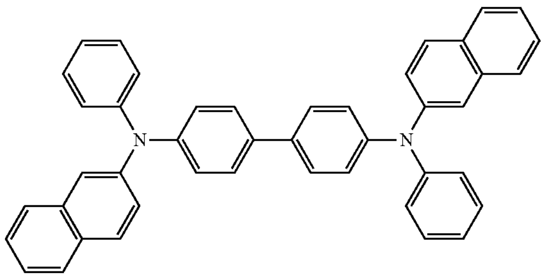

P3

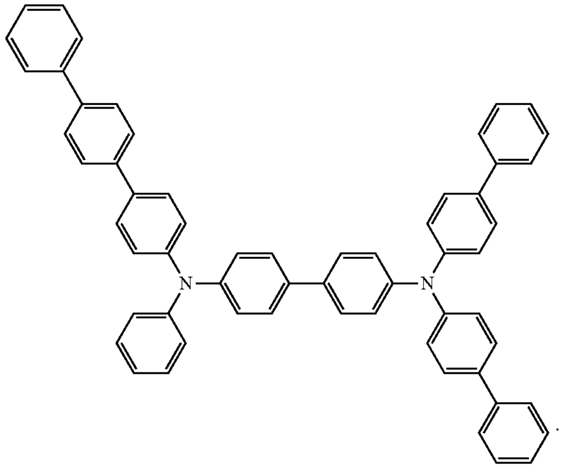

P4

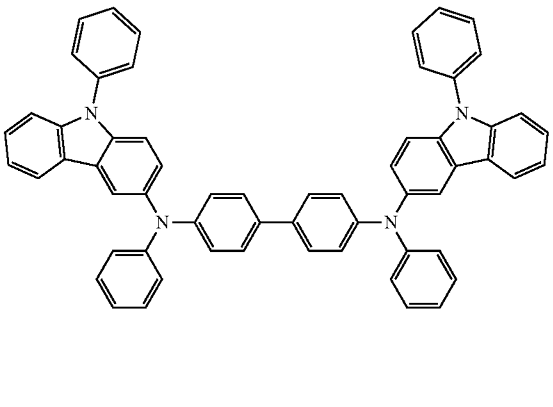

-continued

P5

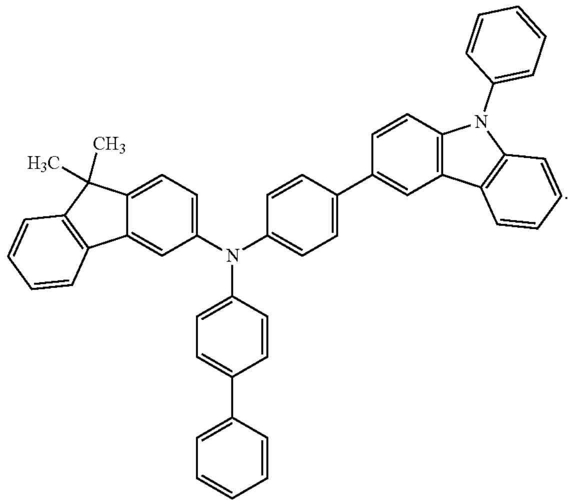

In some embodiments, the refractive index of the capping layer CPL may be about 1.6 or more. For example, the refractive index of the capping layer CPL may be about 1.6 or more with respect to light in a wavelength range of about 550 nm to about 660 nm.

The light emitting device ED according to an embodiment of the present disclosure may include the above-described amine compound of an embodiment in the hole transport region HTR disposed between the first electrode EL1 and the second electrode EL2 to exhibit high luminous efficiency and/or long service life characteristics.

In some embodiments, the above-described amine compound of an embodiment may be included as a material for the light emitting device ED in an organic layer in addition to the hole transport region HTR. For example, the light emitting device ED according to an embodiment of the present disclosure may include the above-described amine compound of an embodiment in at least one organic layer disposed between the first electrode EL1 and the second electrode EL2, or in the capping layer CPL disposed on the second electrode EL2.

The above-described amine compound of an embodiment includes the spirofluorene-indene group connected to the amine group, and may improve the ability of a hole transport between molecules compared to a typical compound, and when the amine compound is utilized as a hole transport material of the organic electroluminescence device, a long service life and high efficiency of the organic electroluminescence device may be achieved.

Figure 7:
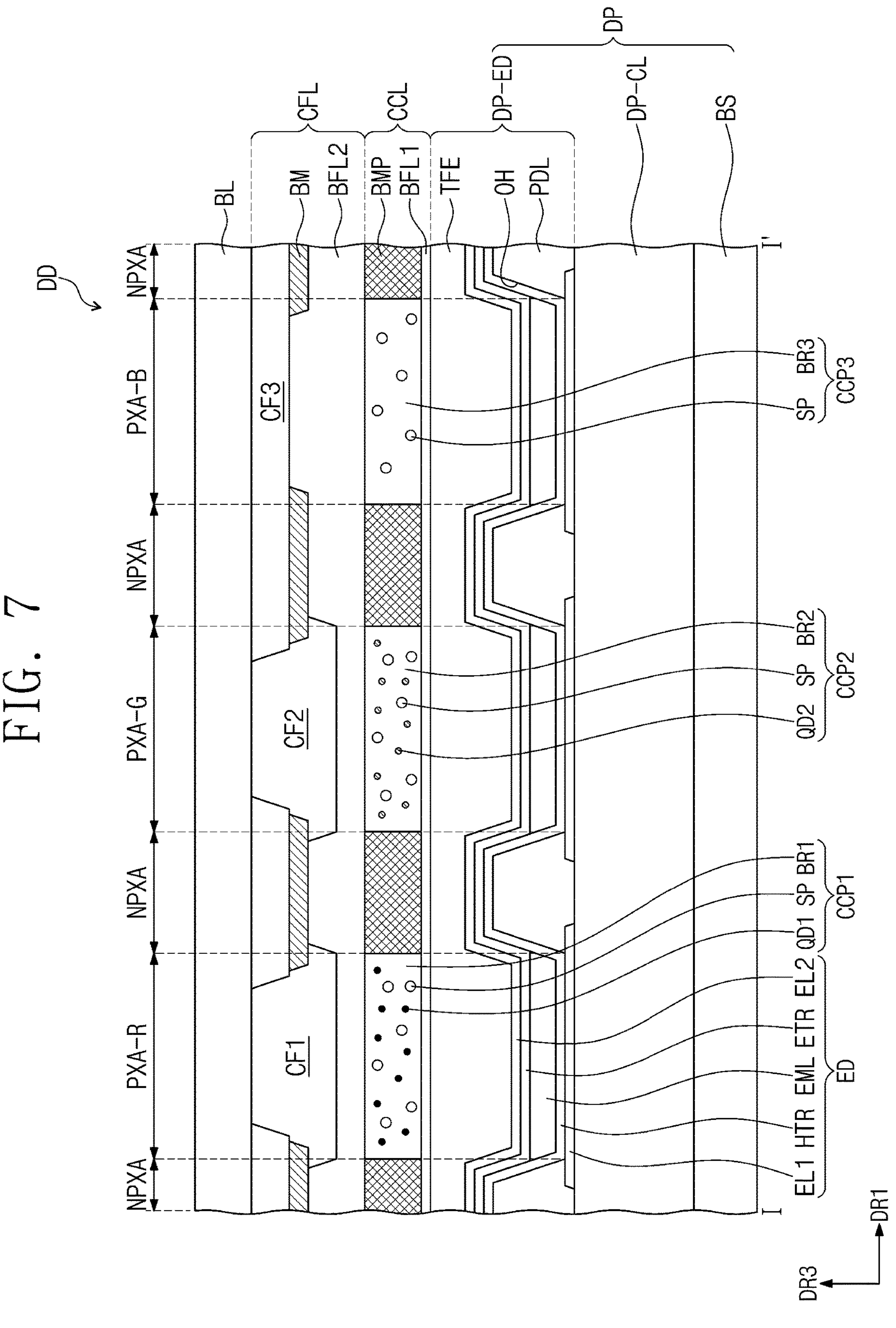
FIGS. 7 and 8 are each a cross-sectional view of a display apparatus according to an embodiment.
Figure 8:
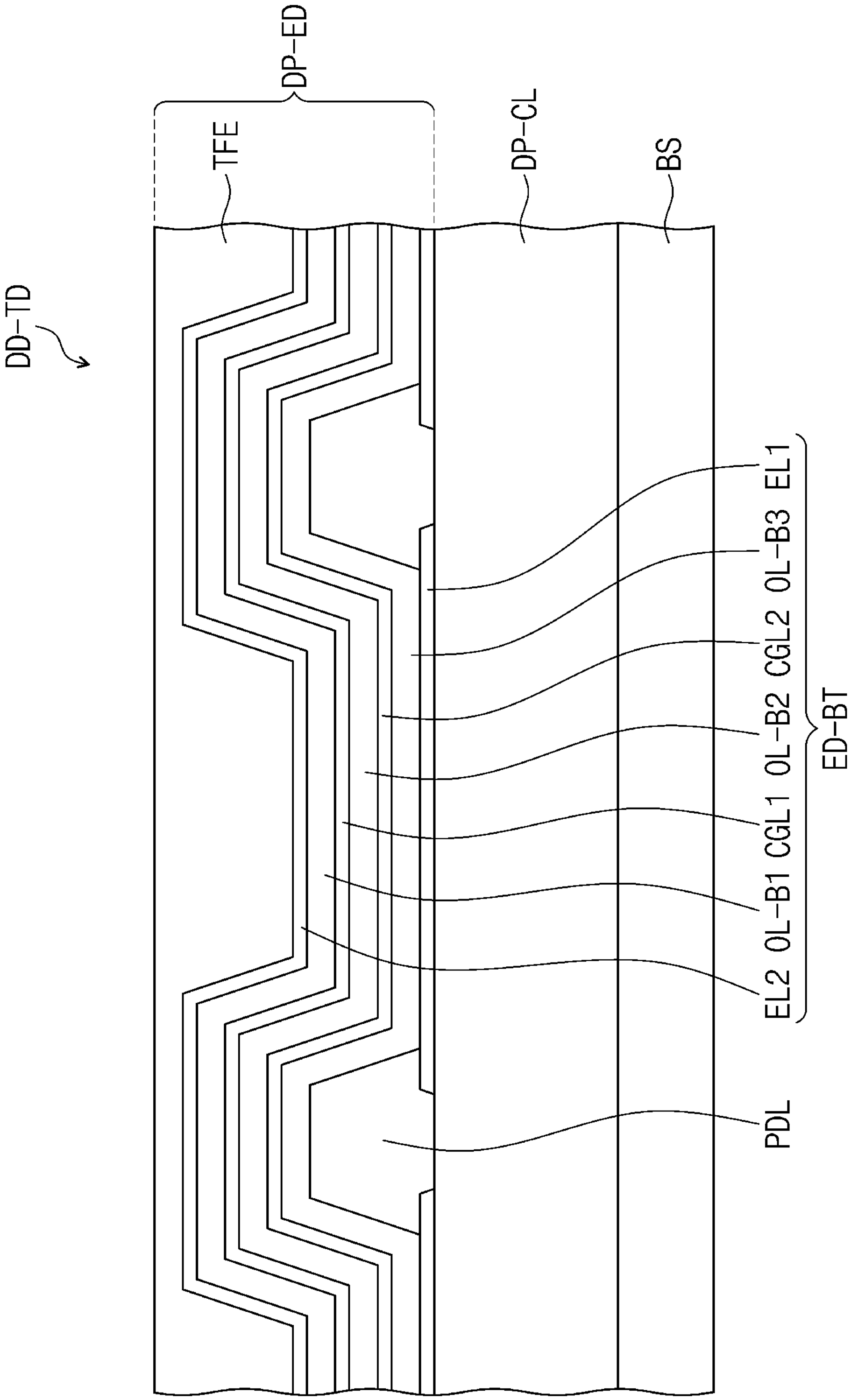

FIGS. 7 and 8 are each a cross-sectional view of a display apparatus according to an embodiment. Hereinafter, in describing the display apparatus of an embodiment with reference to FIGS. 7 and 8, the duplicated features which have been described in FIGS. 1 to 6 are not described again, but their differences will be mainly described.

Referring to FIG. 7, the display apparatus DD according to an embodiment may include a display panel DP including a display device layer DP-ED, a light control layer CCL disposed on the display panel DP, and a color filter layer CFL.

In an embodiment illustrated in FIG. 7, the display panel DP may include a base layer BS, a circuit layer DP-CL provided on the base layer BS, and the display device layer DP-ED, and the display device layer DP-ED may include a light emitting device ED.

The light emitting device ED may include a first electrode EL1, a hole transport region HTR disposed on the first electrode EL1, an emission layer EML disposed on the hole transport region HTR, an electron transport region ETR disposed on the emission layer EML, and a second electrode EL2 disposed on the electron transport region ETR. In some embodiments, the structures of the light emitting devices of FIGS. 3 to 6 as described above may be equally applied to the structure of the light emitting device ED shown in FIG. 7.

Referring to FIG. 7, the emission layer EML may be disposed in an opening OH defined in a pixel defining film PDL. For example, the emission layer EML which is divided by the pixel defining film PDL and provided corresponding to each light emitting regions PXA-R, PXA-G, and PXA-B may be to emit light in the same wavelength range. In the display apparatus DD of an embodiment, the emission layer EML may be to emit blue light. In some embodiments, the emission layer EML may be provided as a common layer in the entire light emitting regions PXA-R, PXA-G, and PXA-B.

The light control layer CCL may be disposed on the display panel DP. The light control layer CCL may include a light conversion body. The light conversion body may be a quantum dot, a phosphor, and/or the like. The light conversion body may be to emit light by converting the wavelength of provided light. For example, the light control layer CCL may include quantum dot and/or a phosphor.

The light control layer CCL may include a plurality of light control units CCP1, CCP2 and CCP3. The light control units CCP1, CCP2 and CCP3 may be spaced apart from each other along a first direction DR1.

Referring to FIG. 7, divided patterns BMP may be disposed between the light control units CCP1, CCP2 and CCP3, which are spaced apart from each other, but embodiments of the present disclosure are not limited thereto. FIG. 7 illustrates that the divided patterns BMP do not overlap the light control units CCP1, CCP2 and CCP3, but at least a portion of the edges of the light control units CCP1, CCP2 and CCP3 may overlap the divided patterns BMP.

The light control layer CCL may include a first light control unit CCP1 containing a first quantum dot QD1 to convert first color light provided from the light emitting device ED into second color light, a second light control unit CCP2 containing a second quantum dot QD2 to convert the first color light into third color light, and a third light control unit CCP3 to transmit the first color light.

In an embodiment, the first light control unit CCP1 may be to provide red light that is the second color light, and the second light control unit CCP2 may be to provide green light that is the third color light. The third light control unit CCP3 may be to transmit blue light that is the first color light provided in the light-emitting element ED. For example, the first quantum dot QD1 may be a red quantum dot, and the second quantum dot QD2 may be a green quantum dot. The same as described above may be applied with respect to the quantum dots QD1 and QD2.

In some embodiments, the light control layer CCL may further include a scatterer SP. The first light control unit CCP1 may include the first quantum dot QD1 and the scatterer SP, the second light control unit CCP2 may include the second quantum dot QD2 and the scatterer SP, and the third light control unit CCP3 may not include any quantum dot but include the scatterer SP.

The scatterer SP may be inorganic particles. For example, the scatterer SP may include at least one of $TiO_2$, ZnO, $Al_2O_3$, $SiO_2$, or hollow silica. The scatterer SP may include any one of $TiO_2$, ZnO, $Al_2O_3$, $SiO_2$, or hollow silica, or may be a mixture of at least two materials selected from among $TiO_2$, ZnO, $Al_2O_3$, $SiO_2$, and hollow silica.

The first light control unit CCP1, the second light control unit CCP2, and the third light control unit CCP3 may each include base resins BR1, BR2, and BR3 in which the quantum dots QD1 and QD2 and the scatterer SP are dispersed. In an embodiment, the first light control unit CCP1 may include the first quantum dot QD1 and the scatterer SP dispersed in a first base resin BR1, the second light control unit CCP2 may include the second quantum dot QD2 and the scatterer SP dispersed in a second base resin BR2, and the third light control unit CCP3 may include the scatterer SP dispersed in a third base resin BR3. The base resins BR1, BR2, and BR3 are media in which the quantum dots QD1 and QD2 and the scatterer SP are dispersed, and may be formed of one or more suitable resin compositions, which may be generally referred to as binders. For example, the base resins BR1, BR2, and BR3 may be acrylic-based resins, urethane-based resins, silicone-based resins, epoxy-based resins, etc. The base resins BR1, BR2, and BR3 may be transparent resins. In an embodiment, the first base resin BR1, the second base resin BR2, and the third base resin BR3 may each be the same as or different from each other.

The light control layer CCL may include a barrier layer BFL1. The barrier layer BFL1 may serve to prevent or reduce the penetration of moisture and/or oxygen (hereinafter, referred to as 'moisture/oxygen'). The barrier layer BFL1 may be disposed on the light control units CCP1, CCP2, and CCP3 to block or reduce the light control units CCP1, CCP2 and CCP3 from being exposed to moisture/oxygen. In some embodiments, the barrier layer BFL1 may cover the light control units CCP1, CCP2, and CCP3. In some embodiments, the barrier layer BFL1 may be provided between the light control units CCP1, CCP2, and CCP3 and the color filter layer CFL.

The barrier layers BFL1 and BFL2 may include at least one inorganic layer. For example, the barrier layers BFL1 and BFL2 may include an inorganic material. For example, the barrier layers BFL1 and BFL2 may include a silicon nitride, an aluminum nitride, a zirconium nitride, a titanium nitride, a hafnium nitride, a tantalum nitride, a silicon oxide, an aluminum oxide, a titanium oxide, a tin oxide, a cerium oxide, a silicon oxynitride, a metal thin film which secures a transmittance, etc. In some embodiments, the barrier layers BFL1 and BFL2 may further include an organic film. The barrier layers BFL1 and BFL2 may be formed of a single layer or a plurality of layers.

In the display apparatus DD of an embodiment, the color filter layer CFL may be disposed on the light control layer CCL. For example, the color filter layer CFL may be directly disposed on the light control layer CCL. In this case, the barrier layer BFL2 may not be provided.

The color filter layer CFL may include a light shielding unit BM and/or filters CF-B, CF-G, and/or CF-R. The color filter layer CFL may include a first filter CF1 configured to transmit the second color light, a second filter CF2 configured to transmit the third color light, and a third filter CF3 configured to transmit the first color light. For example, the first filter CF1 may be a red filter, the second filter CF2 may be a green filter, and the third filter CF3 may be a blue filter. The filters CF1, CF2, and CF3 may each include a polymeric photosensitive resin and a pigment or dye. The first filter CF1 may include a red pigment or dye, the second filter CF2 may include a green pigment or dye, and the third filter CF3 may include a blue pigment or dye. In some embodiments, embodiments of the present disclosure are not limited thereto, and the third filter CF3 may not include a pigment or dye. The third filter CF3 may include a polymeric photosensitive resin and may not include a pigment or dye. The third filter CF3 may be transparent. The third filter CF3 may be formed of a transparent photosensitive resin.

Furthermore, in an embodiment, the first filter CF1 and the second filter CF2 may each be a yellow filter. The first filter CF1 and the second filter CF2 may not be separated but be provided as one filter.

The light shielding unit BM may be a black matrix. The light shielding unit BM may include an organic light shielding material or an inorganic light shielding material containing a black pigment or dye. The light shielding unit BM may prevent or reduce light leakage, and may separate boundaries between the adjacent filters CF1, CF2, and $CF_3$. In some embodiments, the light shielding unit BM may be formed of a blue filter.

The first to third filters CF1, CF2, and CF3 may be disposed corresponding to the red light emitting region PXA-R, the green light emitting region PXA-G, and the blue light emitting region PXA-B, respectively.

An upper base layer BL may be disposed on the color filter layer CFL. The upper base layer BL may be a member which provides a base surface in which the color filter layer CFL, the light control layer CCL, and/or the like are disposed. The upper base layer BL may be a glass substrate, a metal substrate, a plastic substrate, etc. However, embodiments of the present disclosure are not limited thereto, and the upper base layer BL may be an inorganic layer, an organic layer, or a composite material layer. In some embodiments, the upper base layer BL may not be provided.

FIG. 8 is a cross-sectional view illustrating a part of a display apparatus according to an embodiment. FIG. 8 illustrates a cross-sectional view of a part corresponding to the display panel DP of FIG. 7. In the display apparatus DD-TD of an embodiment, the light emitting device ED-BT may include a plurality of light emitting structures OL-B1, OL-B2, and OL-B3. The light emitting device ED-BT may include a first electrode EL1 and a second electrode EL2 which face each other, and the plurality of light emitting structures OL-B1, OL-B2, and OL-B3 sequentially stacked in the thickness direction between the first electrode EL1 and the second electrode EL2. The light emitting structures OL-B1, OL-B2, and OL-B3 each may include an emission layer EML (FIG. 7) and a hole transport region HTR and an electron transport region ETR disposed with the emission layer EML (FIG. 7) therebetween.

For example, the light emitting device ED-BT included in the display apparatus DD-TD of an embodiment may be a light emitting device having a tandem structure and including a plurality of emission layers.

In an embodiment illustrated in FIG. 8, light emitted from each of the light emitting structures OL-B1, OL-B2, and OL-B3 may be blue light. However, embodiments of the present disclosure are not limited thereto, and the light emitted from each of the light emitting structures OL-B1, OL-B2, and OL-B3 may be in a wavelength range different from each other. For example, the light emitting device ED-BT including the plurality of light emitting structures OL-B1, OL-B2, and OL-B3 which emit light in a wavelength range different from each other may be to emit white light.

A charge generation layer CGL may be disposed between the neighboring light emitting structures OL-B1, OL-B2, and OL-B3. The charge generation layer CGL may include a p-type charge generation layer and/or an n-type charge generation layer.

Hereinafter, with reference to Examples and Comparative Examples, a compound according to embodiments of the present disclosure and an organic electroluminescence device of an embodiment will be described in more detail. The following embodiments are only illustrations to assist the understanding of the present disclosure, and the scope of the present disclosure is not limited thereto.

EXAMPLES

1. Synthesis of Amine Compound

First, a synthetic method of an amine compound according to the present embodiment will be described in more detail by illustrating a synthetic method of compounds 1, 15, 21, 25, and 61. The synthetic methods of the amine compound is provided as an example, but synthetic methods according to an embodiment of the present disclosure are not limited to Examples.

(1) Synthesis of Compound 1

Amine compound 1 according to an embodiment may be synthesized by, for example, the reaction below.

Reaction Scheme 1

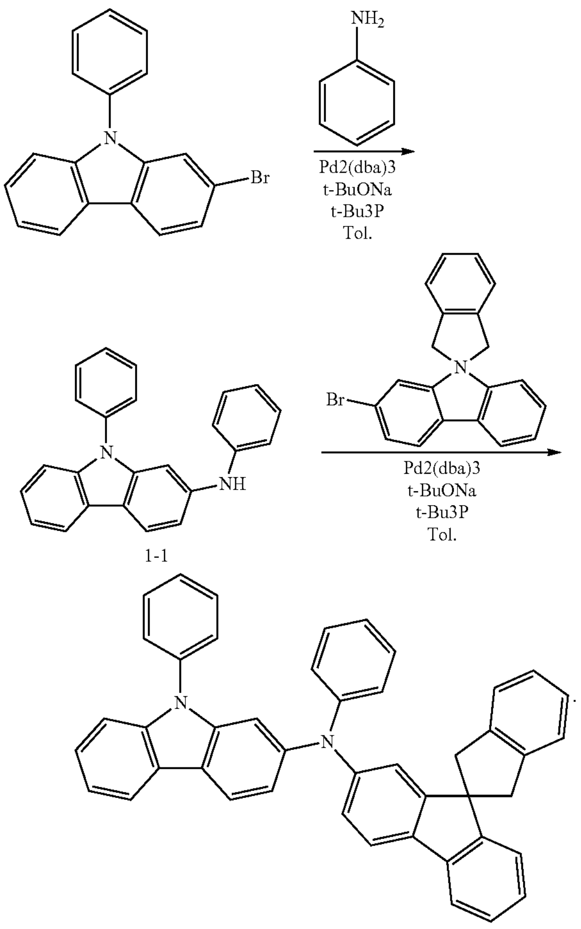

1-1

1

Synthesis of Intermediate Compound 1-1

2-bromo-9-phenyl-9H-carbazole (6.4 g), aniline (1.9 g), $Pd_2(dba)_3$ (0.9 g), t-BuONa (5.7 g), t-$Bu_3P$ (0.17 g), and toluene (250 mL) were added to a 1-neck round flask and stirred at 100° C. for 2 hours. The reactant was subjected to work-up with ethyl acetate (EA)/$H_2O$, and then separated by utilizing column chromatography to thus obtain *Intermedia* Compound 1-1 (4.7 g, yield: 72%, purity: 98%).

Synthesis of Compound 1

Intermediate Compound 1-1 (3.4 g), 2-bromo-1',3'-dihydrospiro[fluorene-9,2'-indene] (3.8 g), $Pd_2(dba)_3$ (0.45 g), t-BuONa (2.8 g), t-$Bu_3P$ (0.1 g), and toluene (150 mL) were added to a 1-neck round flask and stirred at 100° C. for 2 hours. The reactant was subjected to work-up with EA/$H_2O$, and then separated by utilizing column chromatography to thus obtain Compound 1 (4.5 g, yield: 75%, purity: 98%). Thereafter, the obtained Compound 1 was further purified by ether recrystallization, and when the purity became 99.8% or higher, sublimation purification was carried out to finally obtain Compound 1 (3.8 g, purity: 99.9% or higher).

(2) Synthesis of Compound 15

Amine compound 15 according to an embodiment may be synthesized by, for example, the following reaction.

Reaction Scheme 2

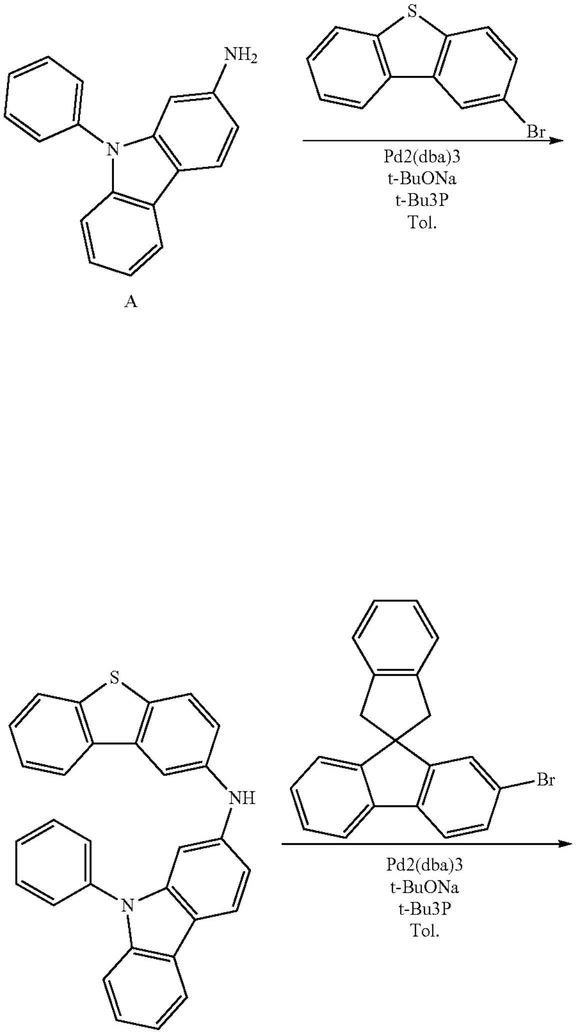

A 15-1

-continued

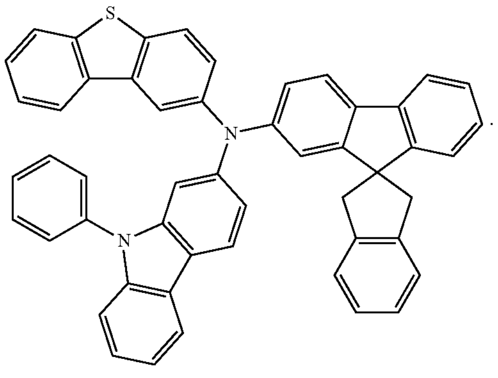

15

Synthesis of Intermediate Compound 15-1

9-phenyl-9H-carbazol-2-amine (5.1 g), 2-bromodibenzo[b,d]thiophene (5.2 g), $Pd_2(dba)_3$ (0.9 g), t-BuONa (5.7 g), t-$Bu_3P$ (0.17 g), and toluene (250 mL) were added to a 1-neck round flask and stirred at 100° C. for 2 hours. The reactant was subjected to work-up with EA/$H_2O$, and then separated by utilizing column chromatography to thus obtain Intermediate Compound 15-1 (5.6 g, yield: 64%, purity: 98%).

Synthesis of Compound 15

Intermediate Compound 15-1 (4.4 g), 2-bromo-1',3'-dihydrospiro[fluorene-9,2'-indene] (3.8 g), $Pd_2(dba)_3$ (0.45 g), t-BuONa (2.8 g), t-$Bu_3P$ (0.1 g), and toluene (150 mL) were added to a 1-neck round flask and stirred at 100° C. for 2 hours. The reactant was subjected to work-up with EA/$H_2O$, and then separated by utilizing column chromatography to thus obtain Compound 15 (4.6 g, yield: 66%, purity: 98%). Thereafter, the obtained Compound 15 was further purified by ether recrystallization, and when the purity became 99.8% or higher, sublimation purification was carried out to finally obtain Compound 15 (4.0 g, purity: 99.9% or higher).

(3) Synthesis of Compound 21

Amine compound 21 according to an embodiment may be synthesized by, for example, the reaction below.

Reaction Scheme 3

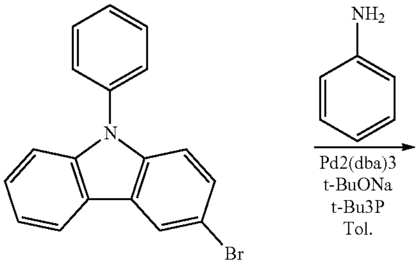

A

-continued

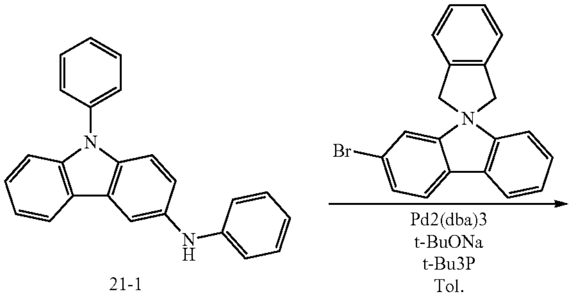

21-1

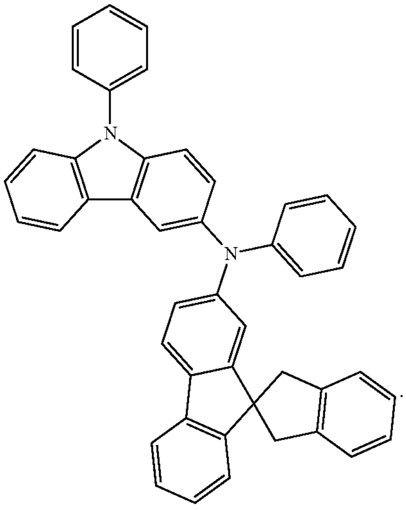

21

Synthesis of Intermediate Compound 21-1

3-bromo-9-phenyl-9H-carbazole (6.4 g), aniline (1.9 g), $Pd_2(dba)_3$ (0.9 g), t-BuONa (5.7 g), t-$Bu_3P$ (0.17 g), and toluene (250 mL) were added to a 1-neck round flask and stirred at 100° C. for 2 hours. The reactant was subjected to work-up with EA/$H_2O$, and then separated by utilizing column chromatography to thus obtain Intermediate Compound 21-1 (4.5 g, yield: 69%, purity: 98%).

Synthesis of Compound 21

Intermediate Compound 21-1 (3.4 g), 2-bromo-1',3'-dihydrospiro[fluorene-9,2'-indene] (3.8 g), $Pd_2(dba)_3$ (0.45 g), t-BuONa (2.8 g), t-$Bu_3P$ (0.1 g), and toluene (150 mL) were added to a 1-neck round flask and stirred at 100° C. for 2 hours. The reactant was subjected to work-up with EA/$H_2O$, and then separated by utilizing column chromatography to thus obtain Compound 21 (4.2 g, yield: 70%, purity: 98%). Thereafter, the obtained Compound 21 was further purified by ether recrystallization, and when the purity became 99.8% or higher, sublimation purification was carried out to finally obtain Compound 21 (3.5 g, purity: 99.9% or higher).

(4) Synthesis of Compound 25

Amine compound 25 according to an embodiment may be synthesized by, for example, the following reaction.

Reaction Scheme 4

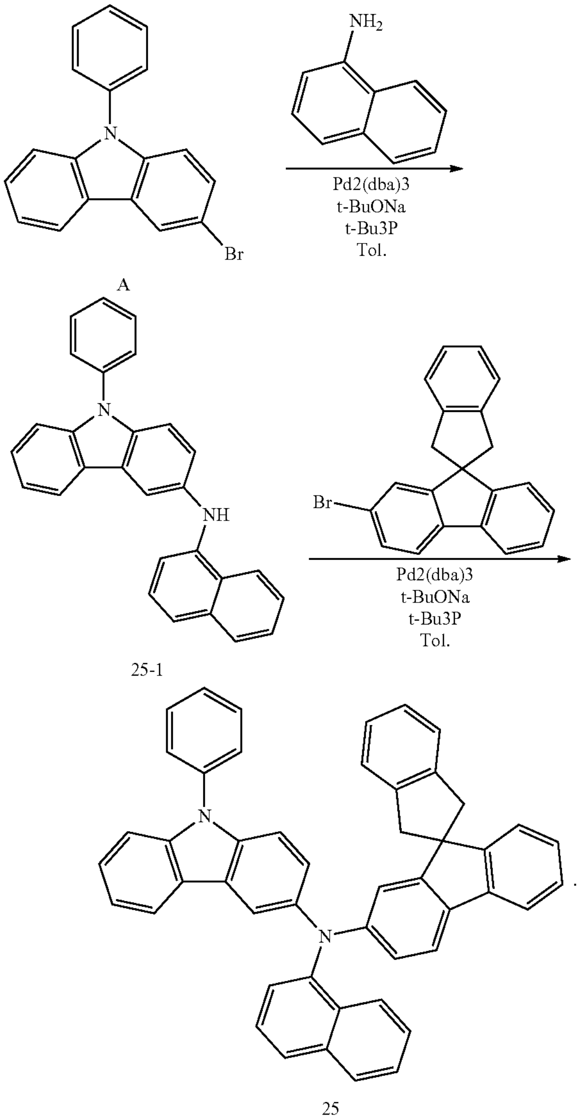

A 25-1

25

Synthesis of Intermediate Compound 25-1

3-bromo-9-phenyl-9H-carbazole (6.4 g), naphthalen-1-amine (2.8 g), $Pd_2(dba)_3$ (0.9 g), t-BuONa (5.7 g), t-$Bu_3P$ (0.17 g), and toluene (250 mL) were added to a 1-neck round flask and stirred at 100° C. for 2 hours. The reactant was subjected to work-up with EA/$H_2O$, and then separated by utilizing column chromatography to thus obtain Intermediate Compound 25-1 (4.9 g, yield: 64%, purity: 98%).

Synthesis of Compound 25

Intermediate Compound 25-1 (3.8 g), 2-bromo-1',3'-dihydrospiro[fluorene-9,2'-indene] (3.8 g), $Pd_2(dba)_3$ (0.45 g), t-BuONa (2.8 g), t-$Bu_3P$ (0.1 g), and toluene (150 mL) were added to a 1-neck round flask and stirred at 100° C. for 2 hours. The reactant was subjected to work-up with EA/$H_2O$, and then separated by utilizing column chromatography to thus obtain Compound 25 (4.2 g, yield: 64%, purity: 98%). Thereafter, the obtained Compound 25 was further purified by ether recrystallization, and when the purity became 99.8% or higher, sublimation purification was carried out to finally obtain Compound 25 (3.7 g, purity: 99% or higher).

(5) Synthesis of Compound 61

Amine compound 61 according to an embodiment may be synthesized by, for example, the reaction below.

Reaction Scheme 5

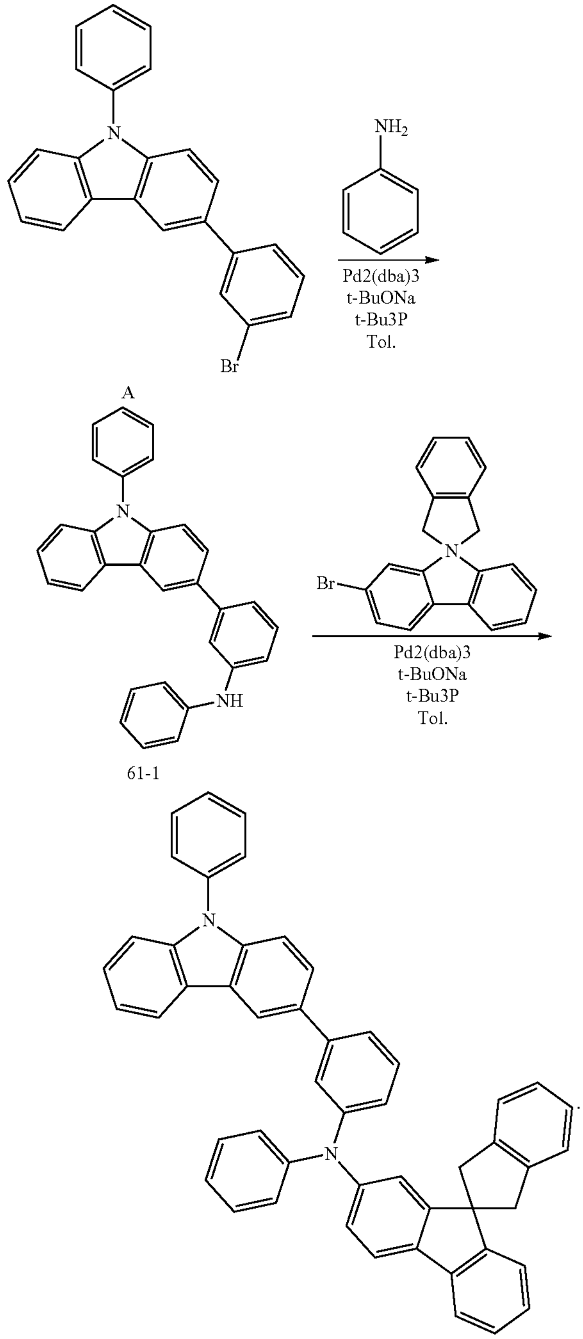

A 61-1

61

Synthesis of Intermediate Compound 61-1

3-(3-bromophenyl)-phenyl-9H-carbazole (6.8 g), aniline (1.9 g), $Pd_2(dba)_3$ (0.9 g), t-BuONa (5.7 g), t-$Bu_3P$ (0.17 g), and toluene (250 mL) were added to a 1-neck round flask and stirred at 100° C. for 2 hours. The reactant was subjected to work-up with EA/$H_2O$, and then separated by utilizing column chromatography to thus obtain Intermediate Compound 61-1 (5.3 g, yield: 65%, purity: 98%).

Synthesis of Compound 61

Intermediate Compound 61-1 (4.1 g), 2-bromo-1',3'-dihydrospiro[fluorene-9,2'-indene] (3.8 g), $Pd_2(dba)_3$ (0.45 g), t-BuONa (2.8 g), t-$Bu_3P$ (0.1 g), and toluene (150 mL) were added to a 1-neck round flask and stirred at 100° C. for 2 hours. The reactant was subjected to work-up with EA/$H_2O$, and then separated by utilizing column chromatography to thus obtain Compound 61 (4.7 g, yield: 70%, purity: 98%). Thereafter, the obtained Compound 61 was further purified by ether recrystallization, and when the purity became 99.8% or higher, sublimation purification was carried out to finally obtain Compound 61 (4.0 g, purity: 99.9% or higher).

2. Manufacture and Evaluation of Organic Electroluminescence Device Including Amine Compound Manufacture of Organic Electroluminescence Device The organic electroluminescence device of an embodiment including the amine compound of an embodiment in a hole transport layer was manufactured as follows. The example amine compounds of Compound 1, Compound 15, Compound 21, Compound 25, and Compound 61, as described above, were utilized as a hole transport layer material to manufacture the respective organic electroluminescence devices of Examples 1 to 5. Comparative Examples 1 to 5 correspond to organic electroluminescence devices manufactured by utilizing Comparative Example Compounds C1 to C5, respectively, as a hole transport layer material.

An ITO glass substrate of about 15 Ω/$cm^2$ (about 1,200 Å) of Corning Co. was cut to a size of 50 mm×50 mm×0.7 mm, washed with isopropyl alcohol and pure water, and cleansed by ultrasonic waves for about 5 minutes, and then irradiated with ultraviolet rays for about 30 minutes and treated with ozone. Then, (4,4',4"-tris {N,-(2-naphthyl)-N-phenylamino}-triphenylamine (2-TNATA) was deposited in vacuum to form a 600 Å-thick hole injection layer, and the Example Compound or Comparative Example Compound was deposited in vacuum to form a 300 Å-thick hole transport layer.

On the hole transport layer, 9,10-di(naphthalen-2-yl) anthracene (DNA) and 4,4'-bis[2-(4-(N, N-diphenylamino) phenyl) vinyl]biphenyl (DPAVBi) as blue fluorescence hosts were co-deposited in a ratio (e.g., amount) of 98:2 to form a 300 Å-thick emission layer.

On the emission layer, a 300 Å-thick electron transport layer was formed with tris(8-hydroxyquinolino)aluminum ($Alq_3$), and then LiF was deposited to form a 10 Å-thick electron injection layer. On the electron injection layer, a 3000 Å-thick second electrode was formed with aluminum (Al).

Compounds utilized for manufacturing the organic electroluminescence devices of Examples and Comparative Examples are disclosed below.

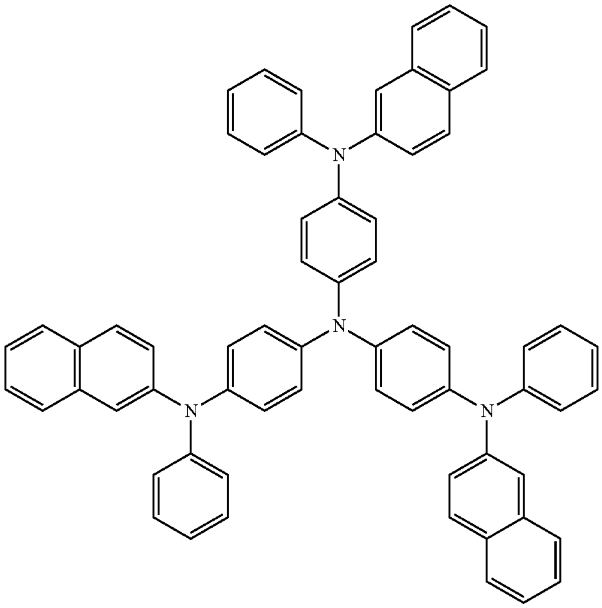

2-TNATA

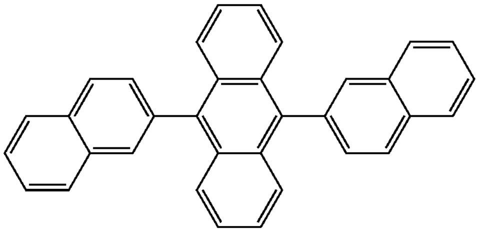

DNA

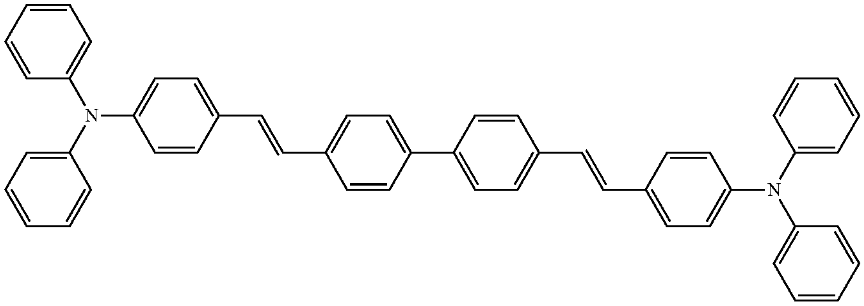

DPAVBi

-continued
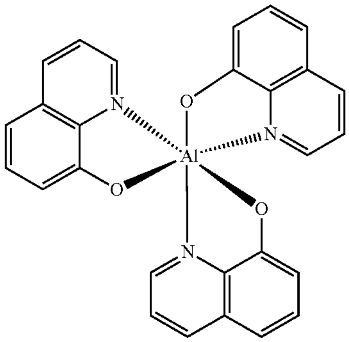
Alq3
1
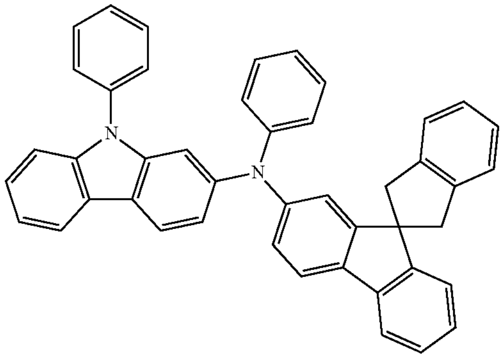
15
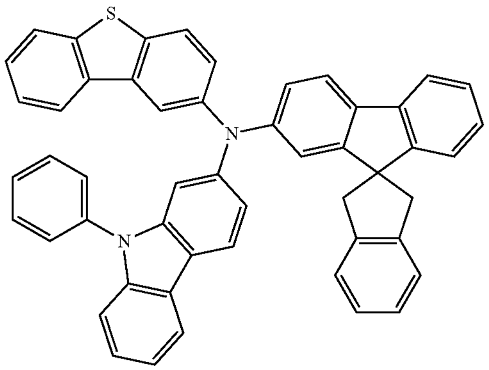
21
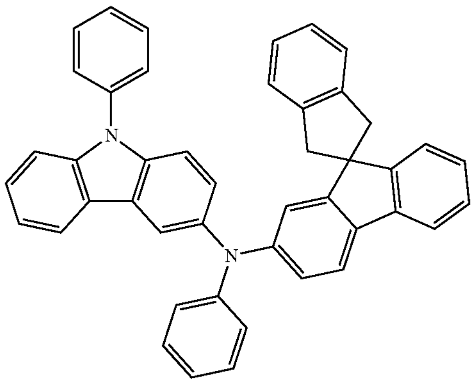
25
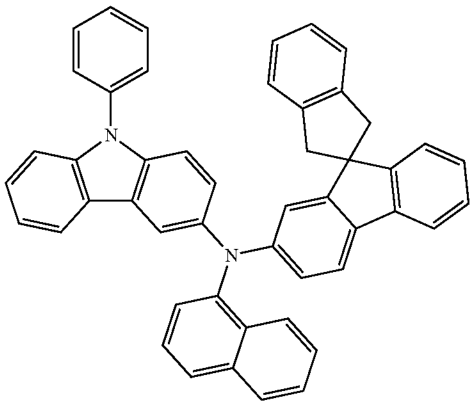

-continued

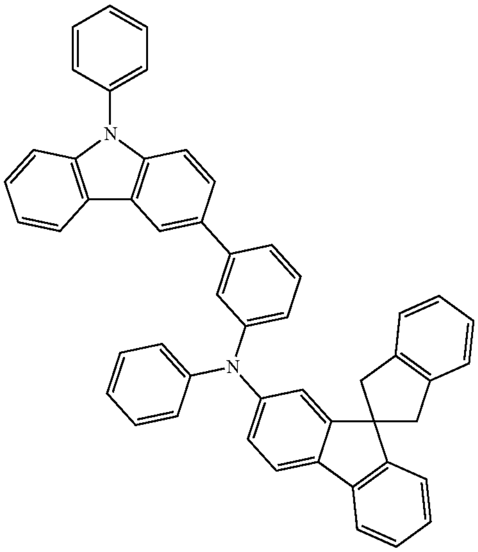

61

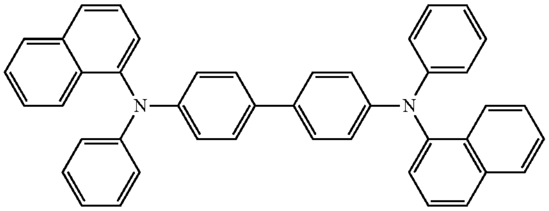

C1

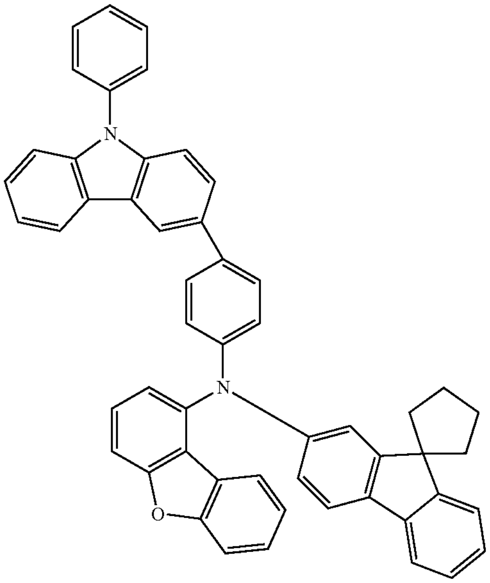

C2

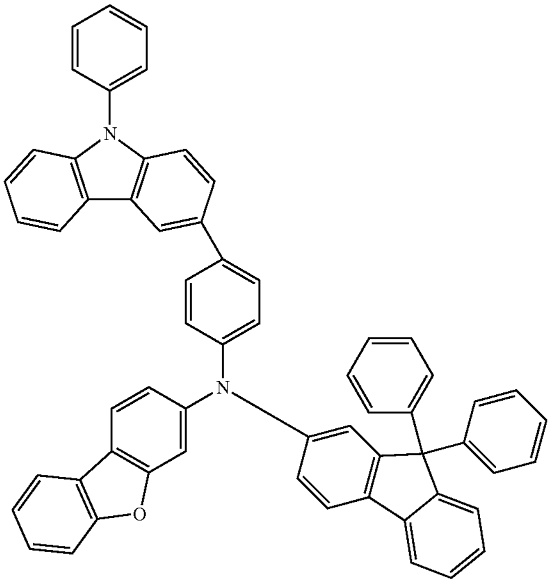

C3

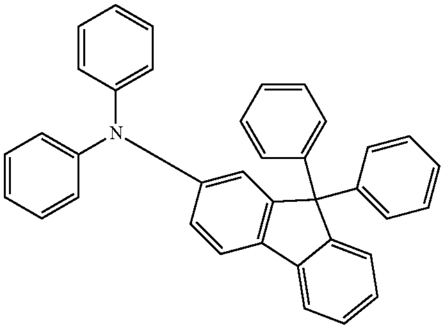

C4

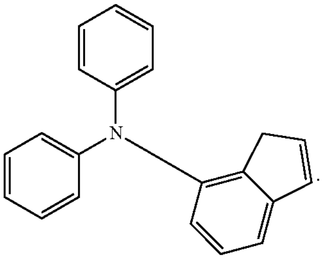

C5

Evaluation of Organic Electroluminescence Device Characteristics

Evaluation results of the organic electroluminescence devices of Examples 1 to 5 and Comparative Examples 1 to 5 are listed in Table 1. Driving voltage, brightness, luminous efficiency and a half service life of each of the manufactured organic electroluminescence devices are listed in comparison in Table 1.

In the evaluation results of the characteristics of Examples and Comparative Examples listed in Table 1, driving voltage and current density were measured by utilizing SourceMeter (Keithley Instruments, Inc., 2400 series), and external quantum efficiency (EQE) was measured by utilizing an external quantum efficiency measurement apparatus, C9920-12 (Hamamatsu Photonics, Co., Japan). The emitting efficiency shows a current efficiency value with respect to a current density of 50 mA/$cm^2$.

TABLE 1

| Device manufactured examples | Hole transport layer material | Driving voltage (V) | Brightness ($cd/m^2$) | Emitting efficiency (cd/A) | Half service life (hr) | Luminous color |
|---|---|---|---|---|---|---|
| Example 1 | Compound 1 | 3.94 | 3744 | 7.48 | 394 | Blue |
| Example 2 | Compound 15 | 3.86 | 3726 | 7.45 | 382 | Blue |
| Example 3 | Compound 21 | 3.91 | 3658 | 7.31 | 391 | Blue |
| Example 4 | Compound 25 | 3.92 | 3691 | 7.38 | 384 | Blue |
| Example 5 | Compound 61 | 3.88 | 3712 | 7.42 | 373 | Blue |
| Comparative Example 1 | Comparative Example Compound C1 | 7.01 | 2645 | 5.29 | 258 | Blue |
| Comparative Example 2 | Comparative Example Compound C2 | 4.65 | 3207 | 6.41 | 314 | Blue |
| Comparative Example 3 | Comparative Example Compound C3 | 4.79 | 3214 | 6.42 | 307 | Blue |
| Comparative Example 4 | Comparative Example Compound C4 | 4.42 | 2985 | 5.97 | 296 | Blue |
| Comparative Example 5 | Comparative Example Compound C5 | 4.83 | 2947 | 5.88 | 329 | Blue |

Referring to the results of Table 1, it may be seen that the Examples of the organic luminescence devices, which utilize the amine compound according to an embodiment of the present disclosure as a hole transport layer material, exhibit low driving voltage, relatively higher brightness, luminous efficiency, and high external quantum efficiency while emitting the same blue light, when compared to Comparative Examples. The amine compounds of the Examples have high stability by the spirofluorene-indene group substituted at the amine group in an arylamine-based hole transport material. Accordingly, the organic electroluminescence devices of Examples may exhibit improved luminous efficiency and longer service life compared to the organic electroluminescence devices of Comparative Examples. For example, the organic electroluminescence device of an example may achieve high luminous efficiency and a long service life in a blue light wavelength range by including the amine compound of an example as a hole transport material.

It may be seen that the amine compound of Comparative Example Compound C1, which does not include a fluorene group, has decreased hole transport characteristics compared to the Example Compounds, and thus the organic electroluminescence device of Comparative Example 1 exhibits high driving voltage, low brightness, low efficiency, and low half service life compared to the organic electroluminescence devices of Examples. Moreover, it may be seen that the amine compound of Comparative Example Compound C2, which includes the spirofluorene group but not the indene group moiety in the spirofluorene group has decreased hole transport characteristics compared to the Example Compounds, and thus the organic electroluminescence device of Comparative Example 2 exhibits high driving voltage, low brightness, low efficiency, and low half service life compared to the organic electroluminescence devices of the Examples. Likewise, it may be seen that Comparative Example Compounds C3 and C4, which are amine compounds including a fluorene group without the spiro structure, and Comparative Example Compound C5, which is an amine compound including only a simple indene group, have decreased hole transport characteristics compared to the Example Compounds, and thus the organic electroluminescence devices of Comparative Examples 3 to 5 exhibit high driving voltage, low brightness, low efficiency, and low half service life compared to the organic electroluminescence devices of the Examples.

The organic electroluminescence device of an embodiment may exhibit improved device characteristics with a low driving voltage, a high efficiency, and/or a long service life.

The amine compound of an embodiment may be included in a hole transport region of the organic electroluminescence device to contribute to high efficiency and/or a long service life of the organic electroluminescence device.

Although the present disclosure has been described with reference to embodiments of the present disclosure, it will be understood that the present disclosure should not be limited to these embodiments, and that various suitable changes and modifications can be made by those skilled in the art without departing from the spirit and scope of the present disclosure.

As used herein, the terms “substantially,” “about,” and similar terms are used as terms of approximation and not as terms of degree, and are intended to account for the inherent deviations in measured or calculated values that would be recognized by those of ordinary skill in the art.

Any numerical range recited herein is intended to include all sub-ranges of the same numerical precision subsumed within the recited range. For example, a range of “1.0 to 10.0” is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Accordingly, the technical scope of the present disclosure is not intended to be limited to the contents set forth in the detailed description of the specification, but is intended to be defined by the appended claims and equivalents thereof.

What is claimed is:

1. An organic electroluminescence device comprising:

a first electrode;

a second electrode facing the first electrode; and a plurality of organic layers between the first electrode and the second electrode, wherein, at least one of the plurality of organic layers comprises an amine compound comprising one amine group, the one amine group having an N atom connected to $Ar_1$, $Ar_2$, and a spirofluorene-indene group, the N atom is connected to one benzene ring of a fluorene group moiety of the spirofluorene-indene group, $Ar_2$ is an unsubstituted N-phenyl carbazole group or an unsubstituted N-fluorophenyl carbazole group, and is connected to the N atom at a 2nd carbon position or a 3rd carbon position of the carbazole group, $Ar_2$ is connected to the N atom through an unsubstituted phenylene linker, and $Ar_1$ is a substituted or unsubstituted aryl group having 10 to 30 ring-forming carbon atoms, or a substituted or unsubstituted heteroaryl group having 2 to 30 ring-forming carbon atoms, $Ar_1$ is a substituted or unsubstituted aryl group having 6 to 30 ring-forming carbon atoms, or a substituted or unsubstituted heteroaryl group having 2 to 30 ring-forming carbon atoms.

2. The organic electroluminescence device of claim 1, wherein the spirofluorene-indene group and the carbazole group are each independently bonded to the amine group via a linker, or directly bonded to the amine group.

3. The organic electroluminescence device of claim 1, wherein the plurality of organic layers comprise:

a hole transport region on the first electrode;

an emission layer on the hole transport region; and an electron transport region on the emission layer, and wherein the hole transport region comprises the amine compound.

4. The organic electroluminescence device of claim 3, wherein the hole transport region comprises:

a hole injection layer on the first electrode; and a hole transport layer on the hole injection layer, and wherein the hole transport layer comprises the amine compound.

5. The organic electroluminescence device of claim 3, wherein the hole transport region comprises a plurality of organic hole transport layers, wherein the organic hole transport layer among the plurality of organic hole transport layers that is adjacent to the emission layer comprises the amine compound.

6. An organic electroluminescence device comprising:

a first electrode;

a second electrode facing the first electrode; and a plurality of organic layers between the first electrode and the second electrode, wherein at least one organic layer among the plurality of organic layers comprises an amine compound comprising one amine group, the amine compound represented by Formula 4-1 or Formula 4-2:

Formula 4-1

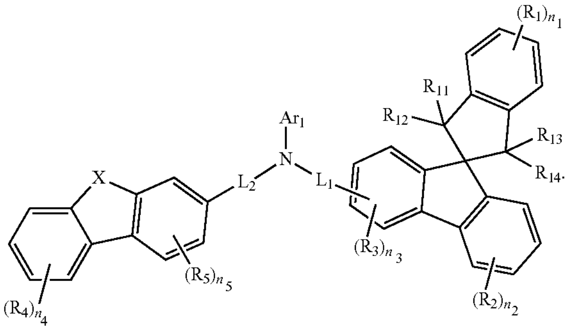

Formula 4-2

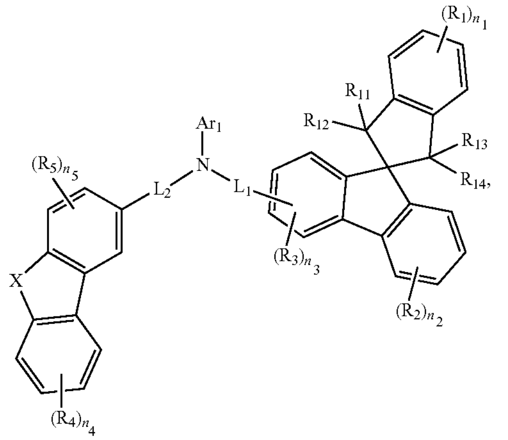

and wherein, in Formula 4-1 and Formula 4-2,

X is $NAr_3$, $Ar_3$ is an unsubstituted phenyl group or an unsubstituted fluorophenyl group, $Ar_1$ is a substituted or unsubstituted aryl group having 10 to 30 ring-forming carbon atoms, or a substituted or unsubstituted heteroaryl group having 2 to 30 ring-forming carbon atoms, $L_1$ is a direct linkage, a substituted or unsubstituted arylene group having 6 to 30 ring-forming carbon atoms, or a substituted or unsubstituted heteroarylene group having 2 to 30 ring-forming carbon atoms, $L_2$ is an unsubstituted phenylene group, $R_1$ to $R_3$ are each independently a hydrogen atom, a deuterium atom, a halogen atom, or a substituted or unsubstituted alkyl group having 1 to 20 carbon atoms, $R_4$ and $R_5$ are each independently a hydrogen atom or a deuterium atom, $R_{11}$ to $R_{14}$ are each independently a hydrogen atom, a deuterium atom, a halogen atom, or a substituted or unsubstituted alkyl group having 1 to 20 carbon atoms, $n_1$, $n_2$, and $n_4$ are each independently an integer of 0 to 4, and $n_3$ and $n_5$ are each independently an integer of 0 to 3.

7. The organic electroluminescence device of claim 6, wherein the amine compound is represented by any one among Formula 5-2 to Formula 5-3:

Formula 5-2

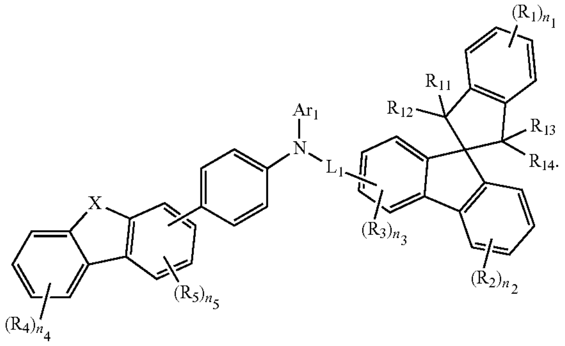

Formula 5-3

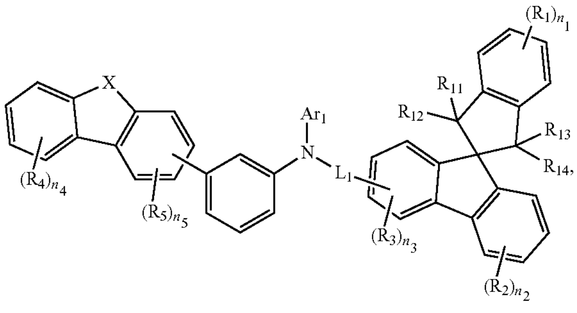

and wherein, in Formula 5-2 and Formula 5-3, $R_6$ is a hydrogen atom or a deuterium atom, $n_6$ is an integer of 0 to 4, and $Ar_1$, X, $L_1$, $R_1$, $R_2$, $R_3$, $R_4$, $R_5$, $R_{11}$, $R_{12}$, $R_{13}$, $R_{14}$, $n_1$, $n_2$, $n_3$, $n_4$, and $n_5$ are each independently the same as defined in Formula 4-1 and Formula 4-2.

8. The organic electroluminescence device of claim 6, wherein $Ar_1$ is a substituted or unsubstituted naphthyl group, a substituted or unsubstituted fluorenyl group, a substituted or unsubstituted carbazole group, a substituted or unsubstituted dibenzofuran group, or a substituted or unsubstituted dibenzothiophene group.

9. The organic electroluminescence device of claim 6, wherein the amine compound is at least one selected from among compounds represented by Compound Group 1:

42

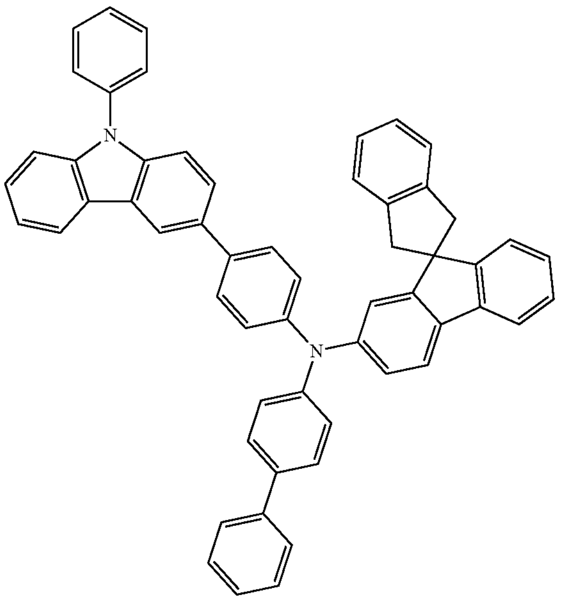

43

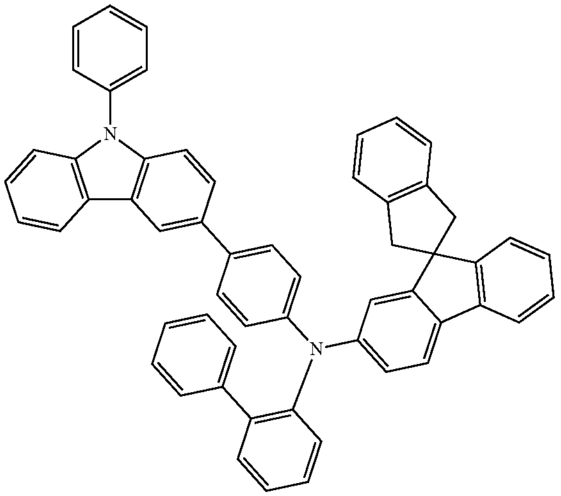

44

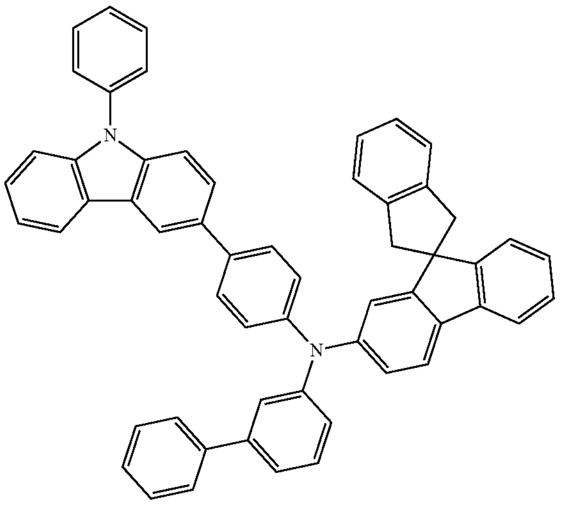

-continued
45
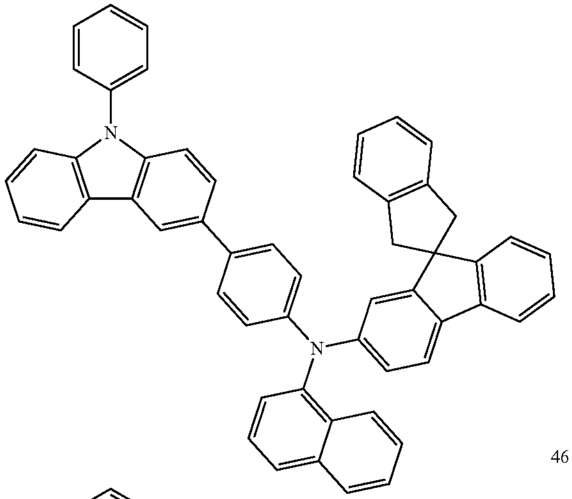
46
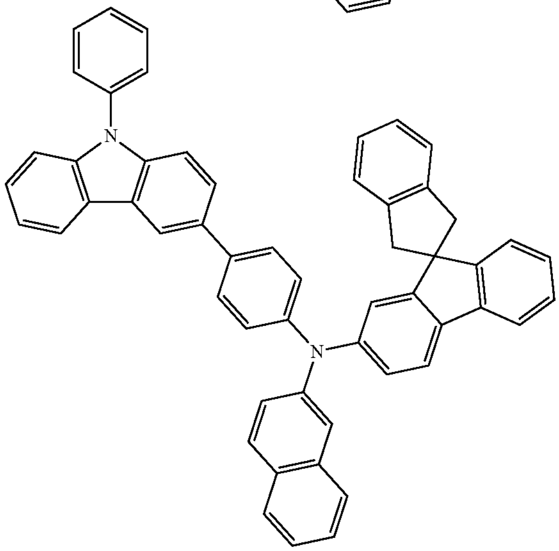
47
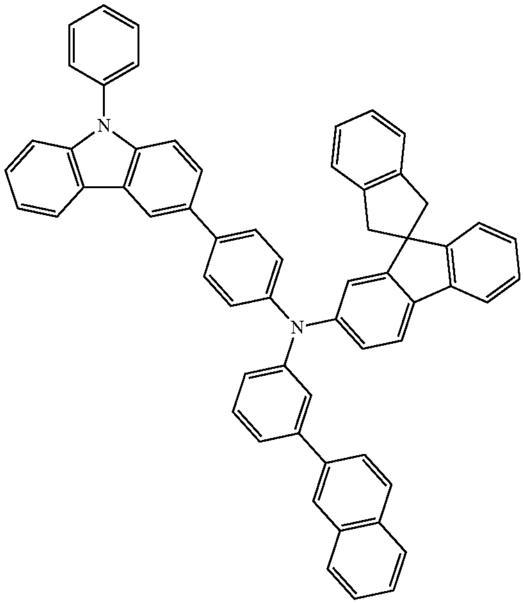
-continued
48
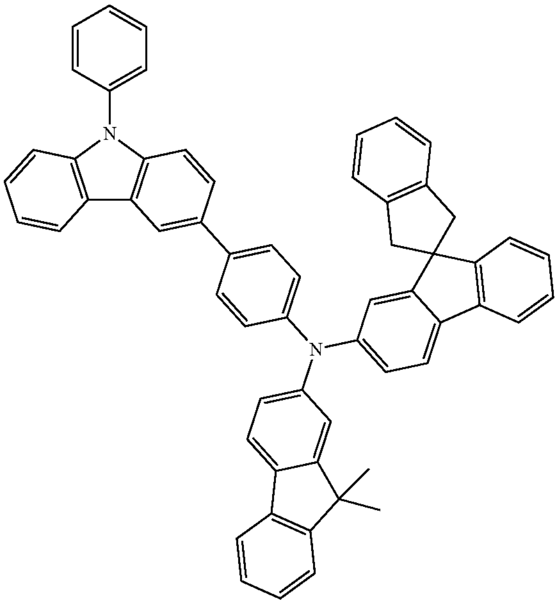
49
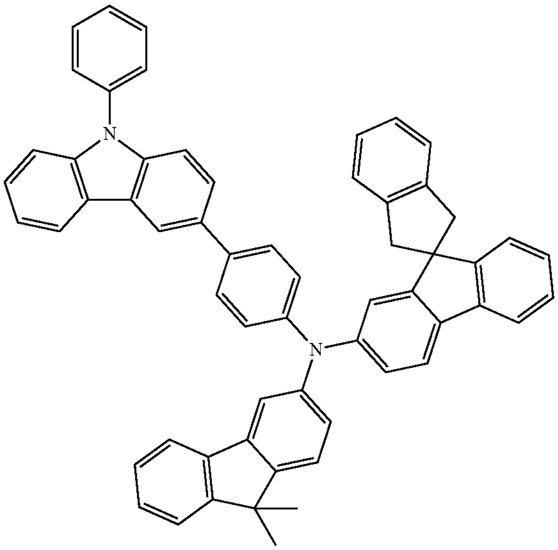

-continued
50
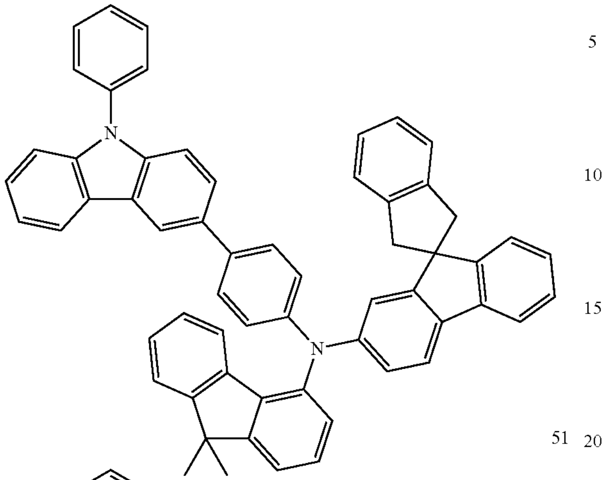
51
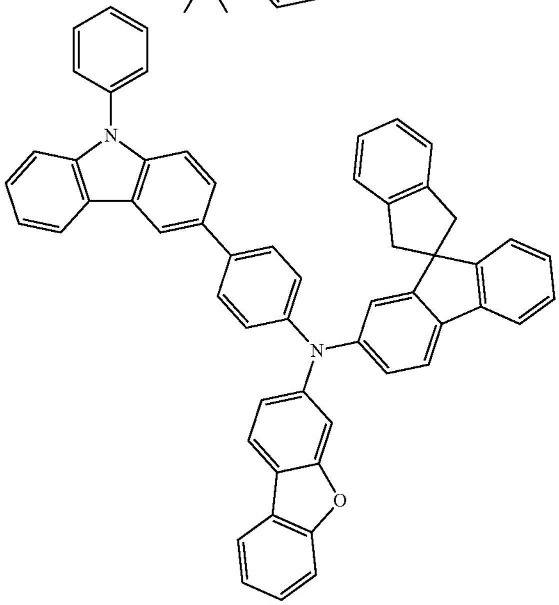
52
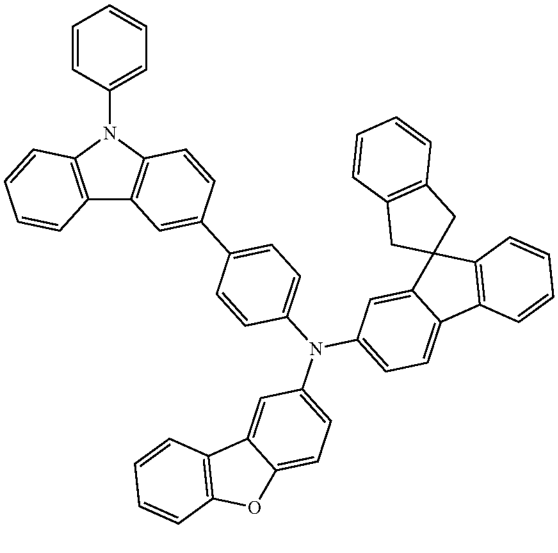
-continued
53
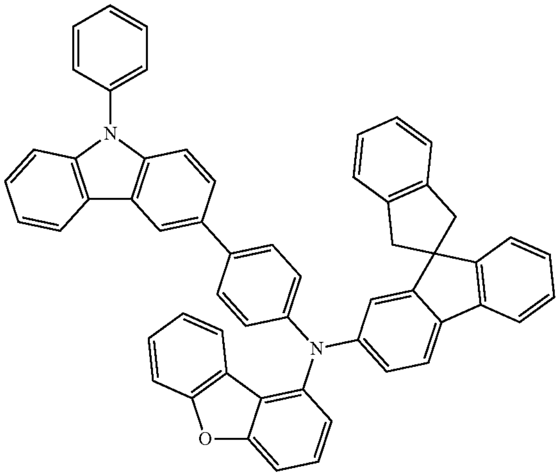
54
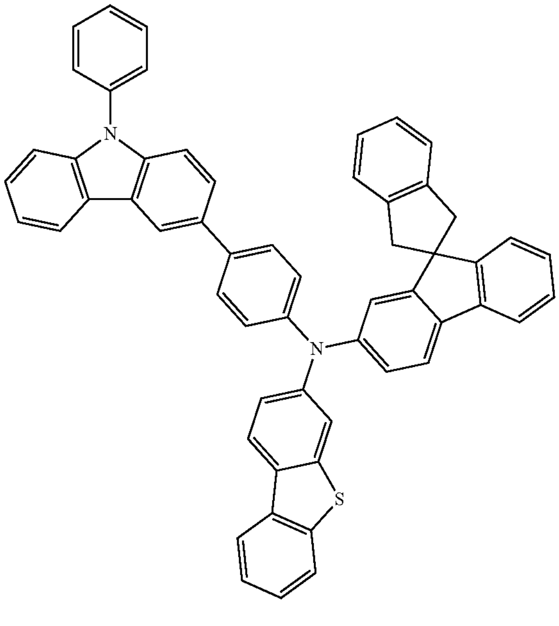

-continued
55
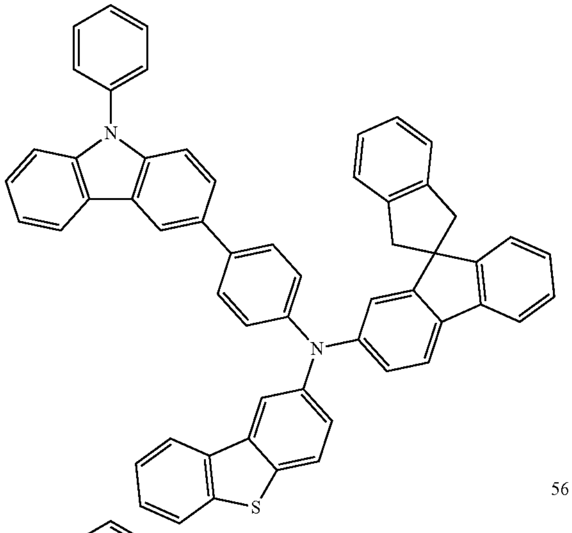
56
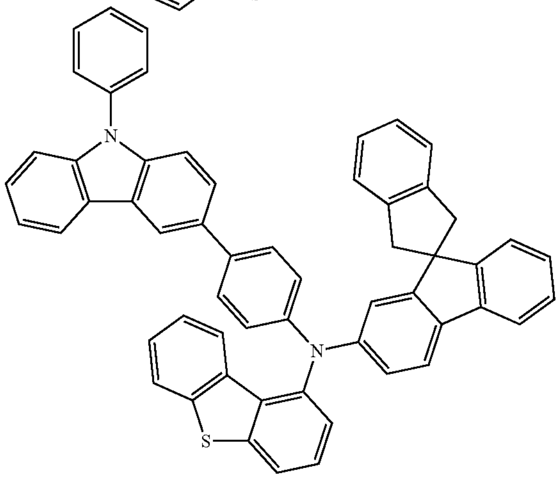
57
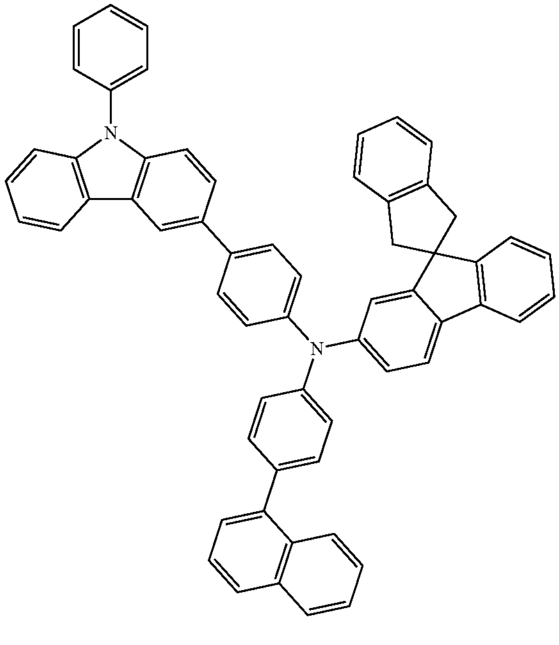
-continued
58
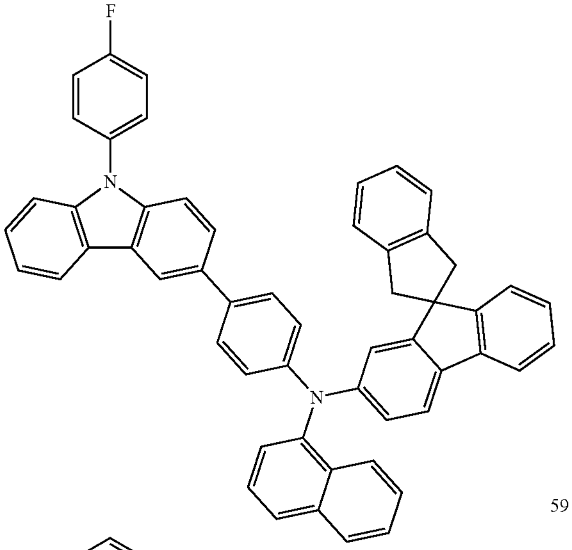
59
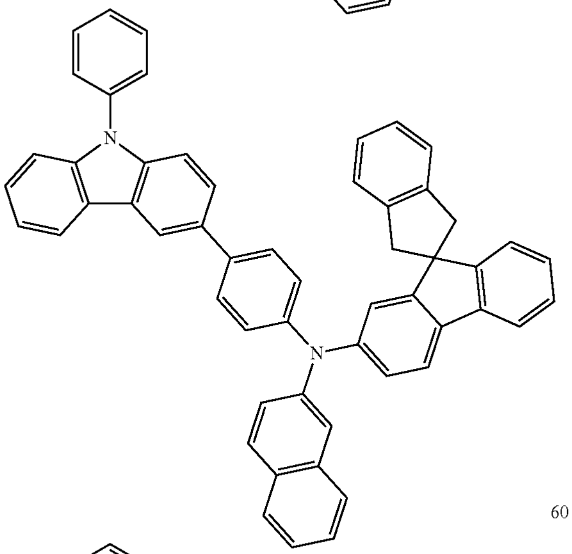
60
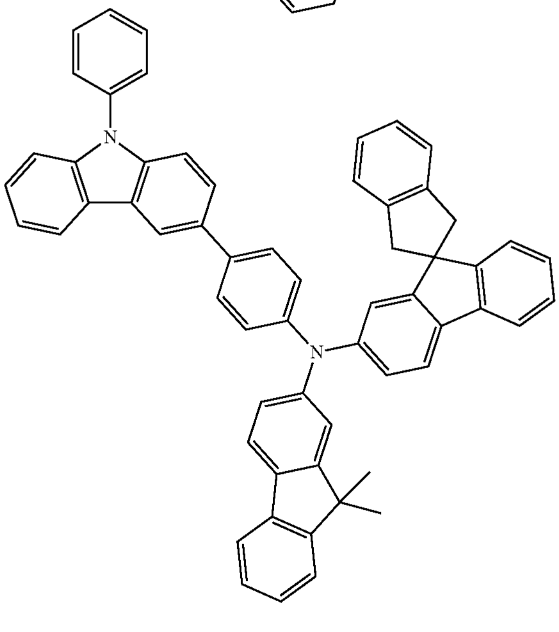

-continued
62
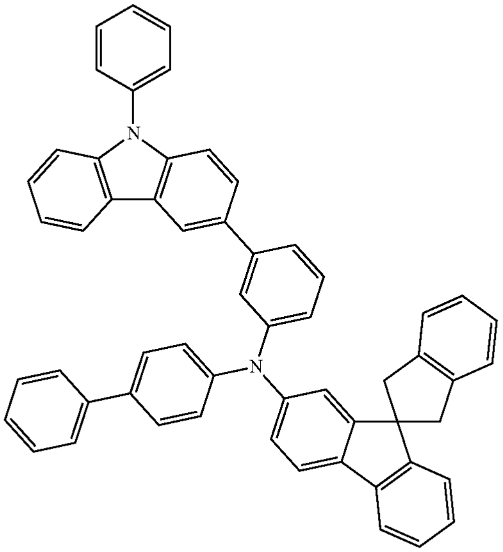
63
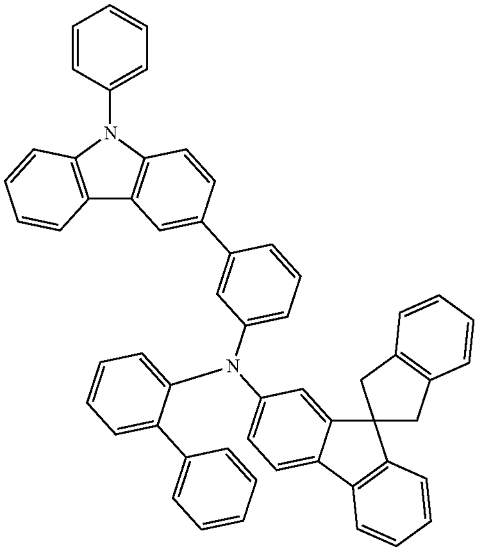
64
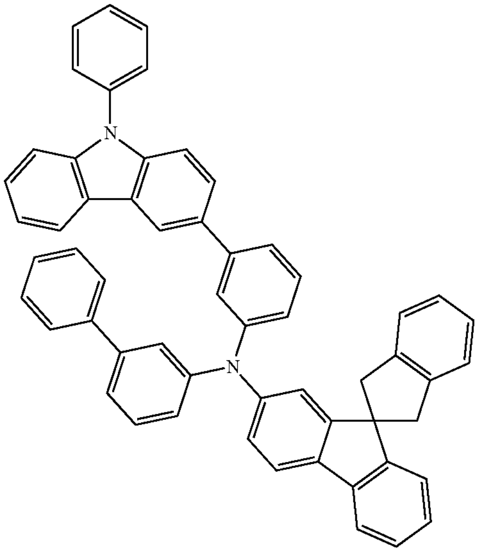
-continued
65
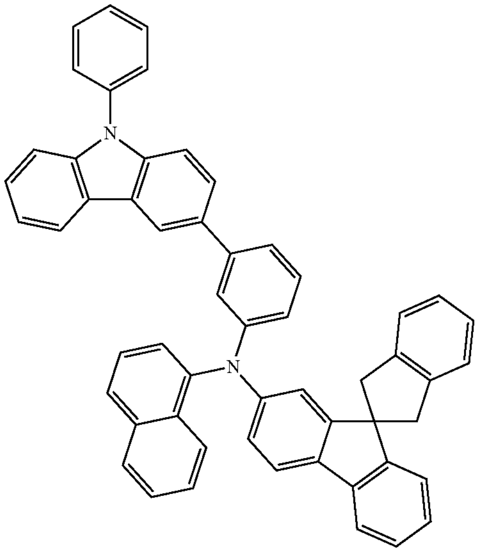
66
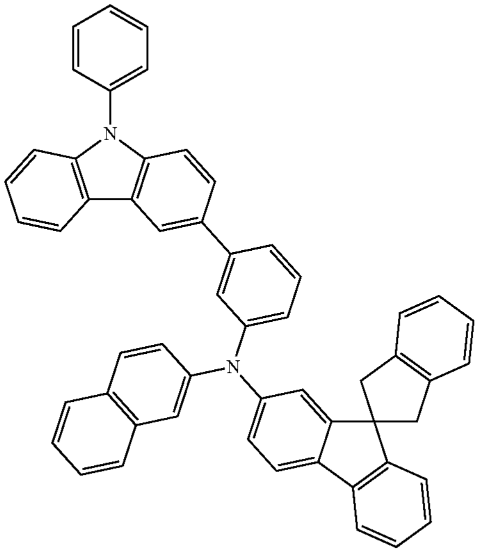
67
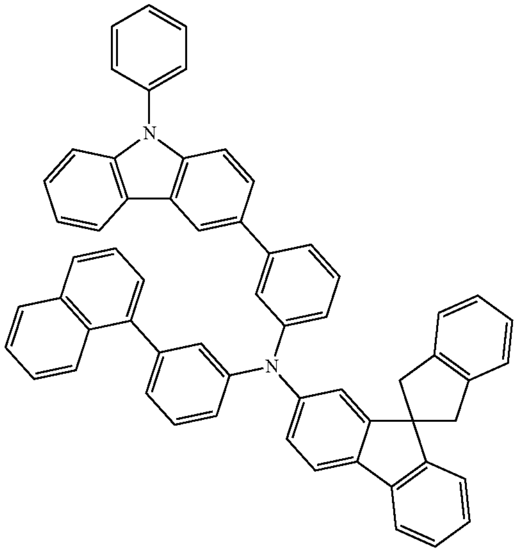

-continued
68
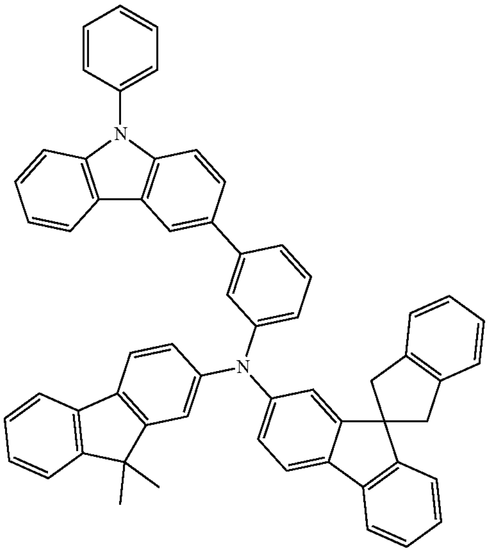
69
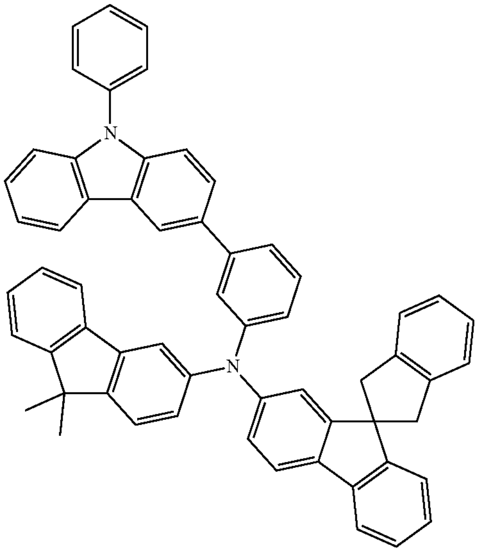
70
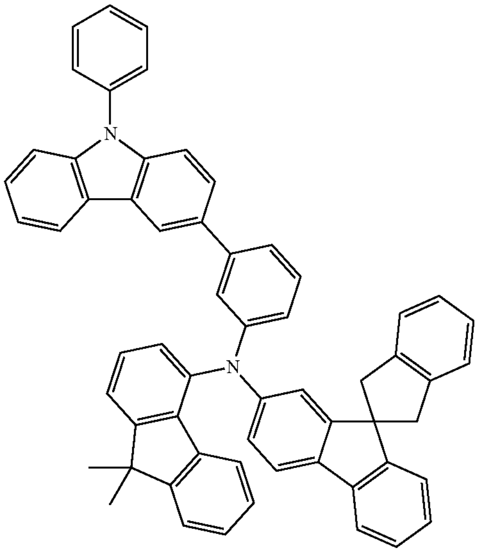
-continued
71
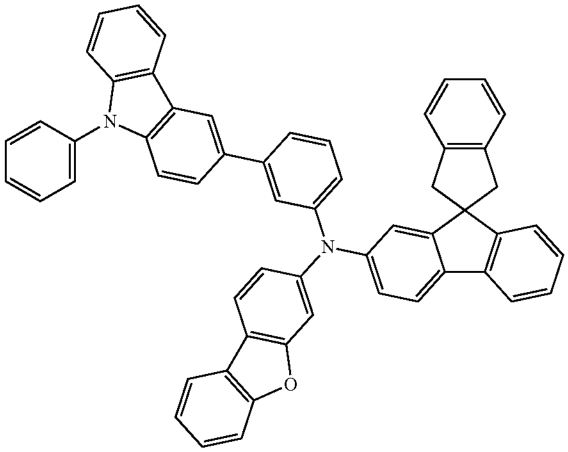
72
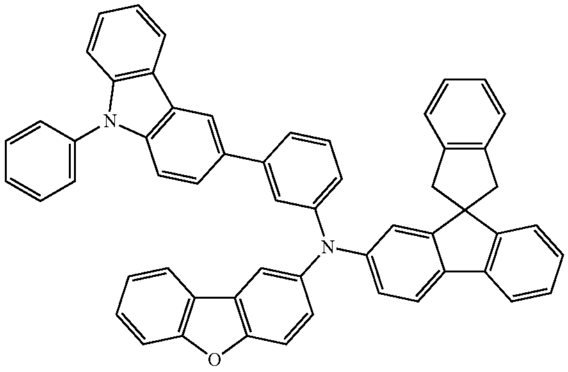
73
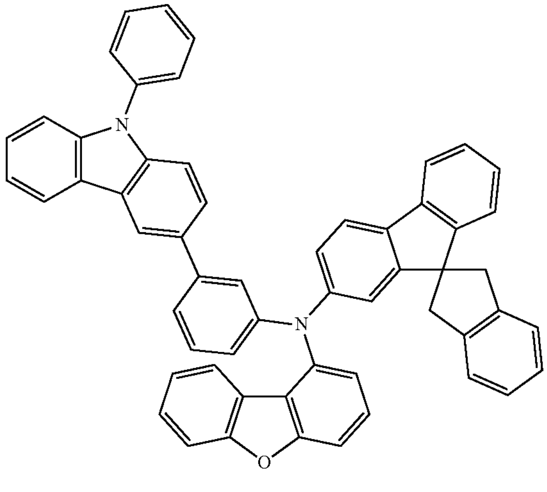

74
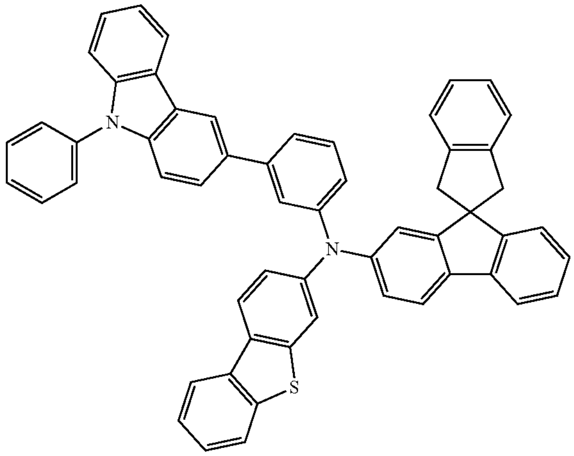
75
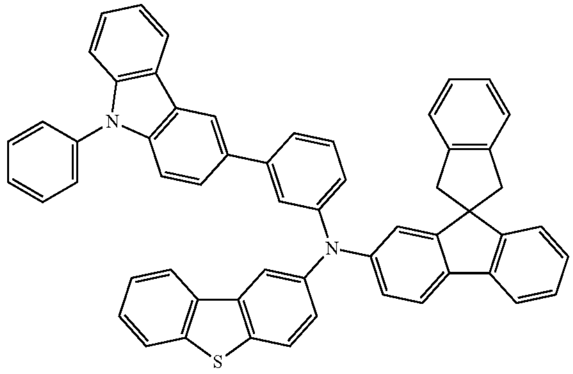
76
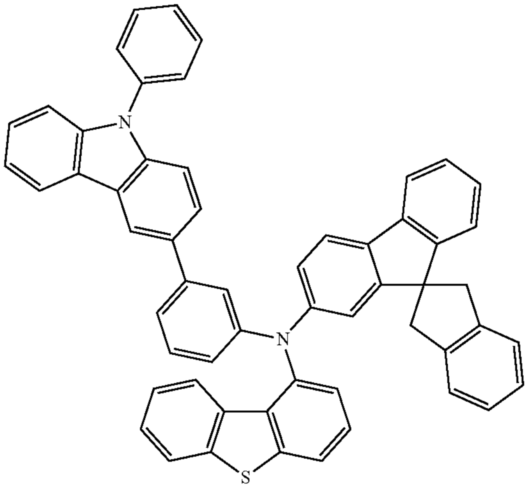
78
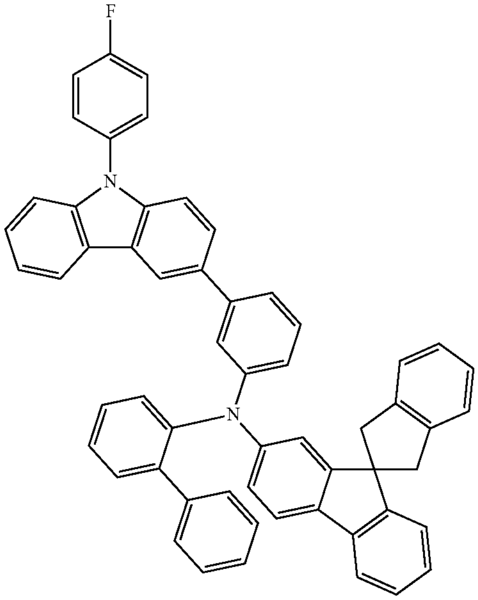
79
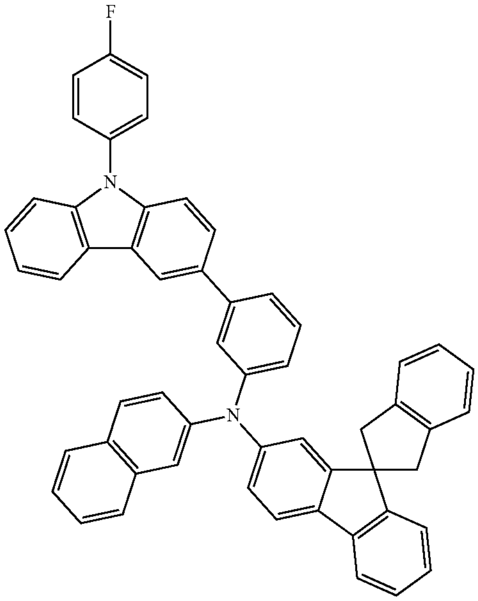

-continued
80
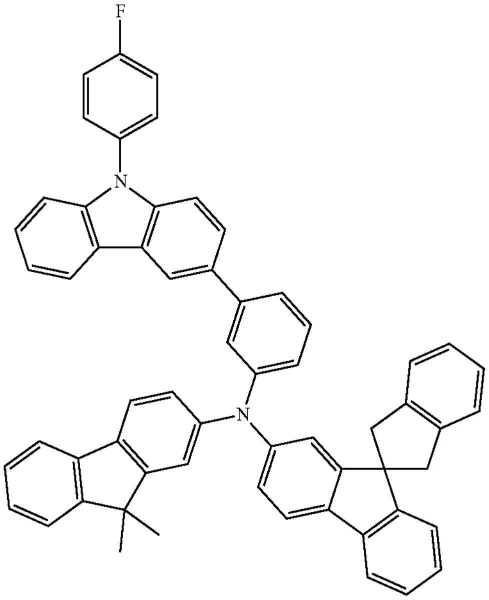
82
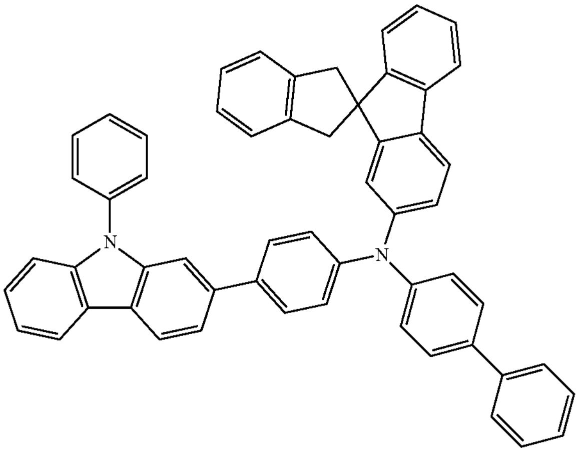
83
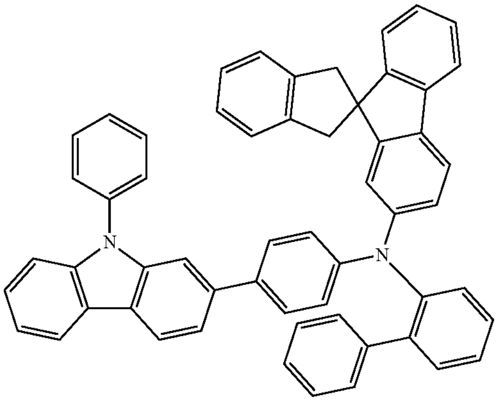
-continued
84
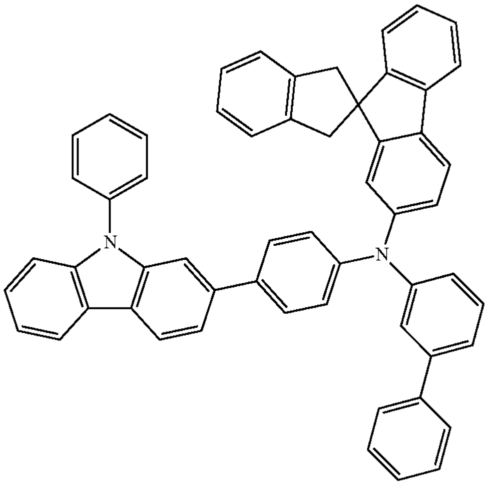
85
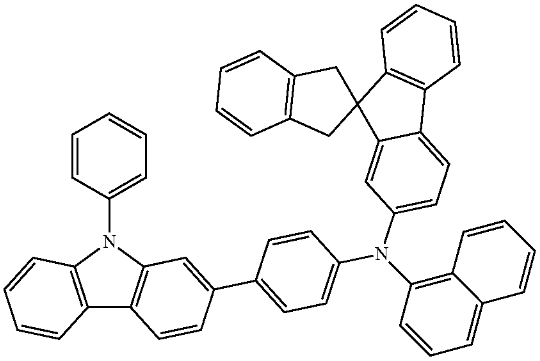
86
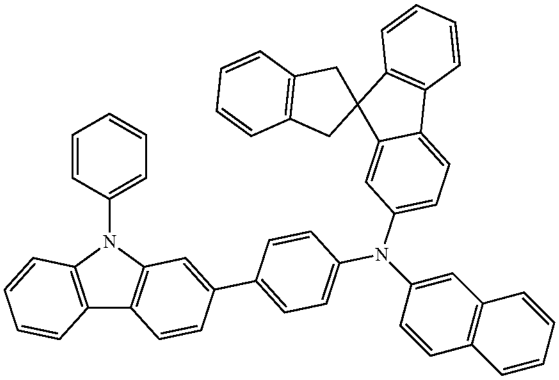
87
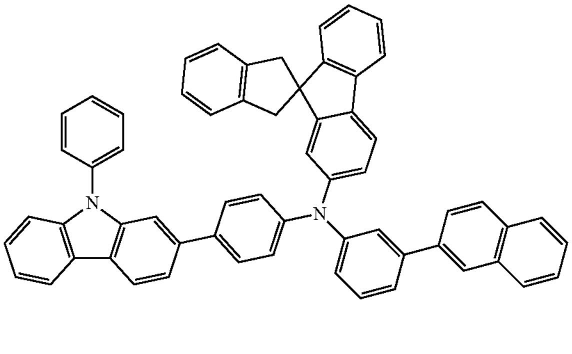

-continued
88
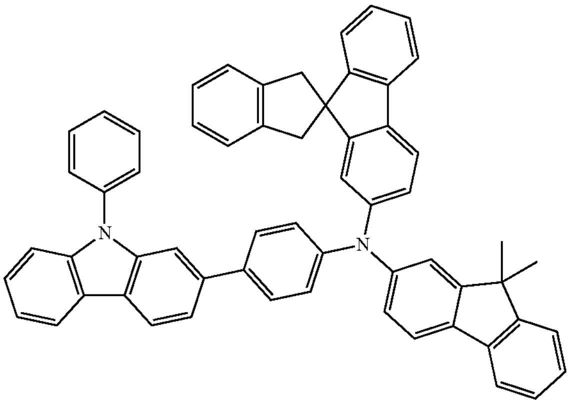
89
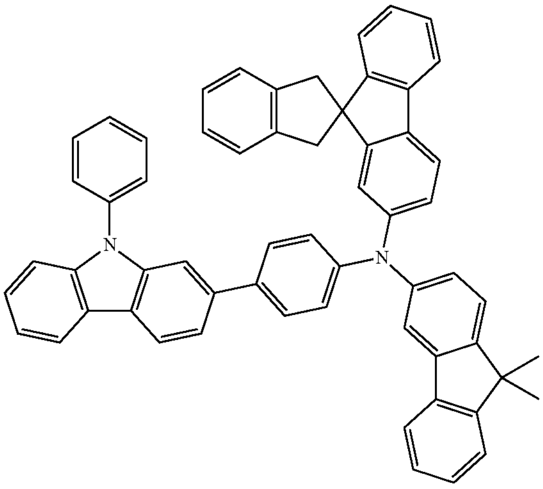
90
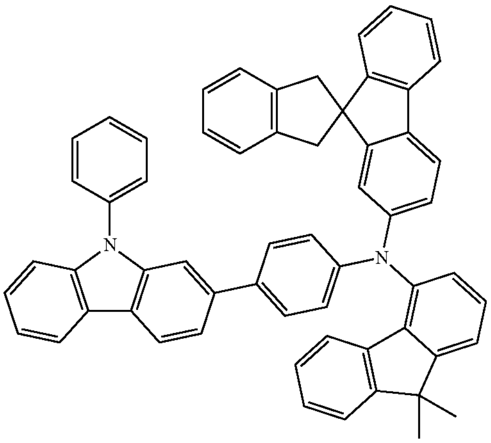
-continued
91
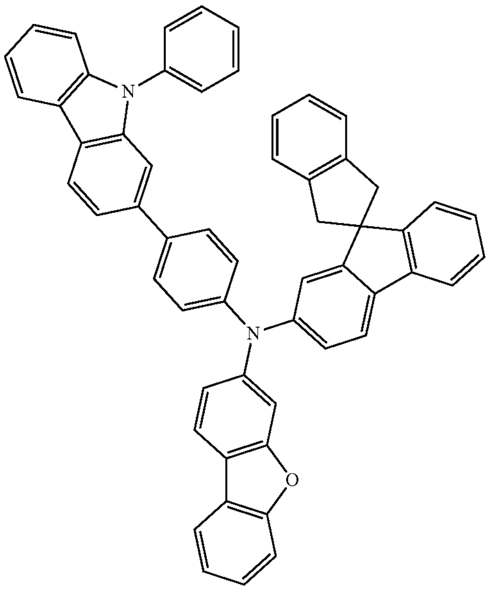
92
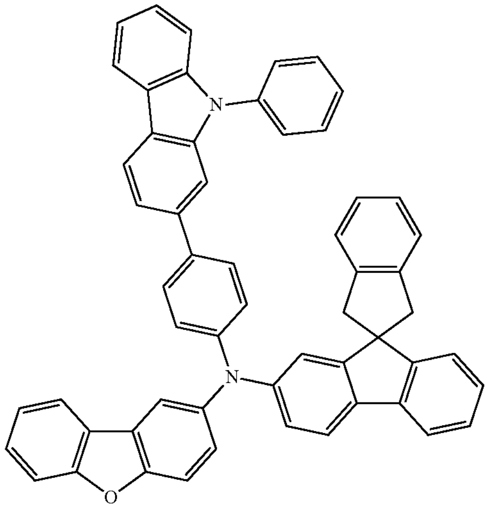
93
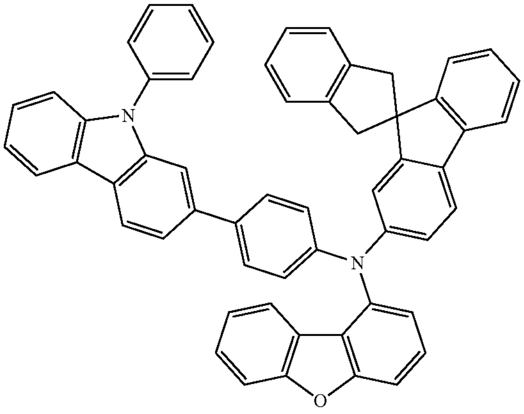

-continued
94
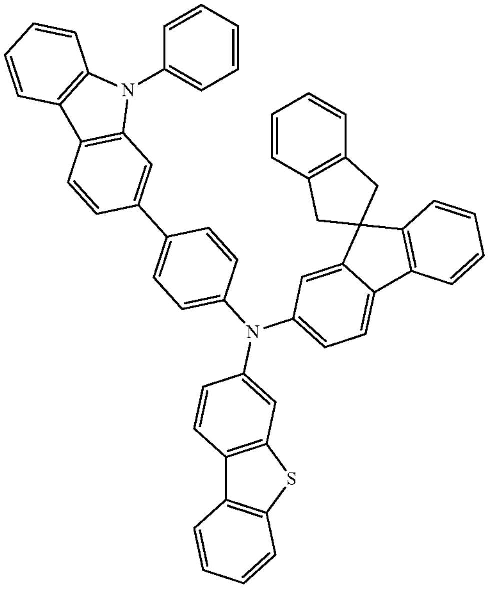
95
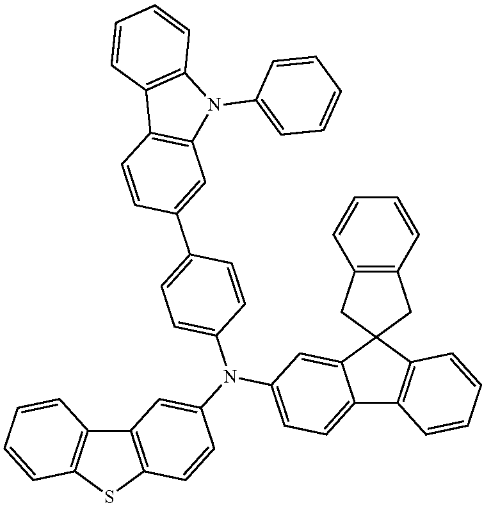
96
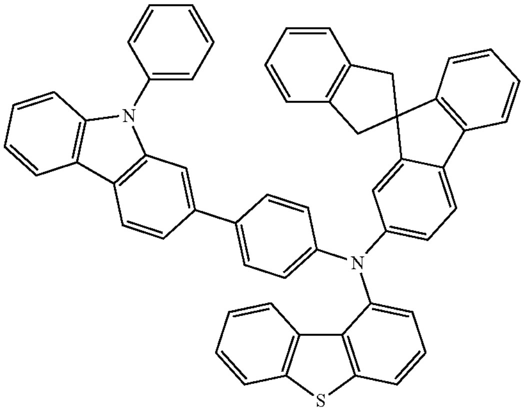
-continued
97
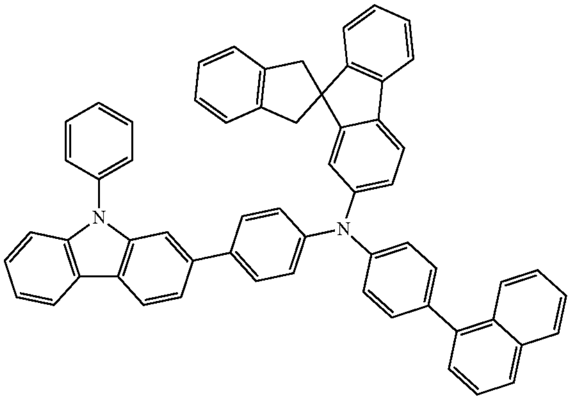
98
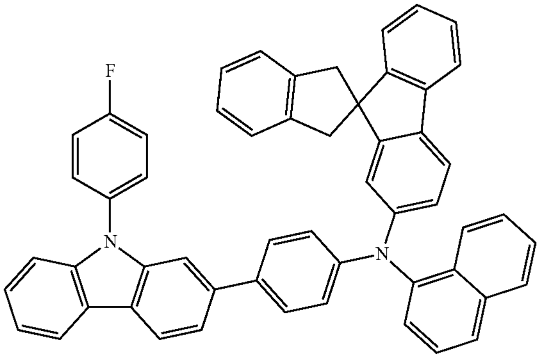
99
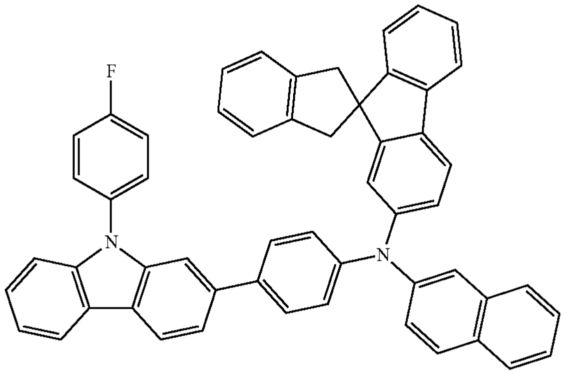
100
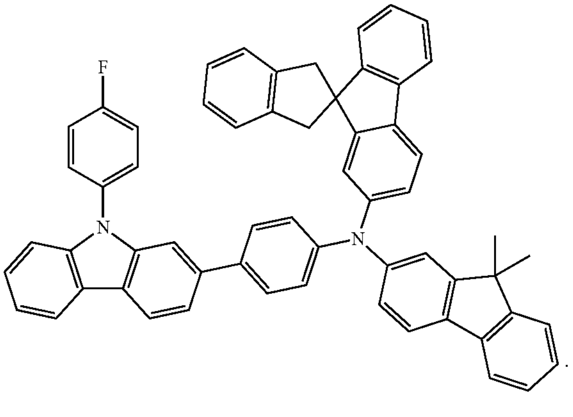

10. An amine compound for an organic electroluminescence device, wherein the amine compound comprises one amine group and is represented by Formula 4-1 or Formula 4-2:

Formula 4-1

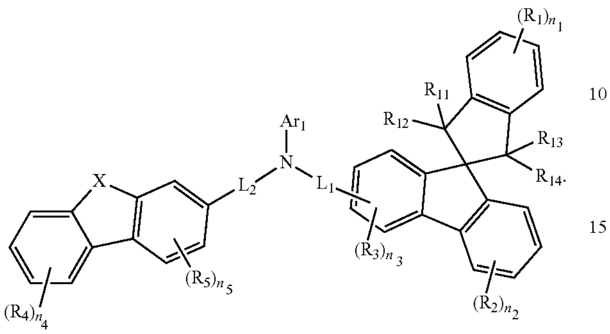

Formula 4-2

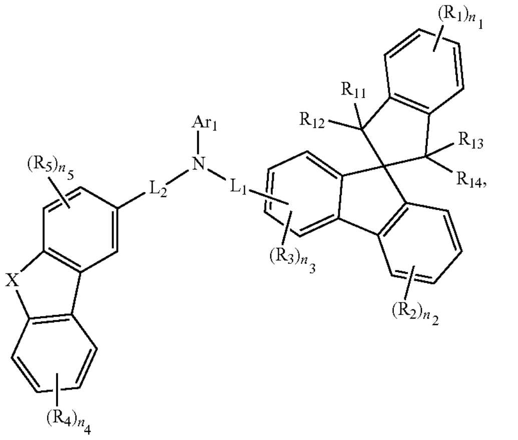

and wherein, in Formula 4-1 and Formula 4-2,

X is $NAr_3$, $Ar_3$ is an unsubstituted phenyl group or an unsubstituted fluorophenyl group, $Ar_1$ is a substituted or unsubstituted aryl group having 10 to 30 ring-forming carbon atoms, or a substituted or unsubstituted heteroaryl group having 2 to 30 ring-forming carbon atoms, $L_1$ is a direct linkage, a substituted or unsubstituted arylene group having 6 to 30 ring-forming carbon atoms, or a substituted or unsubstituted heteroarylene group having 2 to 30 ring-forming carbon atoms, $L_2$ is an unsubstituted phenylene group, $R_1$ to $R_3$ are each independently a hydrogen atom, a deuterium atom, a halogen atom, or a substituted or unsubstituted alkyl group having 1 to 20 carbon atoms, $R_4$ and $R_5$ are each independently a hydrogen atom or a deuterium atom, $R_{11}$ to $R_{14}$ are each independently a hydrogen atom, a deuterium atom, a halogen atom, or a substituted or unsubstituted alkyl group having 1 to 20 ring-forming carbon atoms, $n_1$, $n_2$, and $n_4$ are each independently an integer of 0 to 4, and $n_3$ and $n_5$ are each independently an integer of 0 to 3.

11. The amine compound of claim 10, wherein the amine compound is represented by any one among Formula 5-2 to Formula 5-3:

Formula 5-2

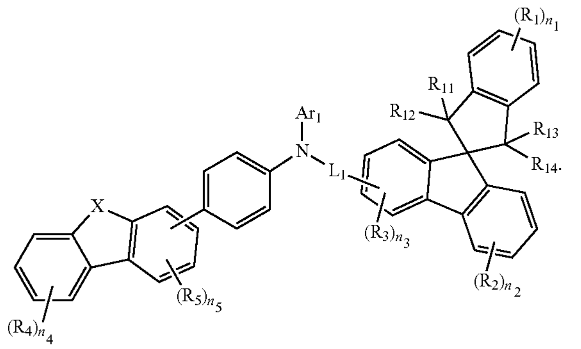

Formula 5-3

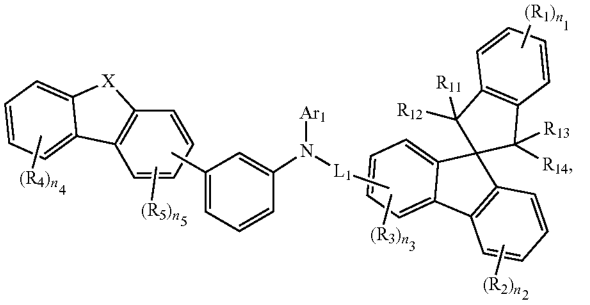

and wherein, in Formula 5-2 and Formula 5-3, $R_6$ is a hydrogen atom or a deuterium atom, $n_6$ is an integer of 0 to 4, and $Ar_1$, X, $L_1$, $R_1$, $R_2$, $R_3$, $R_4$, $R_5$, $R_{11}$, $R_{12}$, $R_{13}$, $R_{14}$, $n_1$, $n_2$, $n_3$, $n_4$, and $n_5$ are each independently the same as defined in Formula 4-1 and Formula 4-2.

12. The amine compound of claim 10, comprising at least one among the compounds of Compound Group 1:

Compound Group 1

42

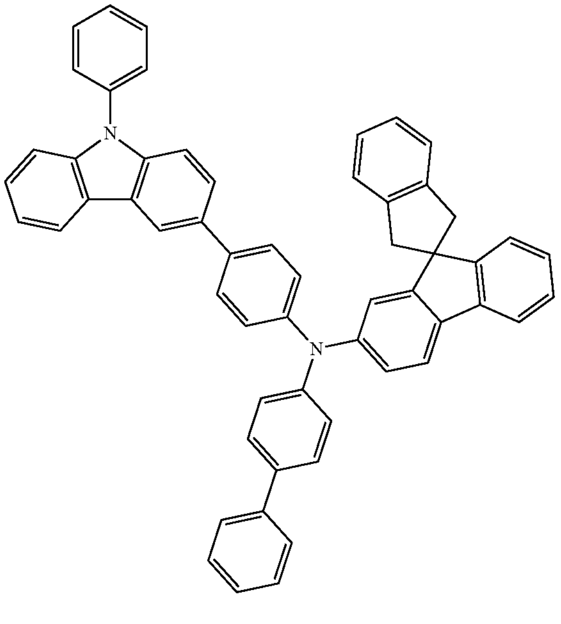

43
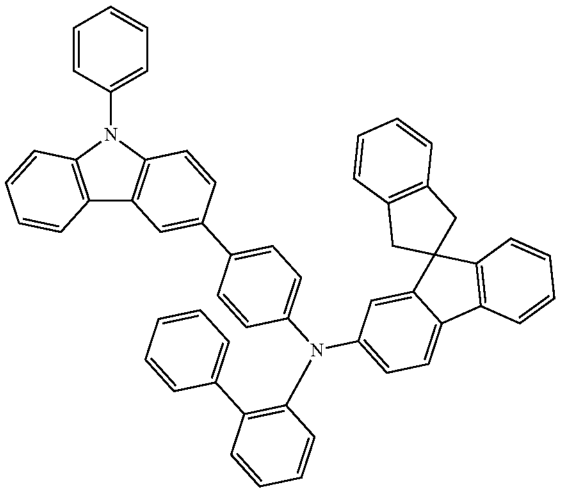
44
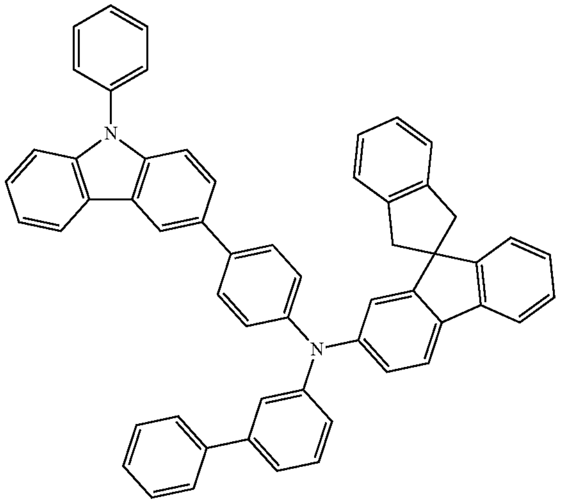
45
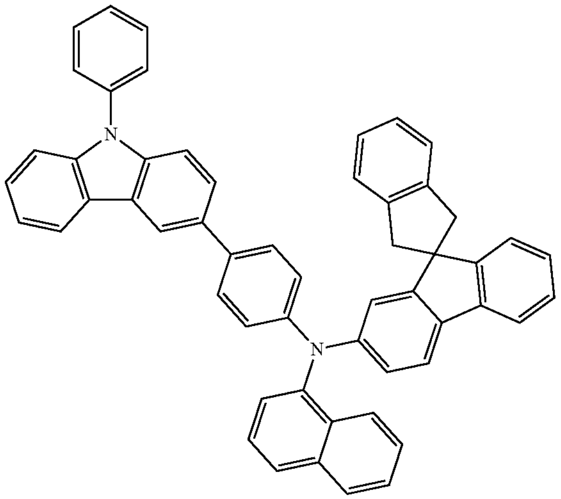
46
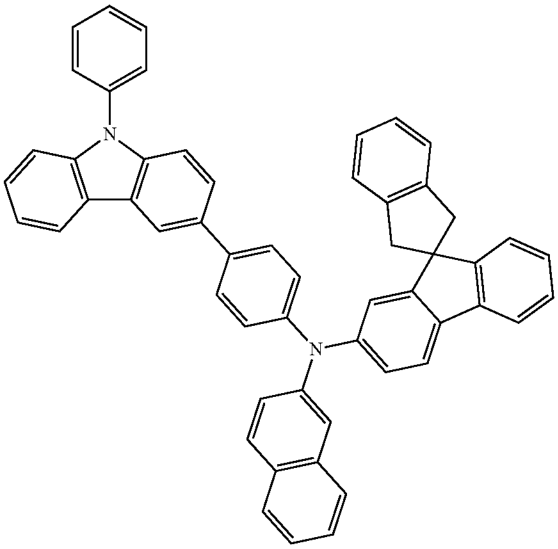
47
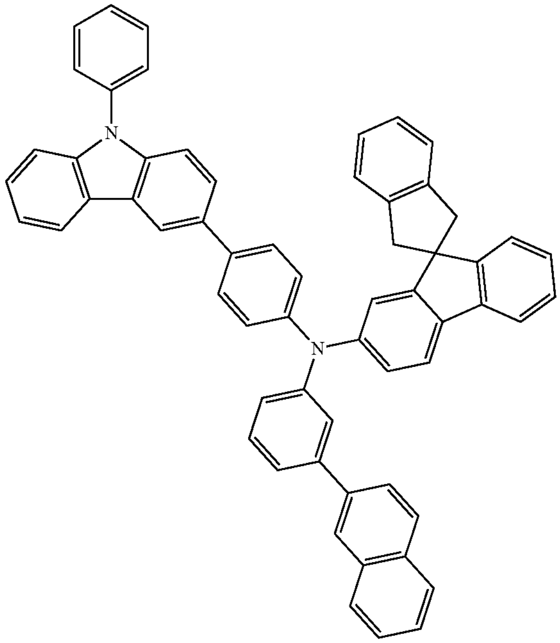

-continued
48
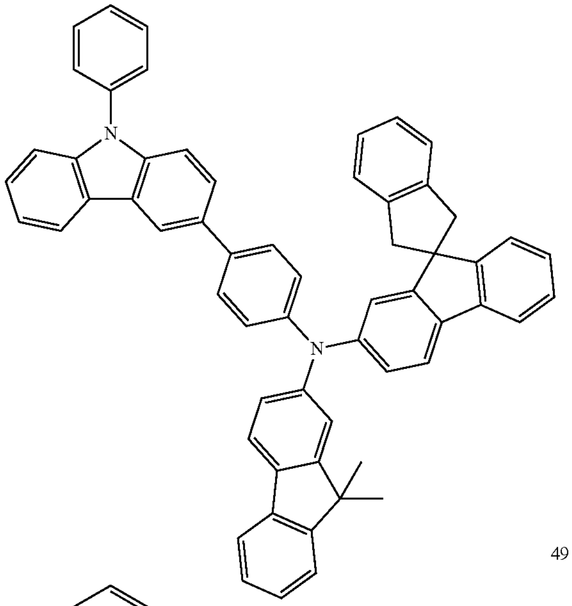
49
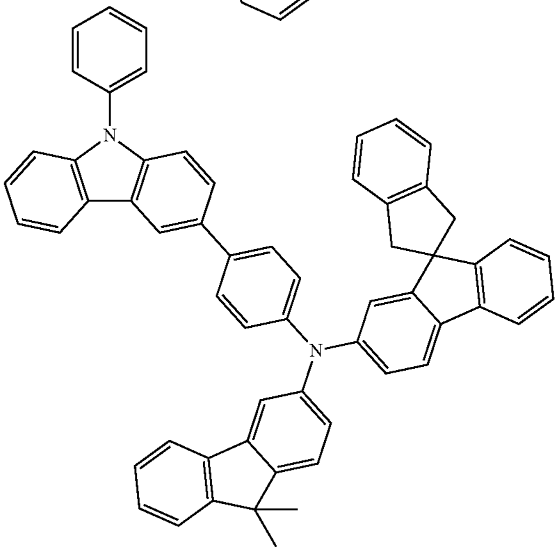
50
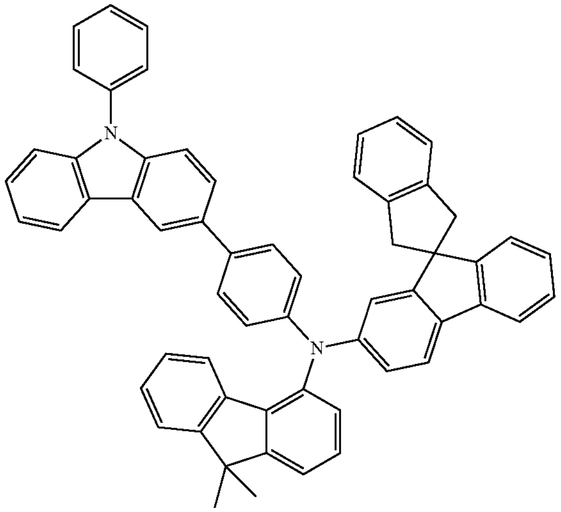
-continued
51
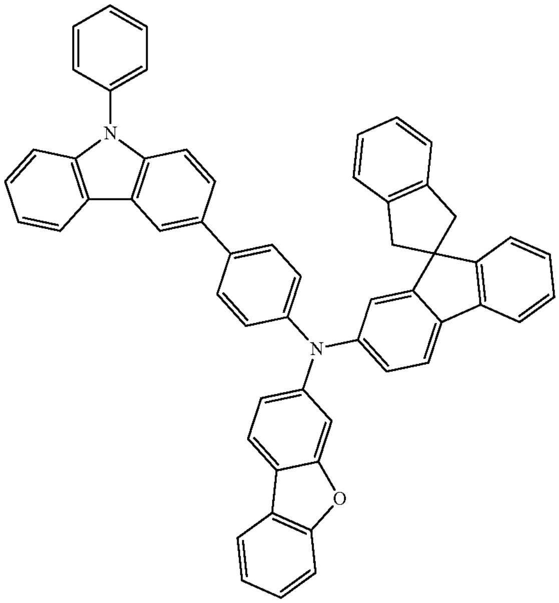
52
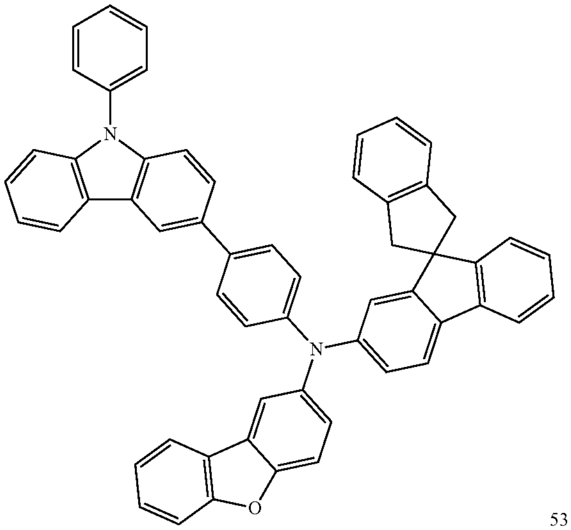
53
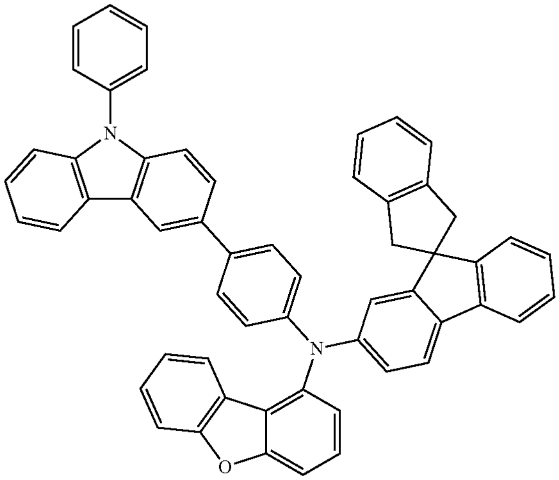

-continued
54
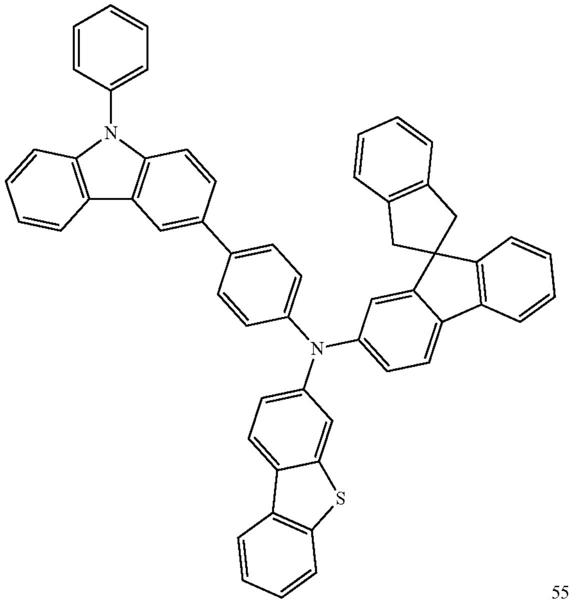
55
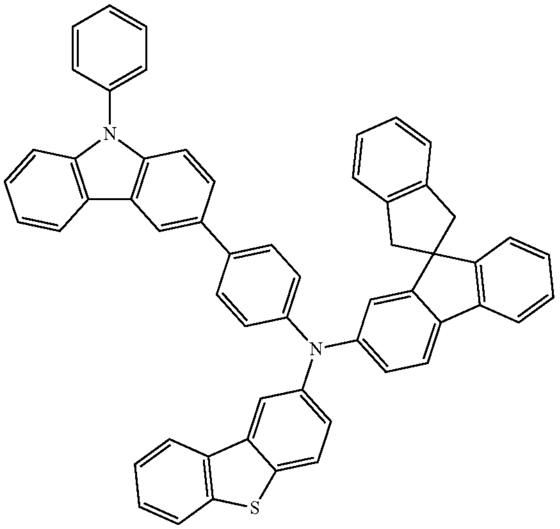
56
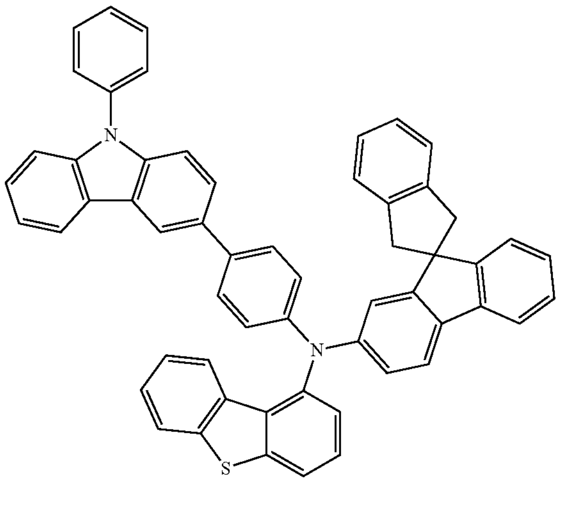
-continued
57
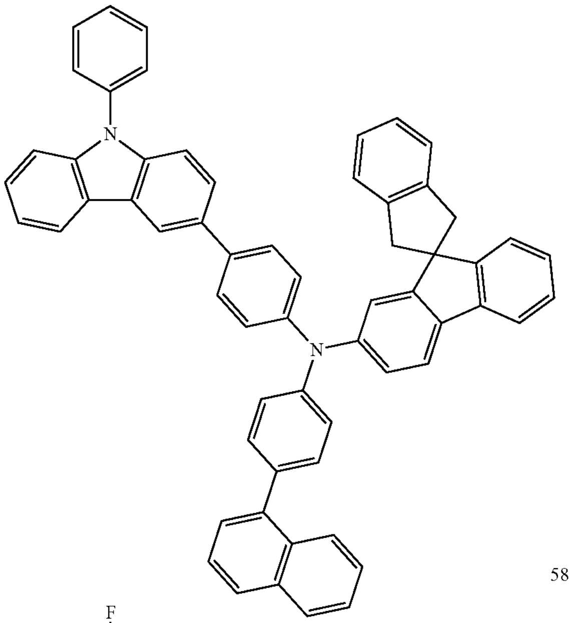
58
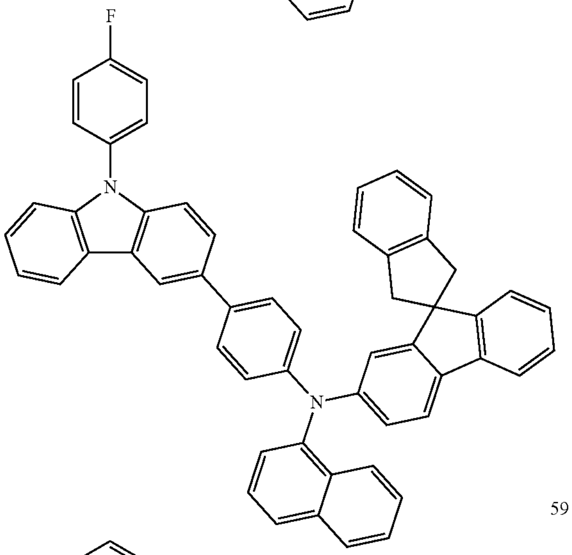
59
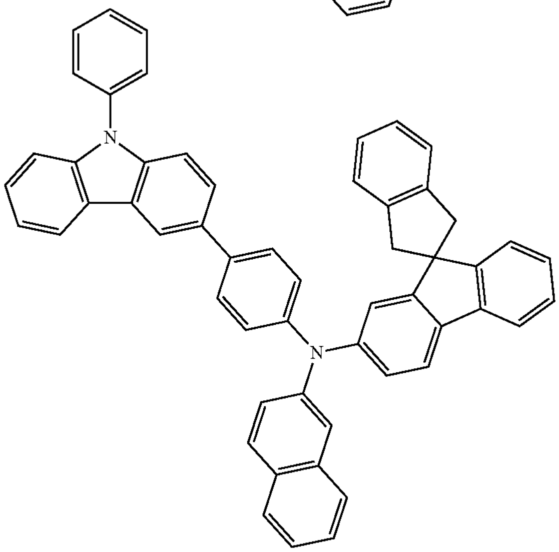

-continued
60
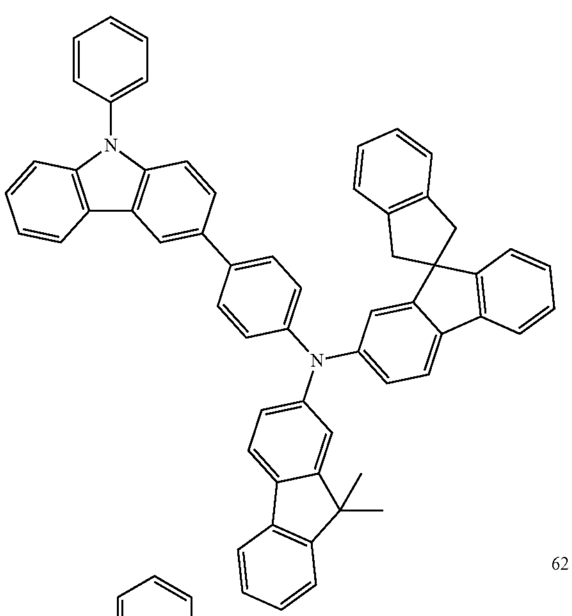
62
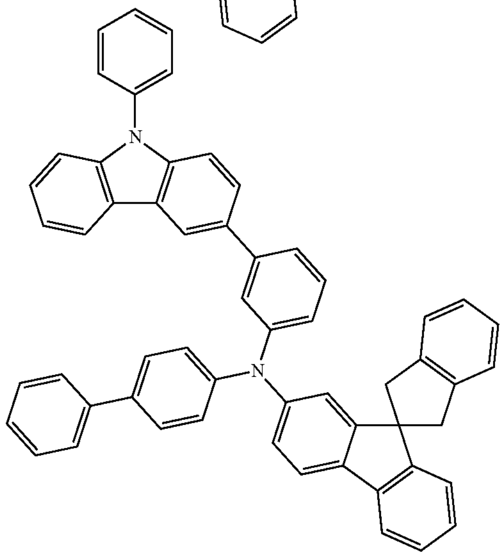
63
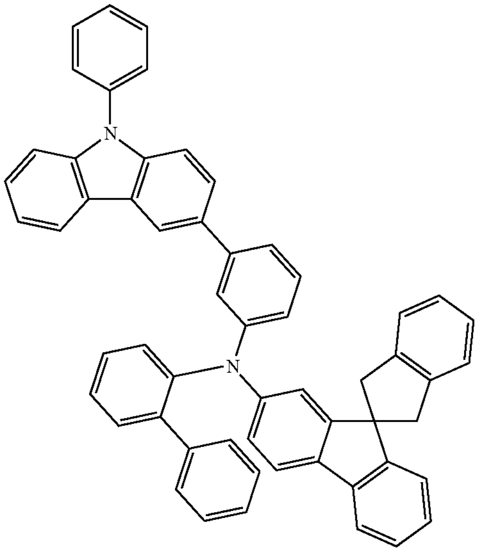
-continued
64
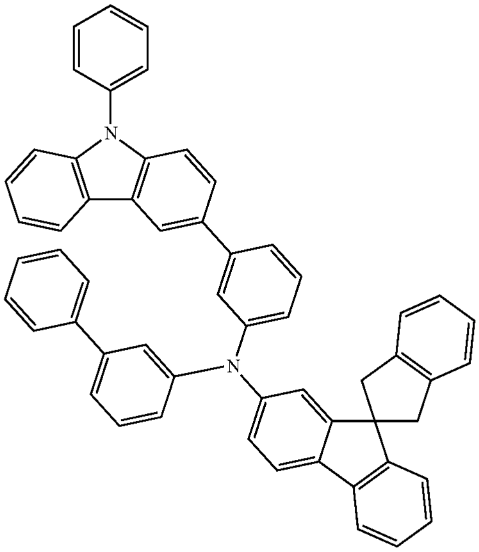
65
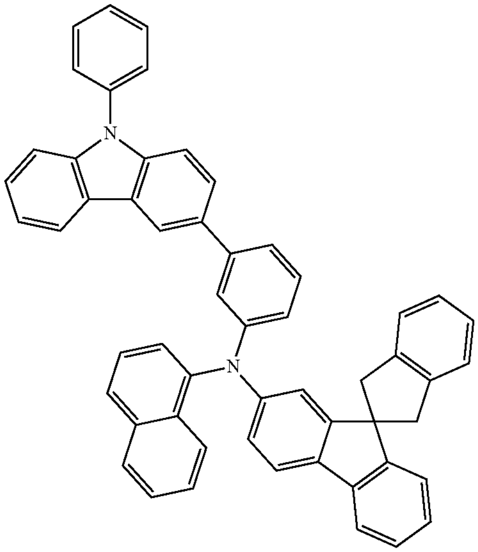
66
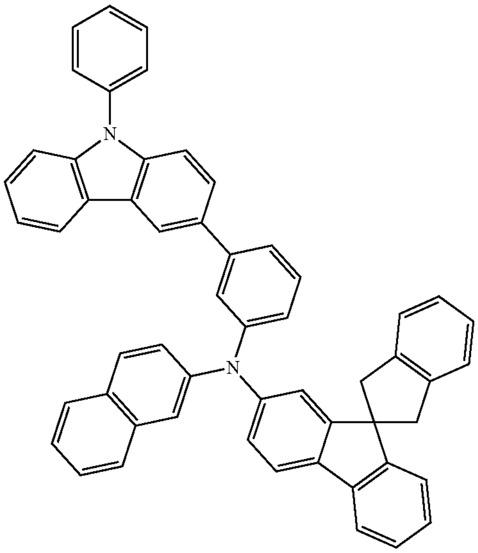

-continued
67
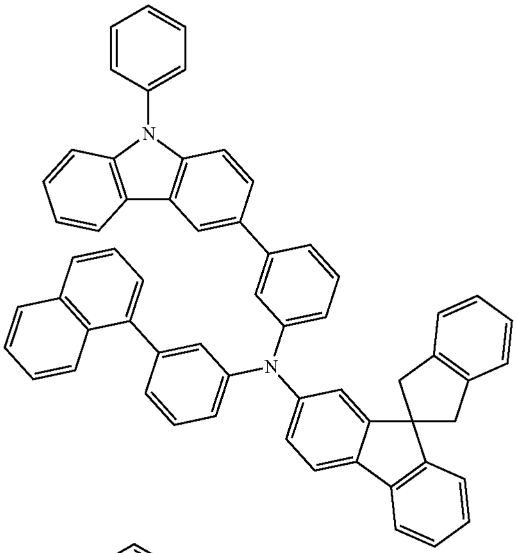
68
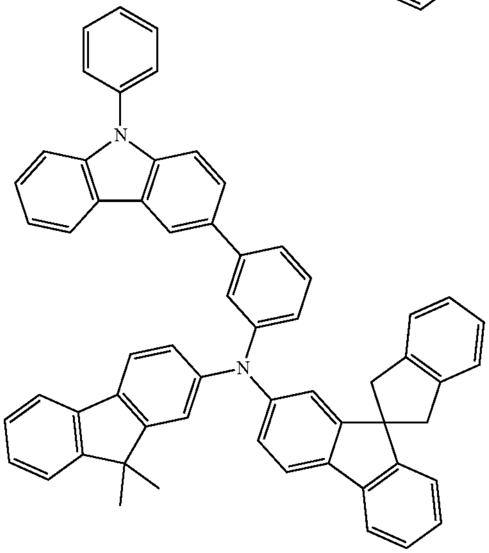
69
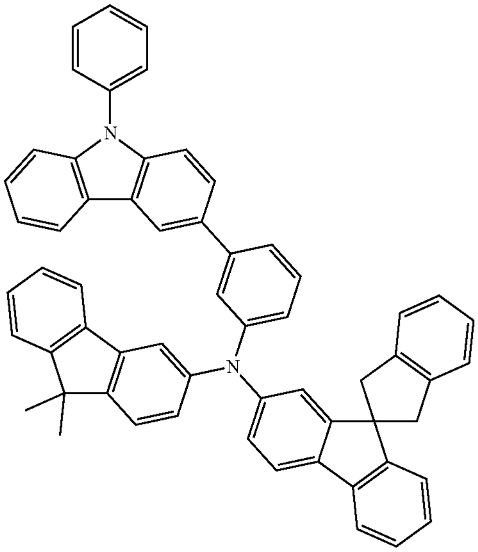
70
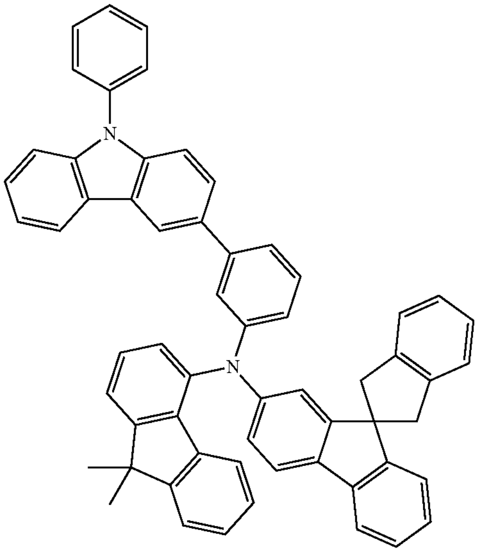
71
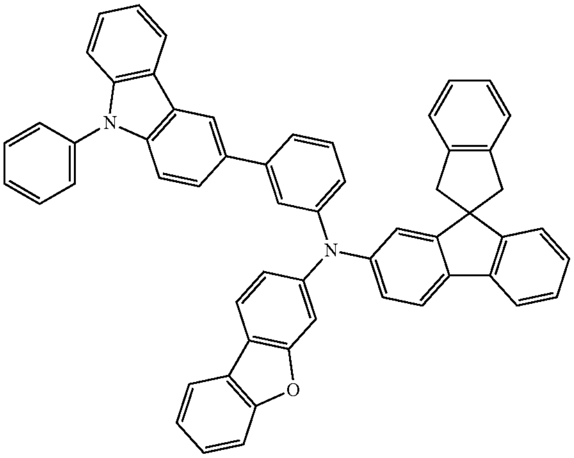
72
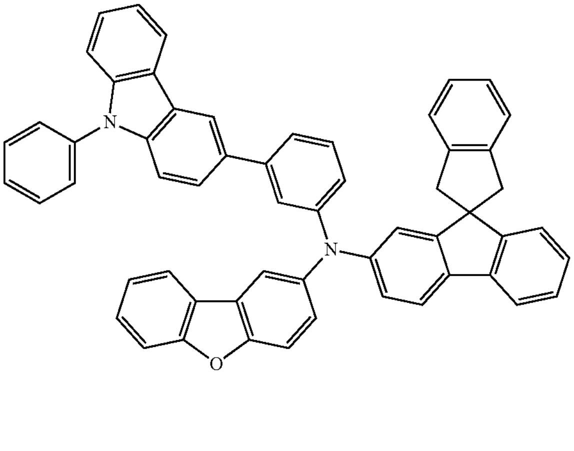

-continued
73
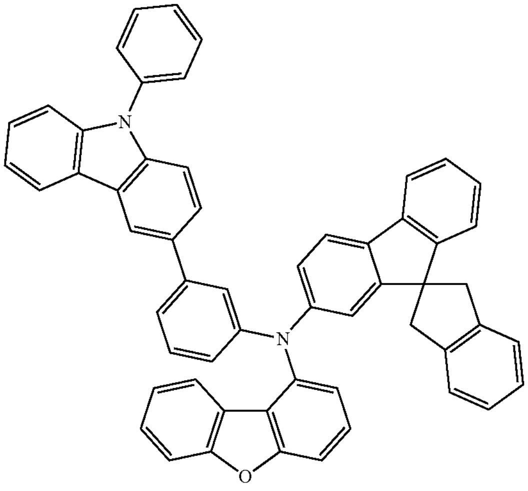
74
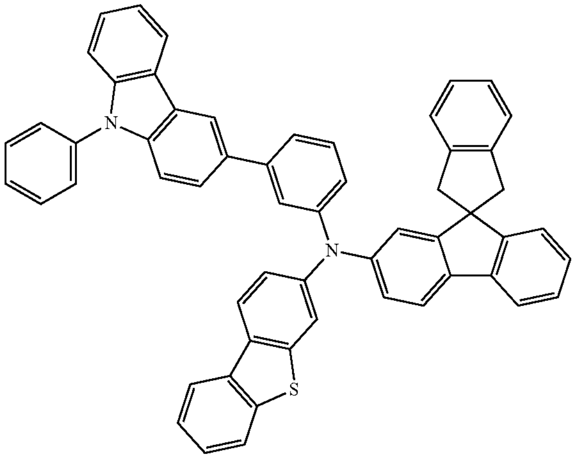
75
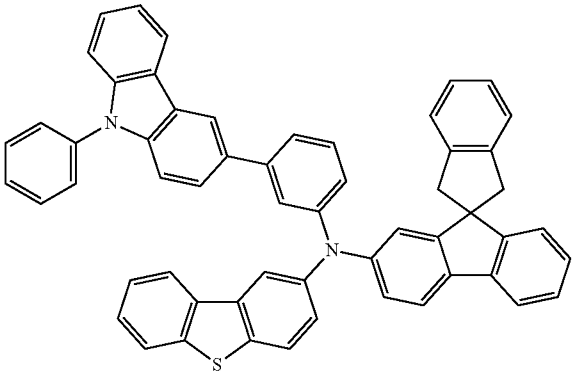
-continued
76
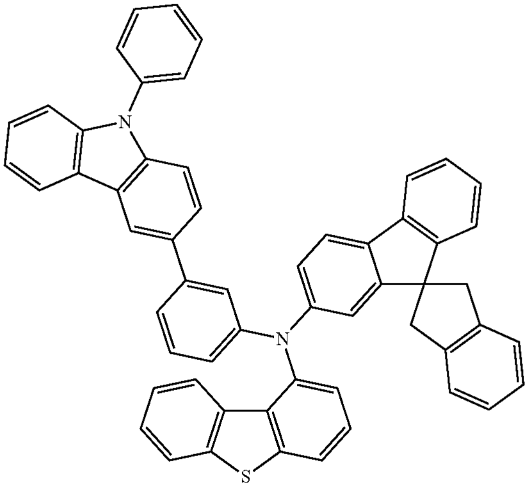
78
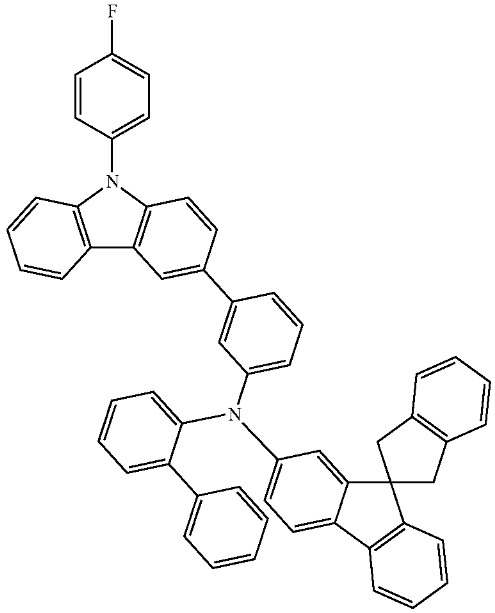

-continued
79
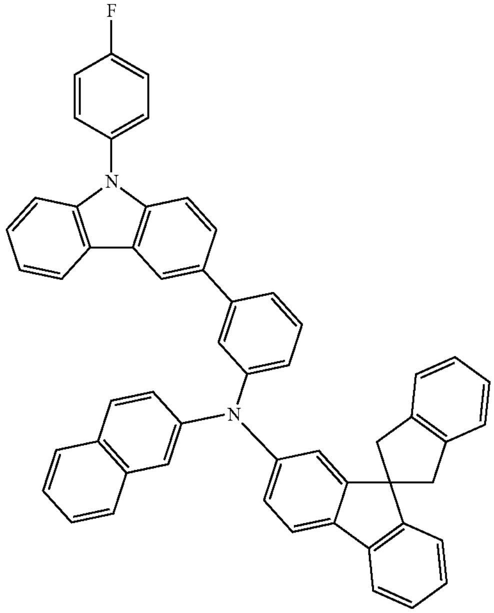
80
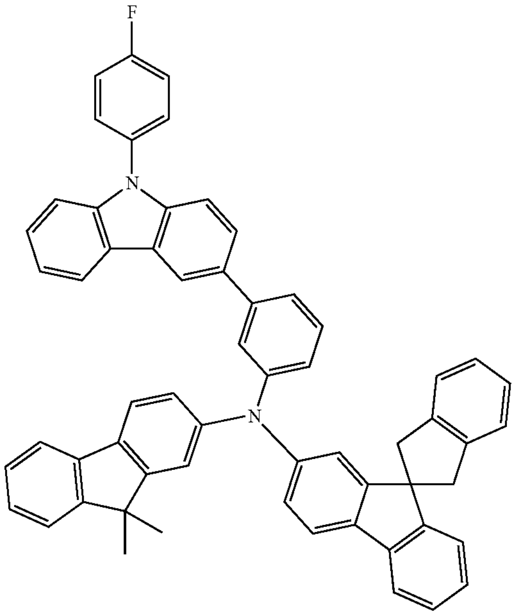
-continued
82
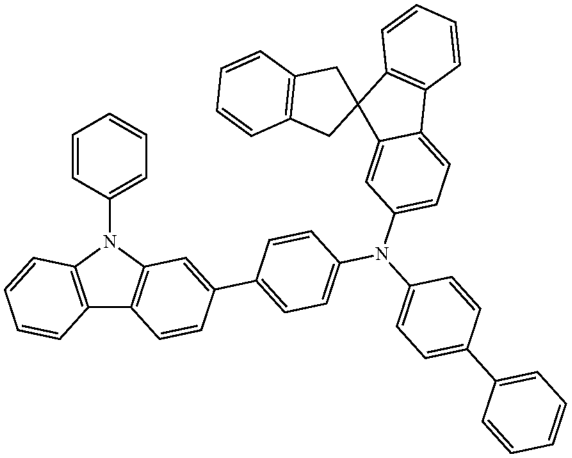
83
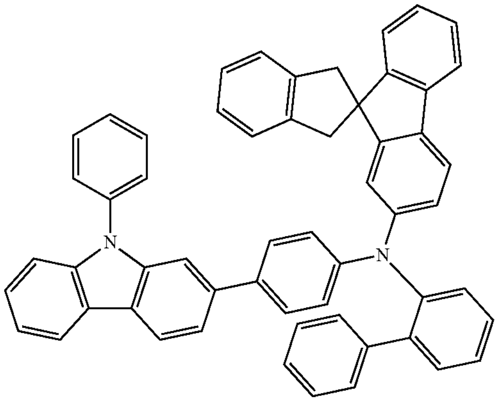
84
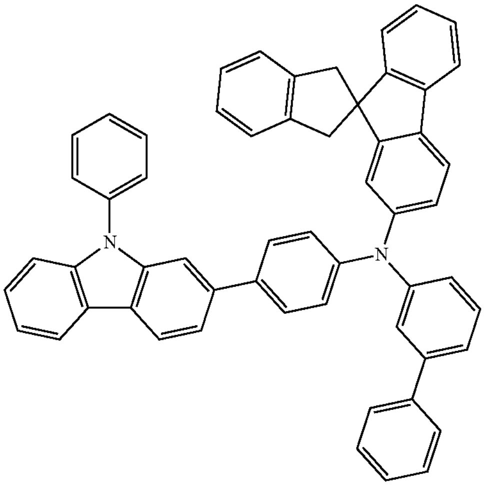

-continued
85
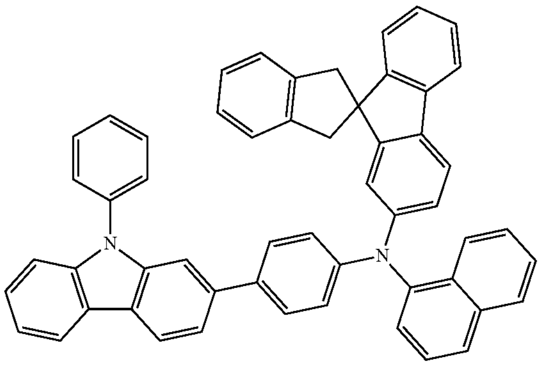
86
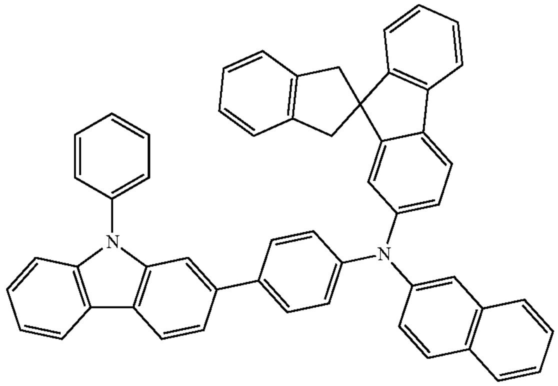
87
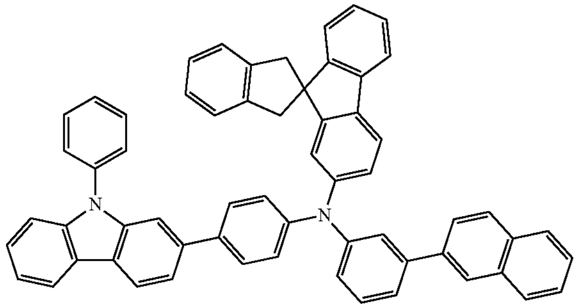
88
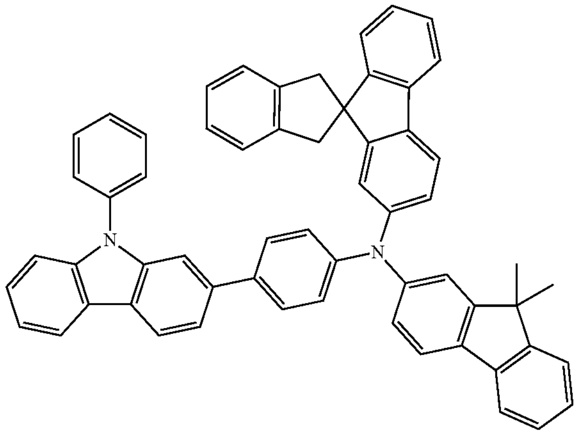
-continued
89
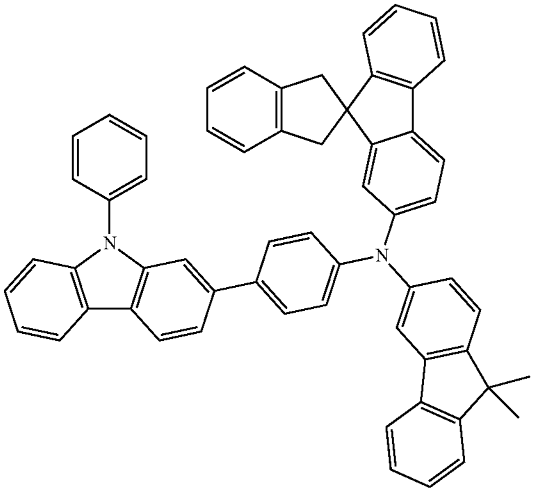
90
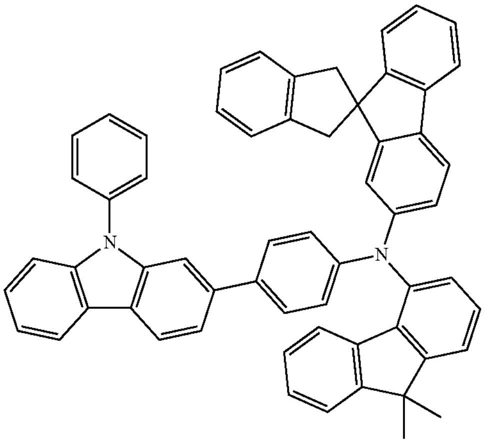
91
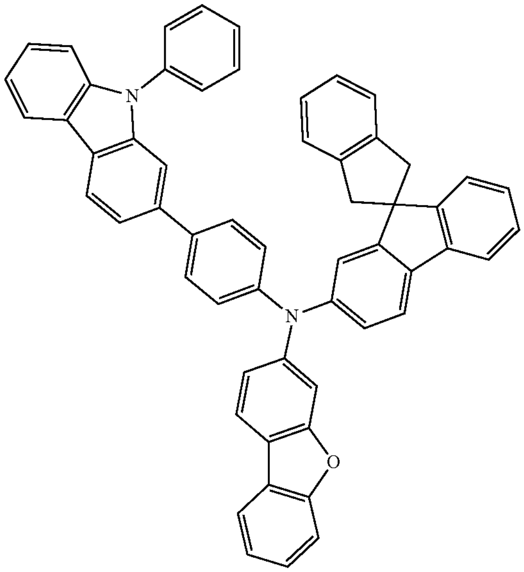

-continued
92
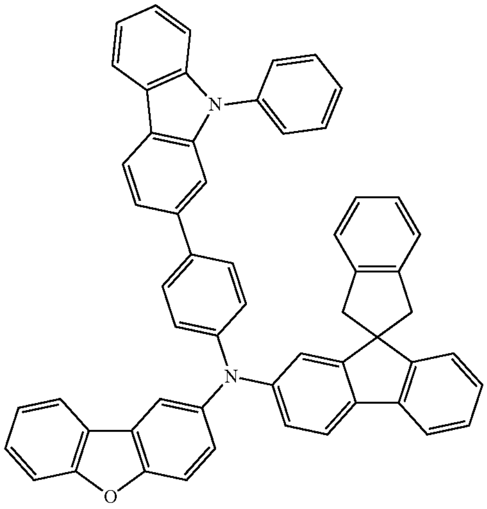
93
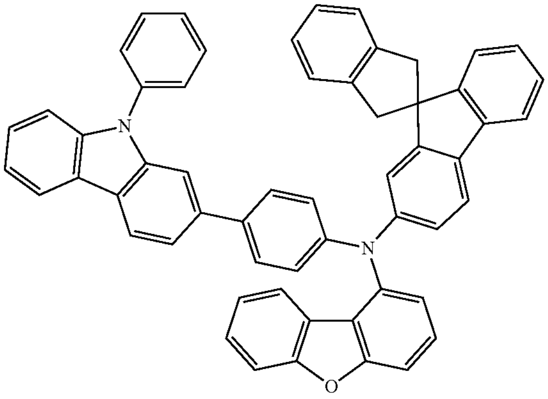
94
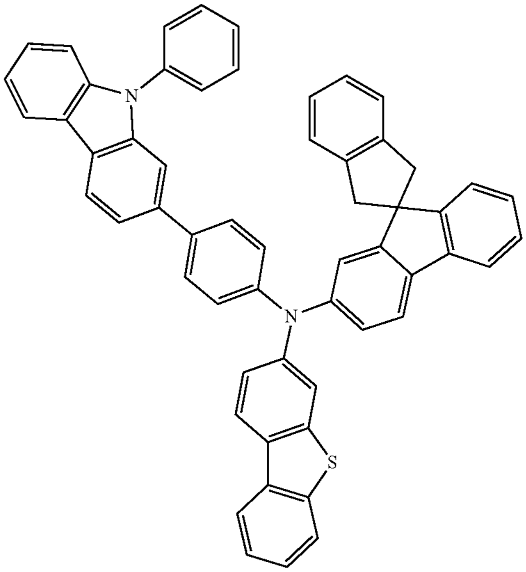
-continued
95
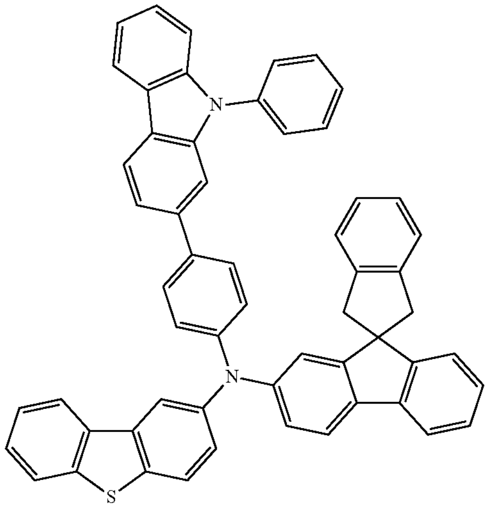
96
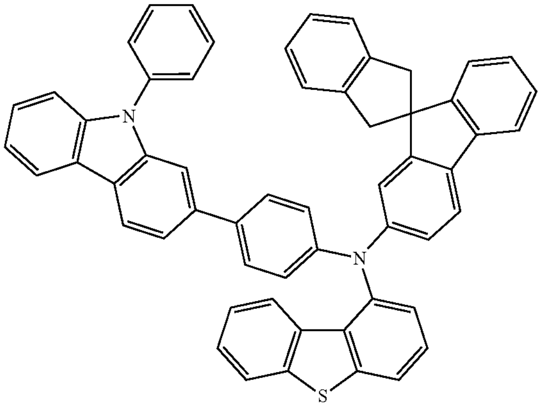
97
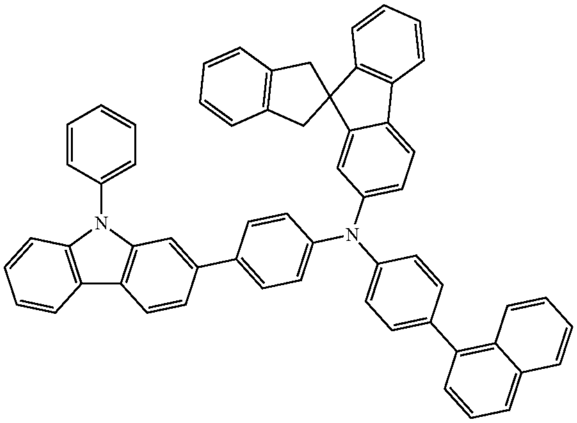

-continued
98
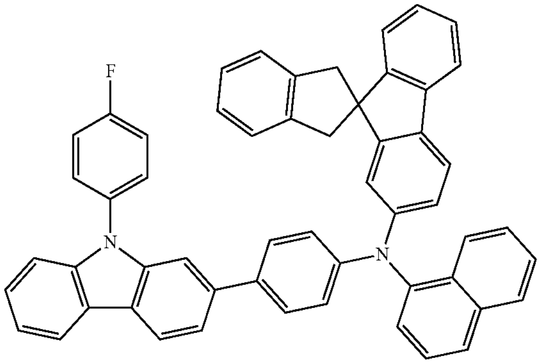
99
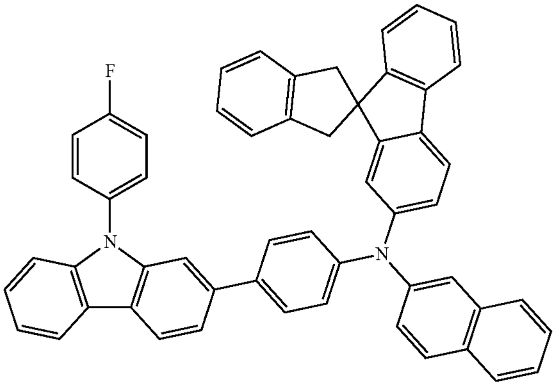
-continued
100
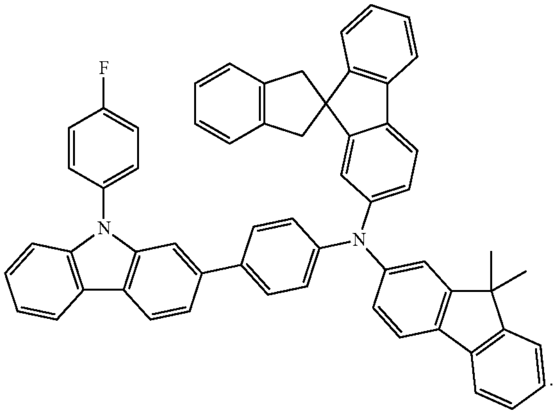
* * * * *